US010039864B2

(12) United States Patent
Esfand et al.

(10) Patent No.: US 10,039,864 B2
(45) Date of Patent: Aug. 7, 2018

(54) OLIGOFLUORINATED CROSS-LINKED POLYMERS AND USES THEREOF

(71) Applicant: Interface Biologics, Inc., Toronto (CA)

(72) Inventors: Roseita Esfand, Mississauga (CA); J. Paul Santerre, Whitby (CA); Mark J. Ernsting, Toronto (CA); H. Hung Pham, Brampton (CA); Vivian Z. Wang, North York (CA); Meilin Yang, Mississauga (CA)

(73) Assignee: Interface Biologics, Inc., Toronto (CA)

( * ) Notice: Subject to any disclaimer, the term of this patent is extended or adjusted under 35 U.S.C. 154(b) by 0 days.

(21) Appl. No.: 15/373,138

(22) Filed: Dec. 8, 2016

(65) Prior Publication Data

US 2017/0340781 A1 Nov. 30, 2017

Related U.S. Application Data

(63) Continuation of application No. 12/681,757, filed as application No. PCT/CA2008/001761 on Oct. 2, 2008, now abandoned.

(60) Provisional application No. 60/997,929, filed on Oct. 5, 2007.

(51) Int. Cl.
| | | |
|---|---|---|
| A61L 31/10 | (2006.01) |
| C09D 175/16 | (2006.01) |
| A61L 31/04 | (2006.01) |
| C09D 167/07 | (2006.01) |
| C08G 18/10 | (2006.01) |
| C08J 5/18 | (2006.01) |
| C08G 63/06 | (2006.01) |
| C08G 18/28 | (2006.01) |
| C08G 18/48 | (2006.01) |
| C08G 18/67 | (2006.01) |
| C08G 18/77 | (2006.01) |
| C08G 63/91 | (2006.01) |
| C09D 167/04 | (2006.01) |

(52) U.S. Cl.
CPC .............. *A61L 31/10* (2013.01); *A61L 31/04* (2013.01); *C08G 18/10* (2013.01); *C08G 18/2885* (2013.01); *C08G 18/4854* (2013.01); *C08G 18/672* (2013.01); *C08G 18/771* (2013.01); *C08G 63/06* (2013.01); *C08G 63/912* (2013.01); *C08J 5/18* (2013.01); *C09D 167/04* (2013.01); *C09D 167/07* (2013.01); *C09D 175/16* (2013.01); *C08J 2367/04* (2013.01); *C08J 2367/07* (2013.01); *C08J 2371/02* (2013.01)

(58) Field of Classification Search
CPC ......... A61L 31/04; A61L 31/10; C08G 18/10; C08G 18/2885; C08G 18/4854; C08G 18/672; C08G 18/771; C08G 63/06; C08G 63/91

See application file for complete search history.

(56) References Cited

U.S. PATENT DOCUMENTS

| | | | |
|---|---|---|---|
| 8,900,603 B2 | 12/2014 | Esfand et al. | |
| 2003/0097120 A1* | 5/2003 | Santerre | ............. A61L 33/0017 604/891.1 |
| 2003/0171804 A1 | 9/2003 | Krause | |
| 2011/0104228 A1 | 5/2011 | Esfand et al. | |
| 2015/0283304 A1 | 10/2015 | Esfand et al. | |

FOREIGN PATENT DOCUMENTS

| | | |
|---|---|---|
| CA | 1265296 A | 1/1990 |
| CA | 2030800 A1 | 12/1990 |
| CA | 2031186 A1 | 12/1990 |
| CA | 2074872 A1 | 2/1993 |
| CA | 2228505 A1 | 2/1997 |
| CA | 2297872 A1 | 8/2000 |
| CA | 2365460 A1 | 10/2000 |
| CA | 2425753 A1 | 4/2002 |
| CA | 2462529 A1 | 12/2002 |
| CA | 2489987 A1 | 12/2003 |
| CA | 2604696 A1 | 1/2007 |
| JP | 04-332760 A | 11/1992 |
| JP | 05-255496 A | 10/1993 |
| JP | 09-281346 A | 10/1997 |
| JP | H11-171929 A | 6/1999 |
| JP | 2002-504938 A | 2/2002 |
| JP | 2002-194031 A | 7/2002 |
| JP | 2005-530842 A | 10/2005 |
| WO | WO-90/15042 A2 | 12/1990 |
| WO | WO-96/31546 A1 | 10/1996 |
| WO | WO-96/31547 A1 | 10/1996 |
| WO | WO-98/51725 A1 | 11/1998 |
| WO | WO-02/098477 A2 | 12/2002 |
| WO | WO-2004/000288 A1 | 12/2003 |

OTHER PUBLICATIONS

Fischell, "Polymer coatings for stents. Can we judge a stent by its cover?" <http://circ.ahajournals.org/content/94/7/1494.full>, retrieved on May 1, 2014. Circulation. 94(7):1494-5 (1996) (4 pages).
Muh et al., "Lysineurethanedimethacrylate—a novel generation of amino acid based monomers for bone cements and tissue repair," Biomaterials. 23(14):2849-54 (2002).
Puskas et al., "Drug-eluting stent coatings," Wiley Interdiscip Rev Nanomed Nanobiotechnol. 1(4):451-62 (2009) (12 pages).
Sharifpoor et al., "Synthesis and characterization of degradable polar hydrophobic ionic polyurethane scaffolds for vascular tissue engineering applications," Biomacromolecules. 10(10):2729-39 (2009).
Verweire et al., "Evaluation of fluorinated polymers as coronary stent coating," J Mater Sci Mater Med. 11(4):207-12 (2000).
English Translation of Office Action in Japanese Application No. 2010-527308, dated Dec. 17, 2013 (5 pages).
International Preliminary Report on Patentability from International Application No. PCT/CA2008/001761, dated Apr. 7, 2010 (10 pages).

(Continued)

*Primary Examiner* — Anna Falkowitz
(74) *Attorney, Agent, or Firm* — Clark & Elbing LLP

(57) ABSTRACT

The invention features oligofluorinated cross-linked polymers and their use in the manufacture of articles and coating surfaces.

23 Claims, 7 Drawing Sheets

(56) References Cited

OTHER PUBLICATIONS

International Search Report from International Application No. PCT/CA2008/001761, dated Jan. 14, 2009 (8 pages).
Office Action for Canadian Application No. 2,701,186, dated Jul. 6, 2015 (5 pages).
Office Action in Canadian Patent Application No. 2,701,186, dated Oct. 14, 2014 (3 pages).
Office Action in European Patent Application No. 08 834 995.6, dated Nov. 5, 2014 (4 pages).
Office Action for Japanese Patent Application No. 2010-527308, dated Feb. 19, 2013 (10 pages).
Supplementary European Search Report for European Patent Application No. 08 83 4995, dated Nov. 20, 2012 (9 pages).
Written Opinion from International Application No. PCT/CA2008/001761, dated Jan. 14, 2009 (8 pages).

* cited by examiner

OLIGOFLUORINATED CROSS-LINKED POLYMERS AND USES THEREOF

BACKGROUND OF THE INVENTION

The invention features oligofluorinated cross-linked polymers. Once cured, the oligofluorinated cross-linked polymers are useful as a base polymer in the manufacture of articles or as a fluorinated coating.

Polymeric materials have been widely used for the manufacturing of medical devices, such as artificial organs, implants, medical devices, vascular prostheses, blood pumps, artificial kidneys, heart valves, pacemaker lead wire insulation, intra-aortic balloons, artificial hearts, dialyzers and plasma separators, among others. The polymer used within a medical device must be biocompatible (e.g., must not produce toxic, allergic, inflammatory reactions, or other adverse reactions). It is the physical, chemical and biological processes at the interface, between the biological system and the synthetic materials used, which defines the short- and long-term potential applications of a particular device.

In general, the exact profile of biocompatibility, biodegradation and physical stability, including chemical and physical/mechanical properties i.e., elasticity, stress, ductility, toughness, time dependent deformation, strength, fatigue, hardness, wear resistance, and transparency for a biomaterial are extremely variable. A wide variety of polymers (including polycondensates, polyolefins, polyvinyls, polypeptides, and polysaccharides, among others) have been employed in the manufacture of biomedical devices, drug delivery vehicles, and affinity chromatography systems. Polymers are selected for the characteristics that make them useful in any given application.

Fluoropolymers are generally hydrolytically stable and are resistant to destructive chemical environments. In addition they are biocompatible and have been used as components of medical devices. The combination of chemical inertness, low surface energy, antifouling properties, hydrophobicity, thermal and oxidative stability have enabled a great diversity of application for these materials. Fluoropolymers have been prepared from tetrafluoroethylene, via chain growth polymerization reactions, and other fluorinated derivatives, via step growth polymerization reactions producing infinite network fluoropolymers. A challenge for the use of these polymers in certain applications is the processing limitation of working with solid material including, (e.g., fluorinated polyetherurethanes, made from polyether glycols, isocyanates, chain extenders and non-fluorinated polyols) rather than fluids, of which the latter are easily applied into molds or onto surfaces. The problem is even more difficult and almost impossible to manage when the above needs to be cross linked for specific applications. The demand and need for practical fluoropolymers with specific chemical and physical properties has directed the molecular design and development of new fluorinated monomers There exists a need for co-polymer systems, which can be designed to provide the above characteristics that are needed for a variety of applications, including those in the biomedical field.

SUMMARY OF THE INVENTION

The invention features oligofluorinated cross-linked polymers. Once cured, the oligofluorinated cross-linked polymer is useful as a base polymer in the manufacture of articles or as an oligofluorinated coating. The coatings of the invention can also be used to encapsulate therapeutic agents.

Accordingly, in a first aspect the invention features a monomer including (i) two or more cross-linking domains, and (ii) an oligomeric segment having a first end covalently tethered to a first cross-linking domain and a second end covalently tethered to a second cross-linking domain, wherein at least one of the cross-linking domains is an oligofluorinated cross-linking domain.

In certain embodiments, the monomer is further described by formula (I):

$$(D)\text{-}[(oligo)\text{-}(D)]_n \quad (I)$$

In formula (I) oligo is an oligomeric segment; each D is a cross-linking domain; and n is an integer from 1 to 20, 1 to 15, 1 to 10, 1 to 8, or even 1 to 5, and wherein at least one D is an oligofluorinated cross-linking domain.

In other embodiments, the monomer is further described by formula (II):

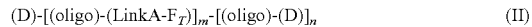

$$(D)\text{-}[(oligo)\text{-}(LinkA\text{-}F_T)]_m\text{-}[(oligo)\text{-}(D)]_n \quad (II)$$

In formula (II) oligo is an oligomeric segment; each D is a cross-linking domain; $F_T$ is an oligofluoro group; each LinkA-$F_T$ is an organic moiety covalently bound to a first oligo, a second oligo, and $F_T$; n is an integer from 1 to 20; and m is an integer from 1 to 20, wherein at least one D is an oligofluorinated cross-linking domain.

Cross-linking domains which can be used in the compositions of the invention include a reactive moiety that capable of chain growth polymerization, such as, without limitation, vinyls, epoxides, aziridines, and oxazolines.

In still other embodiments, the oligofluorinated cross-linking domain is selected from

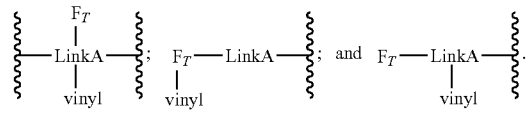

In certain embodiments, the monomer is further described by formula (III):

$$(oligo)_n(vinyl)_m(F_T)_o \quad (III)$$

In formula (III) oligo is an oligomeric segment; vinyl is a cross-linking domain including an unsaturated moiety capable of undergoing radical initiated polymerization; $F_T$ is an oligofluoro group covalently tethered to the vinyl and/or the oligo; and each of n, m, and o is, independently, an integer from 1 to 5, wherein the monomer includes at least one oligofluorinated cross-linking domain. The monomer of formula (III) may further be described by formula (IV):

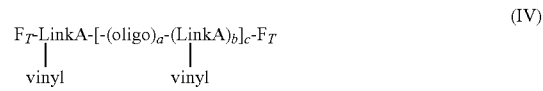

$$F_T\text{-}LinkA\text{-}[\text{-}(oligo)_a\text{-}(LinkA)_b]_c\text{-}F_T \quad (IV)$$
$$\quad\quad\quad\quad | \quad\quad\quad\quad\quad |$$
$$\quad\quad\quad\text{vinyl} \quad\quad\quad\text{vinyl}$$

In formula (IV) oligo is an oligomeric segment; vinyl is a cross-linking domain including an unsaturated moiety capable of undergoing radical initiated polymerization; $F_T$ is an oligofluoro group; each LinkA is, independently, an organic moiety covalently bound to oligo, $F_T$, and vinyl; and a, b, and c are integers greater than 0.

In certain embodiments, the monomers of the invention include one or more biologically active agents covalently tethered to the monomer.

In a related aspect, the invention features a method for coating an article by (a) contacting the article with a monomer of the invention and (b) polymerizing the monomer to form a cross-linked coating.

In another aspect the invention features a method for making a shaped article by (a) polymerizing a monomer of the invention to form a base polymer and (b) shaping the base polymer to form a shaped article.

In certain embodiments, the shaped article is an implantable medical device, such as, without limitation, cardiac-assist devices, catheters, stents, prosthetic implants, artificial sphincters, or drug delivery devices. In other embodiments the shaped article is a nonimplantable medical device.

The polymerization step resulting in an oligofluorinated cross-linked polymer of the invention can be initiated, for example, using heat, UV radiation, a photoinitiator, or a free-radical initiator. Desirably, the polymerization is initiated by heat.

In certain embodiments, the step of polymerizing further includes mixing the monomer of the invention with a second compound containing a vinyl group. The second compound can be another monomer of the invention or a nonfluorinated vinyl compound, such as acrylic acid, methyl acrylate, ethyl acrylate, n-butyl acrylate, 2-hydroxyethyl acrylate, n-butyl acrylate, glycidyl acrylate, vinyl acrylate, allyl acrylate, 2-hydroxyethyl acrylate, 2-hydroxy ethyl methacrylate (HEMA), 2-amino ethyl methacrylate, glycerol monomethacrylate, acrylamide, methacrylamide, N-(3-aminopropyl) methacrylamide, crotonamide, allyl alcohol, or 1,1,1-trimethylpropane monoallyl ether.

The invention also features a method for encapsulating a biologically active agent in a polymer by (a) contacting a biologically active agent with a monomer of the invention and (b) polymerizing the monomer to form an oligofluorinated cross-linked polymer.

The invention further features a composition including: (i) a first component having a core substituted with m nucleophilic groups, where m≥2; and a second component having a core substituted with n electrophilic groups, where n≥2 and m+n>4; wherein the composition includes at least one oligofluorinated nucleophilic group or one oligofluorinated electrophilic group, and wherein the first component and the second component react to form oligofluorinated cross-linked polymer.

In certain embodiments, the first component includes an oligomeric segment having a first end covalently tethered to a first nucleophilic group and a second end covalently tethered to a second nucleophilic group, wherein the first nucleophilic group or the second nucleophilic group is an oligofluorinated nucleophilic group. In other embodiments, the second component includes an oligomeric segment having a first end covalently tethered to a first electrophilic group and a second end covalently tethered to a second electrophilic group, wherein the first electrophilic group or the second electrophilic group is an oligofluorinated electrophilic group.

In still other embodiments, the first component or the second component is further described by formula (V):

(G)-[(oligo)-(G)]<sub>n</sub>     (V)

In formula (V) oligo is an oligomeric segment; G is either a nucleophilic group or an electrophilic group; and n is an integer from 1 to 5, wherein at least one G is an oligofluorinated nucleophilic group or oligofluorinated electroophilic group.

In another embodiment, the first component or the second component is further described by formula (VI):

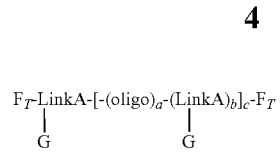
(VI)

In formula (VI) oligo is an oligomeric segment; G is either a nucleophilic group or an electrophilic group; $F_T$ is an oligofluoro group; each LinkA is, independently, an organic moiety covalently bound to oligo, $F_T$, and G; and a, b, and c are integers greater than 0.

In the above aspect, the nucleophilic groups and the electrophilic groups undergo a nucleophilic substitution reaction, a nucleophilic addition reaction, or both upon mixing. The nucleophilic groups can be selected from, without limitation, primary amines, secondary amines, thiols, alcohols, and phenols. The electrophilic groups can be selected from, without limitation, carboxylic acid esters, acid chloride groups, anhydrides, isocyanato, thioisocyanato, epoxides, activated hydroxyl groups, succinimidyl ester, sulfosuccinimidyl ester, maleimido, and ethenesulfonyl. Desirably, the number of nucleophilic groups in the mixture is approximately equal to the number of electrophilic groups in the mixture (i.e., the ratio of moles of nucleophilic groups to moles of electrophilic groups is about 2:1 to 1:2, or even about 1:1).

In a related aspect, the invention features a method for coating a substrate by (a) contacting the substrate with a composition of the invention and (b) polymerizing the composition on the substrate to form a cross-linked coating.

The invention also features a method for making a shaped article by (a) polymerizing a composition of the invention to form a base polymer and (b) shaping the base polymer to form a shaped article.

In certain embodiments, the substrate is an implantable medical device, such as, without limitation, cardiac-assist devices, catheters, stents, prosthetic implants, artificial sphincters, or drug delivery devices. In other embodiments the shaped article is a nonimplantable medical device.

In any of the above methods or compositions, the oligofluoro groups can be selected from, without limitation, groups having the formula:

$CF_3(CF_2)_pX$, $(CF_3)_2CF(CF_2)_pX$, or $(CF_3)_3C(CF_2)_pX$, wherein X is selected from $CH_2CH_2-$, $(CH_2CH_2O)_n$, $CH_2CH(OD)CH_2O-$, $CH_2CH(CH_2OD)O-$, or D-; D is a moiety capable of chain growth polymerization; p is an integer between 2 and 20; and n is an integer between 1 and 10.

In any of the above methods or compositions, the vinyl group can be selected, without limitation, from methylacrylate, acrylate, allyl, vinylpyrrolidone, and styrene derivatives.

In any of the above methods or compositions, the oligo can be selected, without limitation, from polyurethane, polyurea, polyamides, polyaklylene oxide, polycarbonate, polyester, polylactone, polysilicone, polyethersulfone, polypeptide, polysaccharide, polysiloxane, polydimethylsiloxane, polypropylene oxide, polyethylene oxide, polytetramethyleneoxide, and combinations thereof.

In any of the above methods or compositions, the biologically active agent can be selected, without limitation, from proteins, peptides, carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, proteins, vitamins, lipids, and prodrugs thereof. The biologically active agent can be any biologically active agent described herein.

The invention also features a method for coating a stent including initiating a polymerization reaction on the surface of the stent to form a polymerized coating. In certain embodiments, the polymerized coating is a cross-linked polymer coating, such as an oligofluorinated cross-linked polymer coating. The polymerization reaction can be, for example, a chain growth polymerization reaction, a nucleophilic substitution reaction, or a nucleophilic addition reaction. In certain embodiments, the method includes (a) contacting the stent with a monomer of the invention or a composition of the invention; and (b) polymerizing the monomer or polymerizing the composition to form a cross-linked coating.

In any of the above methods, an uncoated implantable medical device can be coated to produce a coated implantable medical device, the coated implantable medical device having, upon implantation into an animal, reduced protein deposition, reduced fibrinogene deposition, reduced platelet deposition, or reduced inflammatory cell adhesion in comparison to the uncoated implantable medical device.

By "base polymer" is meant a polymer having a tensile strength of from about 350 to about 10,000 psi, elongation at break from about 5%, 25%, 100%, or 300% to about 1500%, an unsupported thickness of from about 5 to about 100 microns, and a supported thickness of from about 1 to about 100 microns.

By "biologically active agent" is meant a compound, be it naturally-occurring or artificially-derived, that is encapsulated in a oligofluorinated cross-linked polymer of the invention and which may be released and delivered to a specific site (e.g., the site at which a medical device is implanted). Biologically active agents may include, for example, peptides, proteins, synthetic organic molecules, naturally occurring organic molecules, nucleic acid molecules, and components thereof. Desirably, the biologically active agent is a compound useful for the therapeutic treatment of a plant or animal when delivered to a site of diseased tissue. Alternatively, the biologically active agent can be selected to impart non-therapeutic functionality to a surface. Such agents include, for example, pesticides, bactericides, fungicides, fragrances, and dyes.

As used herein, "covalently tethered" refers to moieties separated by one or more covalent bonds. For example, where an oligofluoro group is covalently tethered to a cross-linking domain, tethered includes the moieties separated by a single bond as well as both moieties separated by, for example, a LinkA segment to which both moieties are covalently attached.

As used herein, "LinkA" refers to a coupling segment capable of covalently linking a cross-linking domain, an oligo segment, and an oligofluoro group. Typically, LinkA molecules have molecular weights ranging from 40 to 700. Preferably the LinkA molecules are selected from the group of functionalized diamines, diisocyanates, disulfonic acids, dicarboxylic acids, diacid chlorides and dialdehydes, wherein the functionalized component has secondary functional chemistry that is accessed for chemical attachment of an oligofluoro group or a vinyl group. Such secondary groups include, for example, esters, carboxylic acid salts, sulfonic acid salts, phosphonic acid salts, thiols, vinyls and secondary amines. Terminal hydroxyls, amines or carboxylic acids on the oligo intermediates can react with diamines to form oligo-amides; react with diisocyanates to form oligo-urethanes, oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal or oligo-imines. It should be noted that in any of the above cases one of the functional groups of LinkA, e.g., primary groups of a diamine, could be substituted for another functional group such that the LinkA would be, e.g., a hetero functional molecule (such as with an amine and a carboxylic acid as the primary groups) having a primary and a secondary functional chemistry.

By "oligo" or "oligo segment" is meant a non-fluorinated relatively short length of a repeating unit or units, generally less than about 50 monomeric units and molecular weights less than 10,000, but preferably <5000, and most preferably between 50 and 5,000 Daltons or between 100 and 5,000 Daltons. Preferably, oligo is selected from the group consisting of polyurethane, polyurea, polyamides, polyalkylene oxide, polycarbonate, polyester, polylactone, polysilicone, polyethersulfone, polyolefin, polyvinyl, polypeptide, polysaccharide; and ether and amine linked segments thereof. Alternatively, the oligo segment is as small as ethylenediamine.

By "oligofluorinated nucleophilic group" is meant a nucleophile covalently tethered to an oligofluoro group and separated by fewer than 25, 22, 18, or even 15 covalent bonds. Nucleophiles that can be used in the methods and compositions of the invention include, without limitation, amines, and thiols.

By "oligofluorinated electrophilic group" is meant an electrophile covalently tethered to an oligofluoro group and separated by fewer than 25, 22, 18, or even 15 covalent bonds. Electrophiles that can be used in the methods and compositions of the invention include, without limitation, activated acids, epoxy groups, and isocyanates.

By "oligofluorinated cross-linking domain" is meant a cross-linking domain covalently tethered to an oligofluoro group and separated by fewer than 25, 22, 18, or even 15 covalent bonds. The oligofluorinated cross-linked polymers of the invention can be formed from a monomer which contains at least one oligofluorinated cross-linking domain.

By "oligofluorinated cross-linked polymer" is meant a cross-linked polymer including an oligomeric segment and pendant oligofluoro groups.

By "cross-linking domain" is meant a moiety capable of forming covalent linkages via chain growth polymerization reactions. Chain growth polymerization reactions are reactions in which unsaturated monomer molecules add on to a growing polymer chain one at a time, as provided in the following equation:

Cross-linking domains can be designed to undergo radical initiated chain polymerization (i.e., in the polymerization of vinyl groups to produce polyvinyl), cationic chain growth polymerization reactions (i.e., cationic ring-opening polymerization, such as in the polymerization of epoxides to produce polyethers, and oxazolines to produce acylated polyamines), and anionic chain growth polymerization reactions (i.e., anionic ring-opening polymerization, such as in the polymerization of epoxides to produce polyethers, and N-methanesulfonyl-2-methylaziridine to produce polyamines).

By "vinyl monomer" is meant an oligo segment covalently tethered to two or more vinyl groups capable of undergoing radical initiated polymerization, wherein at least one vinyl group is contained within an oligofluorinated cross-linking domain.

Other features and advantages of the invention will be apparent from the following Detailed Description, the Drawings, and the Claims.

DETAILED DESCRIPTION

Figure 1:
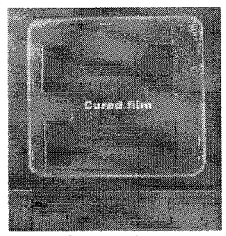
FIG. 1 is an image of a UV cured film of Compound 2, with tensile testing articles punched out, showing Compound 2 processing capability.

The invention features oligofluorinated cross-linked polymers. Once cured, the oligofluorinated cross-linked polymer is useful as a base polymer in the manufacture of articles or as an oligofluorinated coating. In certain embodiments, the oligofluorinated cross-linked polymer is formed from a combination of both chain growth and step growth polymerization reactions. The coatings of the invention can also be used to encapsulate therapeutic agents.

The oligofluorinated cross-linked polymers of the invention can be produced via chain growth polymerization reactions, nucleophilic substitution reactions, and/or a nucleophilic addition reactions. Regardless of how the oligofluorinated cross-linked polymer is produced, the resulting polymer will include pendant oligofluoro groups, an oligomeric segment, and, optionally, LinkA groups (used to covalently tether the various components together).

The quality and performance of the oligofluorinated cross-linked polymers can be varied depending upon the chemical composition and cured characteristics of polymerization step. Desirably, the precursor monomers materials exhibit high reactivity, resulting in efficient curing and fast curing kinetics. The oligofluorinated cross-linked polymers of the invention can be designed to result in a wide variety of desired mechanical properties, release profiles (where a biologically active agent is incorporated), and reduced protein and cell interactions (e.g., when used for in vivo applications). In part, this task entails and defines the formation of a three dimensional network. As shown in the examples, the properties can vary with chemical composition of the oligofluorinated precursor (e.g., altering the oligo segment or the positioning of the cross linking domain within) and with the polymerization conditions (e.g., by the inclusion of additives, or altering the concentration of the oligofluorinated precursor, to alter the cross-linking density). The extent to which the properties of the oligofluorinated cross-linked polymer can be controlled is one of the advantages of the invention.

Oligofluoro Groups

The monomers of the invention include at least one oligofluoro group. Typically, the oligofluoro group ($F_T$) has a molecular weight ranging from 100 to 1,500 and is incorporated into the oligomers of the invention by reaction of the corresponding perfluoroalkyl group with LinkA moiety. Desirably, $F_T$ is selected from a group consisting of radicals of the general formula: $CF_3(CF_2)_pCH_2CH_2$, $(CF_3)_2CF(CF_2)_pCH_2CH_2$, or $(CF_3)_3C(CF_2)_pCH_2CH_2$, wherein p is 2-20, preferably 2-8, and $CF_3(CF_2)_m(CH_2CH_2O)_n$, $(CF_3)_2CF(CF_2)_m(CH_2CH_2O)_n$, or $(CF_3)_3C(CF_2)_m(CH_2CH_2O)_n$, wherein n is 1-10 and m is 1-20, preferably 1-8. $F_T$ can be incorporated into a monomer by reaction of an oligofluorinated alcohol with LinkA or an oligo segment. $F_T$ typically includes a single fluoro-tail, but are not limited to this feature. A general formula for the oligomeric fluoro-alcohol of use in the invention is $H-(OCH_2CH_2)_n-(CF_2)_m-CF_3$, wherein n can range from 1 to 10, but preferably ranges from 1 to 4, and m can range from 1 to 20, but preferably ranges from 1-8. A general guide for the selection of n relative to m is that m should be equal to or greater than 2n in order to minimize the likelihood of the $(OCH_2CH_2)_n$ segment displacing the $(CF_2)_m-CF_3$ from the surface following exposure to water, since the former is more hydrophilic than the fluoro-tail and will compete with the fluoro-tail for surface dominance in the polymerized form. The presence of the $(OCH_2CH_2)_n$ segment is believed to have an important function within the oligofluoro domain, as it provides a highly mobile spacer segment between the fluoro-tail and the substrate. This spacer effectively exposes the oligofluorinated surface to, for example, an aqueous medium.

Examples of oligofluoro groups that incorporate reactive moieties for undergoing cross-linking are provided in Table 1. The examples provided include vinyl groups for undergoing chain growth polymerizations. Similar oligofluoro groups incorporating nucleophiles or electrophiles can be prepared for use in the preparation of oligofluorinated cross-linked polymers made via nucleophilic substitution reactions, and/or a nucleophilic addition reactions.

TABLE 1

| Structure | Description |
|---|---|
| $CH_2=CH-C(=O)-O-CH_2-CH(OH)-CH_2-(CF_2)_nCF_3$ | Perfluoro-2-hydroxy acrylates (generic class, various perfluoro) (FEO1) |
| $CH_2=CH-C(=O)-O-CH_2-CH(OH)-CH_2-(CF_2)_n-CF(CF_3)-CF_3$ | Perfluoro-2-hydroxy-trifluoromethyl acrylates (generic class, various perfluoro) |
| $CH_2=C(CH_3)-C(=O)-O-CH_2-CH(OH)-CH_2-(CF_2)_nCF_3$ | Perfluoro-2-hydroxy methacrylates (generic class, various perfluoro) |
| $CH_2=C(CH_3)-C(=O)-O-CH_2-CH(OH)-CH_2-(CF_2)_n-CF(CF_3)-CF_3$ | Perfluoro-2-hydroxy-trifluoromethyl methacrylates (generic class, various perfluoro) (FEO3) |
| $F_3C-(CF_2)_n-\equiv-CH_2-OH$ | Perfluoren-1-ol (generic class, various perfluoro) (FEO2) |
| $F_3C-(CF_2)_n-\equiv-(CH_2)_n-OH$ | Perfluoren-1-ol with longer $CH_2$ chains (generic class, various perfluoro) |

Oligomeric Segment

The monomers of the invention include at least one oligomeric segment. The oligo segment is covalently tethered to two or more cross-linking domains and at least one oligofluoro group. Oligo segments can include, for example, polytetramethylene oxide, polycarbonate, polysiloxane, polypropylene oxide, polyethylene oxide, polyamide, polysaccharide, or any other oligomeric chain. The oligo segment can include two or more hydroxyls, thiols, carboxylic acids, diacid chlorides or amides for coupling with LinkA, a cross-linking domain, and/or an oligofluoro group. Useful oligo segments include, without limitation, linear diamine or diol derivatives of polycarbonate, polysiloxanes, polydimethylsiloxanes; polyethylene-butylene co-polymers; polybutadienes; polyesters; polyurethane/sulfone co-polymers; polyurethanes, polyamides including oligopeptides (polyalanine, polyglycine or copolymers of amino-acids) and polyureas; polyalkylene oxides and specifically polypropylene oxide, polyethylene oxide and polytetramethylene oxide. The average molecular weight of the oligo segment can vary from 50 to 5,000 or 100 to 5,000, but in certain embodiments is less than 2,500 Daltons. Oligomeric components can be relatively short in length in terms of the repeating unit or units, and are generally less than 20 monomeric units.

LinkA

The monomers of the invention optionally include one or more LinkA groups. Typically, LinkA groups have molecular weights ranging from 40 to 700 Da and have multiple functionality in order to permit coupling of oligo segments, $F_T$, and/or cross-linking domains. Examples of LinkA groups include, without limitation, lysine diisocyanato esters (e.g., lysine diisocyanato methyl ester); 2,5-diaminobenzenesulfonic acid; 4,4'diamino 2,2'-biphenyl disulfonic acid; 1,3-diamino 2-hydroxypropane; and N-(2-aminoethyl)-3-aminopropane sulfonate.

Cross-Linking Domains

Cross-linking domains can be selected from a variety of different moieties which can undergo chain growth polymerizations. For example, cross-linking domains can be designed to undergo radical initiated chain polymerization (i.e., in the polymerization of vinyl groups to produce polyvinyl), cationic chain growth polymerization reactions (i.e., cationic ring-opening polymerization, such as in the polymerization of epoxides to produce polyethers, and oxazolines to produce acylated polyamines), and anionic chain growth polymerization reactions (i.e., anionic ring-opening polymerization, such as in the polymerization of epoxides to produce polyethers, and N-methanesulfonyl-2-methylaziridine to produce polyamines). Many different chain growth polymerization approaches are known in the art and can be included in the methods and compositions of the invention.

The oligofluorinated cross-linked polymers of the invention can be formed from a monomer which contains at least one oligofluorinated cross-linking domain. For example, such monomers can include at least one pendant oligofluoro chain ($F_T$) located adjacent to a step growth resultant functional group (urethane, urea, amide, ester, etc.) within LinkA, or an oligo segment, and at least two unreacted pendant cross-linking domains. The cross-linking domains and $F_T$ can be covalently tethered to a non-fluorinated oligo segment via LinkA, or $F_T$ can be directly tethered to a cross-linking domain and, together, covalently linked to the oligo segment via LinkA. Both LinkA and the oligo segment may designed to provide for a defined spatial distribution of $F_T$ groups, where more than one $F_T$ group is present in the monomer. This distribution simultaneously serves as a defining parameter, dictating the modulus, protein and cell interactions, and biochemical stability of the final polymer.

In certain embodiments, the monomer of the invention includes at least two vinyl groups. The vinyl groups are derivatized to include at least one functional group (e.g., a carboxylic acid, hydroxyl, amine, or thiol group), which is used to covalently tether the vinyl group to a biologically active agent, LinkA, and/or oligo. Vinyl groups useful in the methods and compositions of the invention include, without limitation, methacrylate, acrylate, cyclic or linear vinyl moieties, and allyl and styrene containing moieties, and typically have molecular weights ranging from 40 to 2000.

Oligofluorinated Nucleophilic and Electrophilic Groups

In invention provides a composition is provided that contains at least two components having reactive groups thereon, with the functional groups selected so as to enable reaction between the components, i.e., crosslinking to form an oligofluorinated cross-linked polymer. Each component has a core substituted with reactive groups. Typically, the composition will contain a first component having a core substituted with nucleophilic groups and a second component having a core substituted with electrophilic groups. The composition includes at least one oligofluorinated nucleophilic group or at least one oligofluorinated electrophilic group.

In order for a cross-linked polymer to be formed, there is preferably plurality of reactive groups present in each of the first and second components. For example, one component may have a core substituted with m nucleophilic groups, where m≥2, and the other component has a core substituted with n electrophilic groups, where n≥2 and m+n>4.

The reactive groups are electrophilic and nucleophilic groups, which undergo a nucleophilic substitution reaction, a nucleophilic addition reaction, or both. The term "electrophilic" refers to a reactive group that is susceptible to nucleophilic attack, i.e., susceptible to reaction with an incoming nucleophilic group. Electrophilic groups herein are positively charged or electron-deficient, typically electron-deficient. The term "nucleophilic" refers to a reactive group that is electron rich, has an unshared pair of electrons acting as a reactive site, and reacts with a positively charged or electron-deficient site.

Examples of nucleophilic groups suitable for use in the invention include, without limitation, primary amines, secondary amines, thiols, phenols, and alcohols. Certain nucleophilic groups must be activated with a base so as to be capable of reaction with an electrophilic group. For example, when there are nucleophilic sulfhydryl and hydroxyl groups in the multifunctional compound, the compound must be admixed with an aqueous base in order to remove a proton and provide a thiolate or hydroxylate anion to enable reaction with the electrophilic group. Unless it is desirable for the base to participate in the reaction, a non-nucleophilic base is preferred. In some embodiments, the base may be present as a component of a buffer solution.

The selection of electrophilic groups provided on the multifunctional compound, must be made so that reaction is possible with the specific nucleophilic groups. Thus, when the X reactive groups are amino groups, the Y groups are selected so as to react with amino groups. Analogously, when the X reactive groups are sulfhydryl moieties, the corresponding electrophilic groups are sulfhydryl-reactive groups, and the like. Examples of electrophilic groups suitable for use in the invention include, without limitation, carboxylic acid esters, acid chloride groups, anhydrides, isocyanato, thioisocyanato, epoxides, activated hydroxyl groups, succinimidyl ester, sulfosuccinimidyl ester, maleimido, and ethenesulfonyl. Carboxylic acid groups typically must be activated so as to be reactive with a nucleophile. Activation may be accomplished in a variety of ways, but often involves reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxysuccinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction.

In general, the concentration of each of the components will be in the range of about 1 to 50 wt %, generally about 2 to 40 wt %. The preferred concentration will depend on a number of factors, including the type of component (i.e., type of molecular core and reactive groups), its molecular weight, and the end use of the resulting three-dimensional matrix. For example, use of higher concentrations of the components, or using highly functionalized components, will result in the formation of a more tightly crosslinked network, producing a stiffer, more robust composition, such as for example a gel. In general, the mechanical properties of the three-dimensional matrix should be similar to the mechanical properties of the surface to which the matrix (or matrix-forming components) will be applied. Thus, when the matrix will be used for an orthopedic application, the gel matrix should be relatively firm, e.g., a firm gel; however, when the matrix will be used on soft tissue, as for example in tissue augmentation, the gel matrix should be relatively soft, e.g., a soft gel.

Further details of the formation of oligofluorinated cross-linked polymers is provided in the Examples.

Substrates which can be coated using the methods and compositions of the invention include, without limitation, wood, metals, ceramics, plastics, stainless steels, fibers, and glasses, among others.

Synthesis

The oligofluorinated cross-linked polymers of the invention are synthesized from monomers which can be prepared, for example, as described in Schemes 1-4 below. In Schemes 1-4, oligo is an oligomeric segment, LinkA is a linking element as defined herein, Bio is a biologically active agent, $F_T$ is an oligofluoro group, and D is a moiety capable of undergoing a chain growth polymerization reaction, nucleophilic substitution reaction, and/or a nucleophilic addition reaction.

Scheme 1

$F_T$-LINK A-[-(oligo)$_a$-(LINK A)$_b$]$_c$-$F_T$ ⟶

+ D $F_T$-LINK A-[-(oligo)$_a$-(LINK A)$_b$]$_c$-$F_T$
|  |
D  D

Scheme 2

LINK A-[-(oligo)$_a$-(LINK A)$_b$]$_c$ ⟶
|  |
D  D

+ $F_T$ $F_T$-LINK A-[-(oligo)$_a$-(LINK A)$_b$]$_c$-$F_T$
|  |
D  D

Scheme 3

LINK A-[-(oligo)$_a$-(LINK A)$_b$]$_c$ ⟶

+ $F_T$(D)

$F_T$(D)-LINK A-[-(oligo)$_a$-(LINK A)$_b$]$_c$-$F_T$(D)

Scheme 4

LINK A-[-(oligo)$_a$-(LINK A)$_b$]$_c$ ⟶

+ Bio $F_T$(D)-LINK A-[-(oligo)$_a$-(LINK A)$_b$]$_c$-$F_T$(D)
|  |
Bio  Bio

The monomers can be synthesized, for example, using multi-functional LinkA groups, a multi-functional oligo segment, a mono-functional $F_T$ group, and cross-linking domains having at least one functional component that can be covalently tethered to the oligomeric segment.

The first step of the synthesis can be carried out by classical urethane/urea reactions using the desired combination of reagents. However, the order in which the various components are assembled can be varied for any particular monomer.

Further synthetic details are provided in the Examples.
Oligofluorinated Cross-Linked Polymerized Coatings The oligofluorinated cross-linked polymers of the invention can be used to form coatings which provide for the discrete distribution of mono-dispersed oligofluoro groups in a pendant arrangement on a surface that is stable (e.g., does not readily leach from the surface).

The coatings of the invention can be formed by polymerization of an oligofluorinated cross-linking domain, such as a vinyl monomer, or by reaction of a multifunctional nucleophile with an oligofluorinated electrophile or a multifunctional electrophile with an oligofluorinated nucleophile.

The coatings of the invention can impart high water repellency, low refractive index, soil resistance, reduce fouling, and improve biocompatibility. For blood dwelling devices the coatings can reduce the formation of blood clots at the device surface after implantation.

The monomer can be applied to a surface alone (e.g., as a liquid); in the presence of a diluent (e.g., acetone, methanol, ethanol, ethers, hexane, toluene, or tetrahydrofuran), in combination with an oligofluorinated precursor. Suitable methods for applying the monomer to a surface include, without limitation, spin coating, spraying, roll coating, dipping, brushing, and knife coating, among others.

Polymerization of the monomers of the invention can be achieved by UV radiation, electron beam, or thermal heat in the presence of a photoinitiator or free-radical thermal initiator, depending upon the nature of the reactive moiety employed. Many light energy sources can be used and a typical source is ultraviolet (UV) radiation. A typical UV lamp is a lamp equipped with a lamp output of 400 W/in (purchased from Honle UV America Inc.). The lamp is secured on top of a home-built box (26.5 cm length, 26.5 cm width and 23.0 cm height). The box is designed to control the curing environment, using either an air or nitrogen atmosphere.

A wide variety of articles can be coated using the compositions and methods of the invention. For example, articles which contact bodily fluids, such as medical devices can be coated to improve their biocompatibility. The medical devices include, without limitation, catheters, guide wires, vascular stents, micro-particles, electronic leads, probes, sensors, drug depots, transdermal patches, vascular patches, blood bags, and tubing. The medical device can be an implanted device, percutaneous device, or cutaneous device. Implanted devices include articles that are fully implanted in a patient, i.e., are completely internal. Percutaneous devices include items that penetrate the skin, thereby extending from outside the body into the body. Cutaneous devices are used superficially. Implanted devices include, without limitation, prostheses such as pacemakers, electrical leads such as pacing leads, defibrillators, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters or various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

The coating of an implantable medical device such as a vascular stent is of great interest. Stents are commonly used for the treatment of stenosis. Generally, stent is crimped onto a balloon catheter, inserted in the coronary vessel of blockage and the balloon is inflated causing the stent to expand to a desired diameter hence opening up the blocked artery vessel for blood flow. However, during this deployment process, damages to the artery wall can cause elastic recoil of the vessel wall which characterizes the early phase of restenosis. Stent coating offers a platform for the delivery of biologically active agents for controlling post deployment restenosis. Using the methods and compositions of the invention, drug delivery on the stent is achieved by formulating a solution with a polymer dissolved in a solvent, and a biologically active agent dispersed in the blend. When the solution is sprayed on the stent, the solvent is allowed to evaporate, leaving on the stent surface the polymer with the drug embedded in the polymer matrix. Alternatively, the biologically active agent is covalently bound to the oligofluorinated precursor prior to polymerization. The release of the biologically active agent covalently bound to the resulting oligofluorinated cross-linked polymer can be controlled by utilizing a degradable linker (e.g., a ester linkage) to attach the biologically active agent.

Alternatively, the coatings of the invention can be applied to wood for exterior applications (decks and fences), boats, ships, fabrics, electronic displays, gloves, and apparel.

One distinctive feature of the intercalative oligofluorinated cross-linked polymer is the ability to initiate the polymerization step on the device surface, producing a continuous polymer coating similar to skin wrap.

Shaped Articles

Articles can be formed from the oligofluorinated cross-linked polymers of the invention. For example, the oligofluorinated precursor can be combined with an initiator using reaction injection molding to produce a shaped article.

Any shaped article can be made using the compositions of the invention. For example, articles suitable for contact with bodily fluids, such as medical devices can be made using the compositions described herein. The duration of contact may be short, for example, as with surgical instruments or long term use articles such as implants. The medical devices include, without limitation, catheters, guide wires, vascular stents, micro-particles, electronic leads, probes, sensors, drug depots, transdermal patches, vascular patches, blood bags, and tubing. The medical device can be an implanted device, percutaneous device, or cutaneous device. Implanted devices include articles that are fully implanted in a patient, i.e., are completely internal. Percutaneous devices include items that penetrate the skin, thereby extending from outside the body into the body. Cutaneous devices are used superficially. Implanted devices include, without limitation, prostheses such as pacemakers, electrical leads such as pacing leads, defibrillators, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters or various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

Biologically Active Agents

Biologically active agents can be encapsulated within the coatings and articles of the invention. The encapsulation can be achieved either by coating the article to be treated with a biologically active agent prior to application and polymerization of the monomer, or by mixing the monomer and the biologically active agent together and applying the mixture to the surface of the article prior to polymerization. Biologically active agents include therapeutic, diagnostic, and prophylactic agents. They can be naturally occurring compounds, synthetic organic compounds, or inorganic compounds. Biologically active agents that can be used in the methods and compositions of the invention include, but are not limited to, proteins, peptides, carbohydrates, antibiotics, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogrel and ramatroban, antibodies, neurotransmitters, psychoactive drugs, oligonucleotides, proteins, lipids, and any biologically active agent described herein.

Exemplary therapeutic agents include growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formoterol, albuterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutytric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, fluclorinide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamin D, vitamin C, vitamin E, vitamin A, Vitamin U, vitamin L, vitamin K, pantothenic acid, aminophenylbutyric acid, penicillin, acyclovir, ofloxacin, amoxicillin, tobramycin, retrovir, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active agent can be an antiinflammatory agent, such as an NSAID, corticosteriod, or COX-2 inhibitor, e.g., rofecoxib, celecoxib, valdecoxib, or lumiracoxib.

Exemplary diagnostic agents include imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials.

A preferred biologically active agent is a substantially purified peptide or protein. Proteins are generally defined as consisting of 100 amino acid residues or more; peptides are less than 100 amino acid residues. Unless otherwise stated, the term protein, as used herein, refers to both proteins and peptides. The proteins may be produced, for example, by isolation from natural sources, recombinantly, or through peptide synthesis. Examples include growth hormones, such as human growth hormone and bovine growth hormone; enzymes, such as DNase, proteases, urate oxidase, alronidase, alpha galactosidase, and alpha glucosidase; antibodies, such as trastuzumab.

Rapamycin Macrolides

Rapamycin (Sirolimus) is an immunosuppressive lactam macrolide that is produced by *Streptomyces hygroscopicus*. See, for example, McAlpine, J. B., et al., *J. Antibiotics* 44: 688 (1991); Schreiber, S. L., et al., *J. Am. Chem. Soc.* 113: 7433 (1991); and U.S. Pat. No. 3,929,992, incorporated herein by reference. Exemplary rapamycin macrolides which can be used in the methods and compositions of the invention include, without limitation, rapamycin, CCI-779, Everolimus (also known as RAD001), and ABT-578. CCI-779 is an ester of rapamycin (42-ester with 3-hydroxy-2-hydroxymethyl-2-methylpropionic acid), disclosed in U.S. Pat. No. 5,362,718. Everolimus is an alkylated rapamycin (40-O-(2-hydroxyethyl)-rapamycin, disclosed in U.S. Pat. No. 5,665,772.

Antiproliferative Agents

Exemplary antiproliferative agents which can be used in the methods and compositions of the invention include, without limitation, mechlorethamine, cyclophosphamide, ifosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, flurouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™ (Novartis), leflunomide (Pharmacia), SU5416 (Pharmacia), SU6668 (Pharmacia), PTK787 (Novartis), Iressa™ (AstraZeneca), Tarceva™, (Oncogene Science), trastuzumab (Genentech), Erbitux™ (ImClone), PKI1166 (Novartis), GW2016 (GlaxoSmithKline), EKB-509 (Wyeth), EKB-569 (Wyeth), MDX-H210 (Medarex), 2C4 (Genentech), MDX-447 (Medarex), ABX-EGF (Abgenix), CI-1033 (Pfizer), Avastin™ (Genentech), IMC-1C11 (ImClone), ZD4190 (AstraZeneca), ZD6474 (AstraZeneca), CEP-701 (Cephalon), CEP-751 (Cephalon), MLN518 (Millenium), PKC412 (Novartis), 13-cis-retinoic acid, isotretinoin, retinyl palmitate, 4-(hydroxycarbophenyl) retinamide, misonidazole, nitracrine, mitoxantrone, hydroxyurea, L-asparaginase, interferon alfa, AP23573, Cerivastatin, Troglitazone, CRx-026DHA-paclitaxel, Taxoprexin, TPI-287, Sphingosine-based lipids, and mitotane.

Corticosteroids

Exemplary corticosteroids which can be used in the methods and compositions of the invention include, without limitation, 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, fluclorinide, flumethasone, flumethasone pivalate, flunisolide, fluocinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandrenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar anti-inflammatory properties are also intended to be encompassed by this group.

NSAIDs

Exemplary non-steroidal antiinflammatory drugs (NSAIDs) which can be used in the methods and compositions of the invention include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin.

Analgesics

Exemplary analgesics which can be used in the methods and compositions of the invention include, without limitation, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine and dihydroacetorphine.

Antimicrobials

Exemplary antimicrobials which can be used in the methods and compositions of the invention include, without limitation, penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

Local Anesthetics

Exemplary local anesthetics which can be used in the methods and compositions of the invention include, without limitation, cocaine, procaine, lidocaine, prilocaine, mepivicaine, bupivicaine, articaine, tetracaine, chloroprocaine, etidocaine, and ropavacaine.

Antispasmodic

Exemplary antispasmodics which can be used in the methods and compositions of the invention include, without limitation, atropine, belladonna, bentyl, cystospaz, detrol (tolterodine), dicyclomine, ditropan, donnatol, donnazyme, fasudil, flexeril, glycopyrrolate, homatropine, hyoscyamine, levsin, levsinex, librax, malcotran, novartin, oxyphencyclimine, oxybutynin, pamine, tolterodine, tiquizium, prozapine, and pinaverium.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

The following acronyms denote the listed compounds used in the preparation of the polymers, polymer complexes, and polymer conjugates described herein.

AEMA aminoethyl methacrylate
ALLYL allyl alcohol
ASA acetylsalicylic acid
BAL poly(difluoromethylene),α-fluoro-ω-(2-hydroxyethyl)
BHT butylated hydroxy toluene
BPO benzoyl peroxide
C8 1-octanol
$CDCl_3$ deuterated chloroform
DBDL dibutyltin dilaurate
DCM dichloromethane
DMAc dimethylacetamide
DMAP 4-(dimethyamino)pyridine
DMF dimethylformamide
DMSO dimethylsulphoxide
EDC 1-ethyl-3-(3-dimethylamino-propyl) carbodiimide-.HCl
EVA poly(ethylene-co-vinyl acetate)
FEO1 4,4,5,5,6,6,7,7,8,8,9,9,10,10,11,11 heptadecafluoro-2-hydroxyundecyl acrylate
FEO2 1 H, 1H, 2H, 3H nonafluorohept-2-en-ol
FEO3 3-(perfluoro-3-methylbutyl)-2-hydroxypropyl methacrylate
HEMA hydroxyethyl methacrylate
HCl hydrochloric acid
HMP 2-hydroxy-2-methylpropiophenone
KBr potassium bromide
LDI lysine diisocyanate
MAA methacrylic acid
MeOH methanol
$MgSO_4$ magnesium sulphate
MMA methyl methacrylate
NaOH sodium hydroxide
PBS phosphate buffer solution
PCL polycaprolactone
PSi polydimethylsiloxane-bis(3-aminopropyl) terminated
PTMO polytetramethylene oxide
PTX paclitaxel
SIBS poly(styrene-isobutylene-styrene)
TEA triethylamine
TEGMA triethylene glycol dimethacrylate
TFAc trifluoroacetic acid
THF tetrahydrofuran
VP 1-vinyl-2-pyrrolidone List of monomers: methacrylic acid, isobutyl acrylate, tertiarybutyl acrylate, tertiarybutyl methacrylate, 2-hydroxyethyl acrylate, 2-hydroxypropyl acrylate, butanediol monoacrylate, ethyldiglycol acrylate, lauryl acrylate, dimethylaminoethyl acrylate, dihydrodicyclopentadienyl acrylate, N-vinylformamid, cyclohexyl methacrylate, 2-isocyanotomethacrylate, glycidyl methacrylate, cyanoacrylate, isobornyl acrylate, 4-hydroxybutyl vinyl ether, di((meth) ethylene glycol) vinyl ether, maleic and fumaric acid, triethylene glycol dimethacrylate, 1,6 hexanediol methacrylate, 1,4 butanediol dimethacrylate, and urethane dimethacrylate.

List of initiators: 1,1'-Azobis(cyclohexanecarbonitrile), 2,2'-Azobisisobutyronitrile (AIBN), 2,2'-Azobis[2-(2-imidazolin-2-yl)propane]dihydrochloride, Tert-Butyl peracetate, 4,4-Azobis(4-cyanovaleric acid), 2,2'-Azobis[2-(2-imidazolin-2-yl)propane]dihydrochloride, 2,2'-Azobis[2-(2-imidazolin-2-yl)propane]disulfate dihydrate, 2,2'-Azobis(2-methylpropionamidine)dihydrochloride, 2,2'-Azobis[N-(2-carboxyethyl)-2-methylpropionamidine]hydrate, 2,2'-Azobis {2-[1-(2-hydroxyethyl)-2-imidazolin-2-yl] propane}dihydrochloride, 2 Peracetic acid, 2'-Azobis[2-(2-imidazolin-2-yl)propane], 2,2'-Azobis(1-imino-1-pyrrolidino-2-ethylpropane)dihydrochloride, 2,2'-Azobis {2-methyl-N-[1-bis(hydroxymethyl)-2-hydroxyethl]propionamide}, 2,2'-Azobis[2-methyl-N-(2-hydroxyethyl)propionamide], 2,2'-Azobis(4-methoxy-2.4-dimethyl valeronitrile), 2,2'-Azobis(2.4-dimethyl valeronitrile), Dimethyl 2,2'-azobis(2-methylpropionate), 2,2'-Azobis(2-methylbutyronitrile), 1,1'-Azobis(cyclohexane-1-carbonitrile), 2,2'-Azobis[N-(2-propenyl)-2-methylpropionamide], 1-[(1-cyano-1-methylethyl)azo]formamide, 2,2'-Azobis(N-butyl-2-methylpropionamide), 2,2'-Azobis(N-cyclohexyl-2-methylpropionamide), Tert-Amyl peroxybenzoate, Benzoyl peroxide, Potassium persulphate, 2,2-Bis(tert-butylperoxy) butane, 1,1-Bis(tert-butylperoxy)cyclohexane, 2,5-Bis(tert-butylperoxy)-2,5-dimethyl-3-hexyne, Bis(1-(tert-butylperoxy)-1-methylethyl)benzene, 1,1-Bis(tert-butylperox)-3,3,5-trimethylcyclohexane, Tert-butyl hydroperoxide, Tert-butyl peroxide, Cyclohexanone peroxide, 2,4-pentadione peroxide, Lauroyl peroxide, Dicumyl peroxide, Tert-butyl peroxybenzoate, Cumene hydroperoxide, Tert-butylperoxy isopropyl carbonate, Camphorquinone, Diphenyl(2,4,6-trimethylbenzoyl)phosphine oxide, 2-tert-Butylanthraquinone, 9,10-Phenanthrenequinone, Anthraquinone-2-sulfonic acid sodium salt monohydrate, Phenylbis(2,4,6-trimethylbenzoyl)phosphine oxide, 1-Hydroxycyclohexyl phenyl ketone, 2-Hydroxy-2-methylpropiophenone, 2-Benzyl-2-(dimethylamino)-4'-morpholinobutyrophenone, 2,2-Diethoxyacetophenone, 2-Hydroxy-4'-(2-hydroxyethoxy)-2-methylpropiophenone, 2-Methyl-4'-(methylthio)-2-morpholinopropiophenone, 3'-Hydroxyacetophenone, 4'-Ethoxyacetophenone, 4'-Hydroxyacetophenone, 4'-Phenoxyacetophenone, 4'-tert-Butyl-2',6'-dimethylacetophenone, Diphenyl(2,4,6-trimethylbenzoyl)phosphine oxide/2-hydroxy-2-methylpropiophenone, 2,2-Dimethoxy-2-phenylacetophenone, 4,4'-Dimethoxybenzoin, 3-Methylbenzophenone, Benzoin, 3-Hydroxybenzophenone, 3,4-Dimethylbenzophenone, 2-Methylbenzophenone, Benzophenone-3,3',4,4'-tetracarboxylic dianhydride, 4-Methylbenzophenone, 4-Hydroxybenzophenone, 4-Benzoylbiphenyl, 4-(Dimethylamino)benzophenone, 4-(Diethylamino)benzophenone, Michler's ketone, 4,4'-Bis [2-(1-propenyl)phenoxy]benzophenone, mixture of cis and trans 4,4'-Dihydroxybenzophenone, 4,4'-Bis(diethylamino)benzophenone, Methyl benzoylformate, Benzoin methyl ether, Benzoin isobutyl ether, 4,4'-Dimethylbenzil, Benzoin ethyl ether, (4-Bromophenyl)diphenylsulfonium triflate, (4-Chlorophenyl)diphenylsulfonium triflate, Triphenylsulfonium perfluoro-1-butanesufonate, N—Hydroxy-5-norbornene-2,3-dicarboximide perfluoro-1-butanesulfonate, Triphenylsulfonium triflate, Diphenyliodonium 9,10-dimethoxyanthracene-2-sulfonate, Tris(4-tert-butylphenyl) sulfonium perfluoro-1-butanesulfonate, and Tris(4-tert-butylphenyl) sulfonium triflate.

EXPERIMENTAL PROTOCOLS

Purification and analytical methods mentioned in the examples are described below.

Cationic Solid Phase Extraction (SCX-SPE): A pre-packed cationic silica gel column (plastic) is used to remove small cationic compounds from the reaction mixtures.

Fluorous Solid Phase Extraction (F-SPE): SPE substrates modified with perfluorinated ligands (F-SPE) are used to selectively retain perfluorinated oligomers, allowing the separation of non-fluorinated compounds.

Contact angle analysis: Droplets of MilliQ water are applied to films, and the shape of the droplets are analyzed using a Kruss DSA instrument.

Elemental analysis: samples are combusted, and the liberated fluorine is absorbed into water and analyzed by ion-selective electrode.

FTIR analysis: a sample is dissolved as a 20 mg/mL solution in a suitable volatile solvent and 50 µL of this solution is cast on a KBr disk. Once dried, the sample is analyzed.

Gel extraction: samples of film are weighed and then extracted with a suitable solvent for 12 hours. The films are removed from the solvent, weighed, and then vacuum dried and weighed again. Gel content is calculated as the percentage of mass that is not extracted. Swell ratio is calculated at the percentage increase in mass before the sample is vacuum dried.

GPC analysis: samples are dissolved as a 20 mg/mL solution in a suitable solvent (THF, dioxane, DMF) and are analyzed using a polystyrene column calibrated with polystyrene standards.

NMR: samples are dissolved at 20 mg/mL in a suitable solvent and are analyzed using a 300 or 400 MHz NMR spectrometer.

SEM: surfaces were coated with gold.

Tensile testing: films are cut into test specimens and are analyzed according to ASTM D 1708 guidelines.

XPS analysis: films are analyzed using a 90° take-off angle.

Example 1: Synthesis of α,ω-BAL-Poly(LDI(HEMA)/PTMO) with Pendent Vinyl Groups (Compound 2)

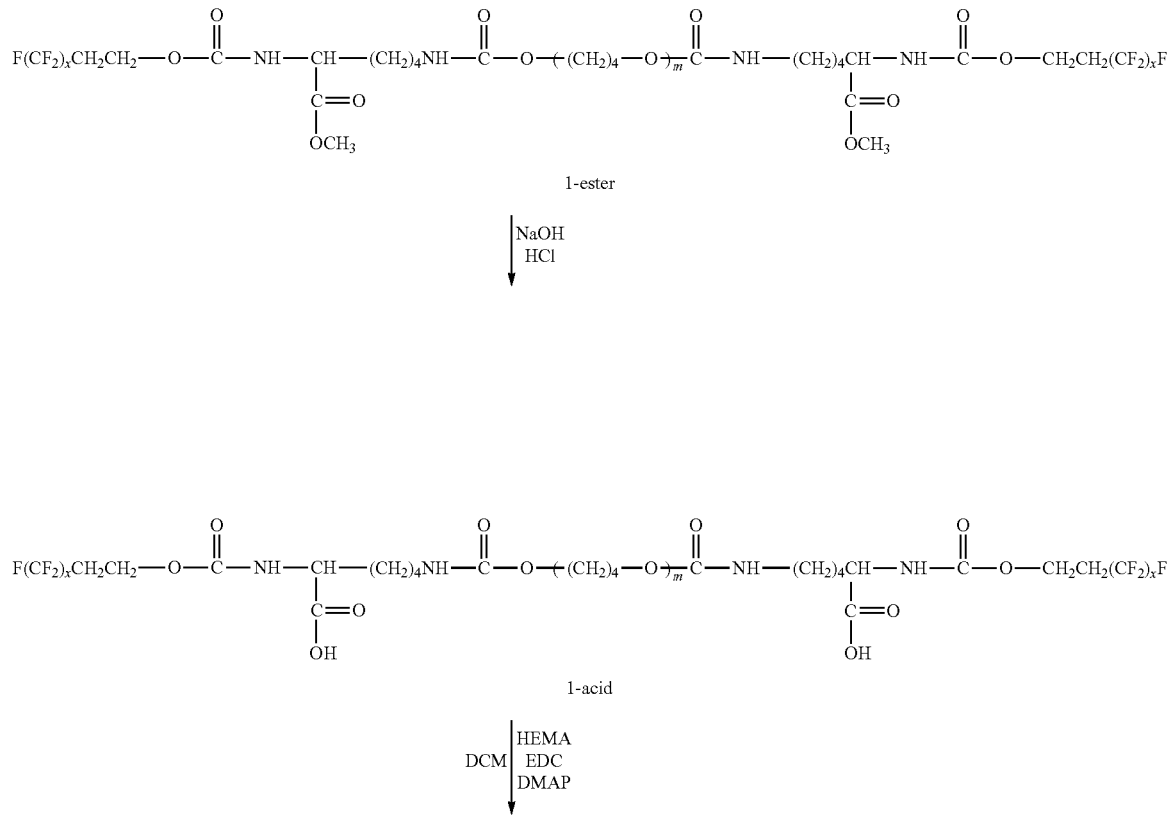

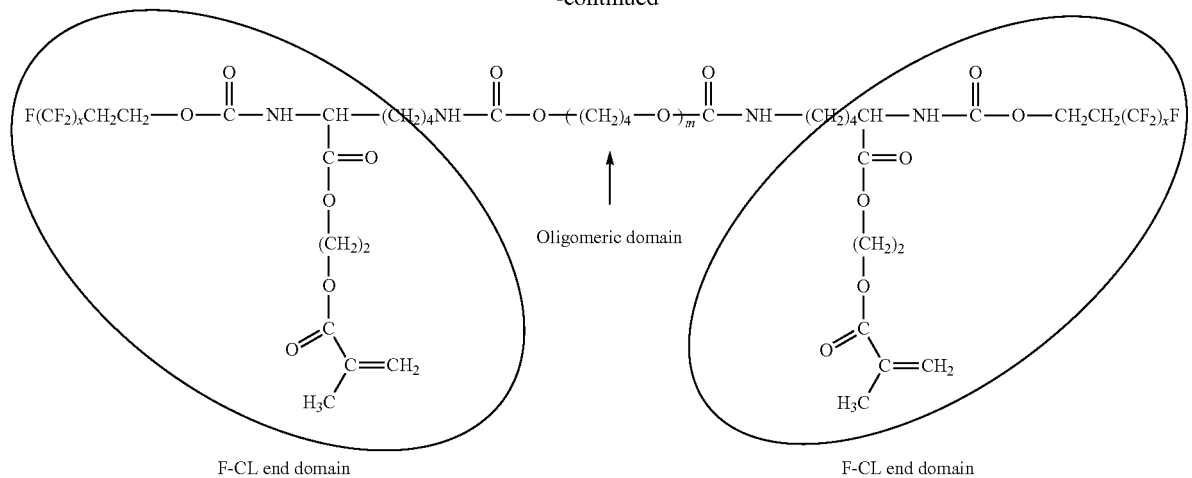

Polytetramethylene oxide (PTMO) (15 grams, 14 mmol) was weighed into a 500 mL 2-neck flask and degassed overnight at 30° C., and was then dissolved in anhydrous DMAc (40 mL) under $N_2$. LDI (5.894 g, 28 mmol) was weighed into a 2-neck flask and was dissolved in anhydrous DMAc (40 mL) under $N_2$. DBDL was added to the LDI solution, and this mixture was added dropwise to the PTMO solution. The flask was kept sealed and maintained under $N_2$ at 70° C. for two hours. Fluoroalcohol (13.151 g, 31 mmol) was weighed into a 2-neck flask and degassed at room temperature, was dissolved in anhydrous DMAc (40 mL) and was added dropwise to the reaction mixture. The reaction solution was sealed under $N_2$ and was stirred overnight at room temperature. The product was precipitated in water (3 L), washed several times, and dried. The product was dissolved in MeOH and the tin catalyst was extracted by SCX SPE. The final product (Compound 1-ester) was dried under vacuum. $^1$H NMR (300 MHz, $CDCl_3$) δ (ppm) 4.24-4.46 (—$CH_2$—O, BAL), 3.94-4.13 (—$CH_2$—O—CO PTMO), 3.74 ($CH_3$, LDI), 3.28-3.50 ($CH_2$—O PTMO), 2.98-3.28 (C$\underline{H}_2$—NH, LDI), 2.29-2.60 (—$CH_2$—$CF_2$—, BAL), 1.16-1.96 (PTMO and LDI $CH_2$). $^{19}$F NMR (300 MHz, $CDCl_3$) δ (ppm) −81.23 ($CF_3$), −114.02 ($CF_2$), −122.34 ($CF_2$), −123.34 ($CF_2$), −123.30 ($CF_2$), −124.03 ($CF_2$), −126.56 ($CF_2$). Elemental analysis: theoretical based on reagent stoichiometry (%): C, 48.49; H, 6.57; F, 23.85; N, 2.81; 0, 18.27. Measured: C, 48.70; H, 6.56; F, 22.81; N, 2.63. HPLC analysis (reversed phase, C18 column, methanol and pH 9 PBS mobile phase (gradient)): retention time of 39.5 minutes. DSC analysis: Tg=−66.6° C. IR analysis was in accordance with the chemical structure: 3327.29 $cm^{-1}$ ν(N—H) H-bonded, 2945.10 $cm^{-1}$ ν(C—H) $CH_2$ asymmetric stretching, 2865.69 $cm^{-1}$ ν(C—H) $CH_2$ symmetric stretching, 1717.91 $cm^{-1}$ν(C=O) urethane amide, 1533.54 $cm^{-1}$ ν(C—N) stretching mode, 1445.56 $cm^{-1}$ ν(C—N) stretching mode, 1349.31 $cm^{-1}$ ν(C—O) stretching, 1400-1000 $cm^{-1}$ ν(C—F) monofluoroalkanes absorb to the right in the range, while polyfluoroalkanes give multiple strong bands over the range from 1350-1100 $cm^{-1}$.

Compound 1-ester (15.0 g, ~16 mmol ester) was weighed into a flask, dissolved in MeOH (150 mL) and once dissolved, 1N NaOH solution (17 mL) was added dropwise. After six hours of stirring at room temperature, the solution was neutralized using 1N HCl (17.7 mL), and the product was precipitated in water, washed with water, and dried under vacuum at 60° C. The conversion of ester groups to acid functional groups was confirmed by NMR analysis. Proton NMR indicated the disappearance of methoxy groups at 3.75 ppm. $^{19}$F NMR (300 MHz, $CDCl_3$) δ (ppm) −81.23 ($CF_3$), −114.02 ($CF_2$), −122.34 ($CF_2$), −123.34 ($CF_2$), −123.30 ($CF_2$), −124.03 ($CF_2$), −126.56 ($CF_2$). HPLC analysis: retention time of 33.4 minutes (Compound 1-acid). Reversed phase HPLC, C18 column, MeOH and pH 9 PBS mobile phase (gradient). DSC analysis: Tg=−65° C. Elemental analysis: theoretical based on reagent stoichiometry (%): C, 47.96; H, 6.48; F, 24.19; N, 2.86; 0, 18.53. Measured: C, 46.92; H, 6.16; F, 26.43; N, 2.94. Compound 1-acid (10.0 gram, ~8 mmol acid), DMAP (0.488 gram, 4 mmol), HEMA (6.247 gram, 48 mmol) and DCM (50 mL) were added to a 250 mL flask, and stirred until all compounds were dissolved. EDC (4.600 gram, 24 mmol) was added to the DCM solution, and once the EDC was dissolved, the solution was stirred at room temperature for 24 hours under $N_2$ and protection from light. The reaction mixture was reduced to a viscous liquid by rotary evaporation (25° C.) and washed three times with water (3×400 mL). The washed product was dissolved in diethyl ether (100 mL, 100 ppm BHT), and water was removed by mixing the solution with $MgSO_4$ for 1 hour. The solution was clarified by gravity filtration into a 250 mL flask, and the solvent was removed by rotary evaporation (25° C.). The product (Compound 2) was re-dissolved in DMF and was purified by fluorous SPE (F-SPE) and recovered by rotary evaporation. $^1$H NMR (300 MHz, $CDCl_3$) δ (ppm) 6.09-6.15 (HEMA vinyl H), 5.58-5.63 (HEMA vinyl H), 4.27-4.49 (—$CH_2$—O, BAL, $CH_2$ HEMA), 4.01-4.15 (—$CH_2$—O—CO PTMO), 3.75 (small $CH_3$ signal, LDI), 3.31-3.50 ($CH_2$—O PTMO), 3.07-3.23 (C$\underline{H}_2$—NH, LDI), 2.36-2.56 (—$CH_2$—$CF_2$—, BAL), 1.91-1.96 (HEMA $CH_3$) 1.27-1.74 (PTMO and LDI $CH_2$). $^{19}$F NMR (300 MHz, $CDCl_3$) δ (ppm) −81.23 ($CF_3$), −114.02 ($CF_2$), −122.34 ($CF_2$), −123.34 ($CF_2$), −123.30 ($CF_2$), −124.03 ($CF_2$), −126.56 ($CF_2$). GPC analysis: the product was dissolved in dioxane and run on a GPC system with a polystyrene column and UV detector. No free HEMA monomer detected in this analysis. HPLC analysis: retention time of 39.8 minutes (Compound 2), no free HEMA monomer detected in this analysis. Reversed phase HPLC, C18 column, MeOH and pH 9 PBS mobile phase (gradient). IR analysis was in accordance with the chemical structure: 3318 cm$^{-1}$ ν(N—H) H-bonded, 2935 cm$^{-1}$ ν(C—H) CH$_2$ asymmetric stretching, 2854 cm$^{-1}$ ν(C—H) CH$_2$ symmetric stretching, 1722 cm$^{-1}$ν(C═O) urethane amide, 1634 cm$^{-1}$ (vinyl C═C stretching), 1532 cm$^{-1}$ ν(C—N) stretching mode, 1456 cm$^{-1}$ ν(C—N) stretching mode, 1349.31 cm$^{-1}$ ν(C—O) stretching, 1400-1000 cm$^{-1}$ ν(C—F) monofluoroalkanes absorb to the right in the range, while polyfluoroalkanes give multiple strong bands over the range from 1350-1100 cm$^{-1}$. Elemental analysis: theoretical based on reagent stoichiometry (%): C, 49.64; H, 6.53; F, 21.71; N, 2.56; 0, 19.55. Measured: C, 50.78; H, 6.89; F, 19.33; N, 2.50.

Example 2: Synthesis of α, ω-BAL-Poly(LDI(Allyl)/PTMO) with Pendent Vinyl Groups (Compound 3)

yellow liquid. Column chromatography of the liquid using first diethyl ether, diethyl ether/DCM (50/50, w/w) mixture, DCM itself, and then a DCM/MeOH (80/20, w/w) mixture yielded an opaque liquid (Compound 3), 6.34 g (50.6%). Elemental analysis: Theoretical based on reagent stoichiometry (%): C, 49.61; H, 6.60; F, 23.24; N, 2.75; 0, 17.80. Measured: C, 49.47; H, 6.64; F, 24.87; N, 2.65. $^1$H-NMR (CDCl$_3$, 300 MHz): δ 5.92 (CH$_2$CHCH$_2$, allyl), 5.30 (CH$_2$CHCH$_2$ (geminal, allyl)), 4.74 (NH), 4.64 (CH$_2$CHCH$_2$, allyl), 4.37 (OCH$_2$, BAL, and NHCH, LDI), 4.08 (NH(O)COCH$_2$, PTMO), 3.42 (OCH$_2$CH$_2$, PTMO), 3.15 (NHCH$_2$, LDI), 2.46 (OCH$_2$CH$_2$, BAL), 1.87-1.20 (CH$_2$, LDI, and CH$_2$, PTMO). Based on integration of BAL at 2.47 ppm and allyl alcohol at 6.12 ppm, the amount of allyl alcohol attached onto the oligomer after the reaction was estimated to be 72%. The absolute number-average molecular weight (Mn) was estimated, using pentafluo-

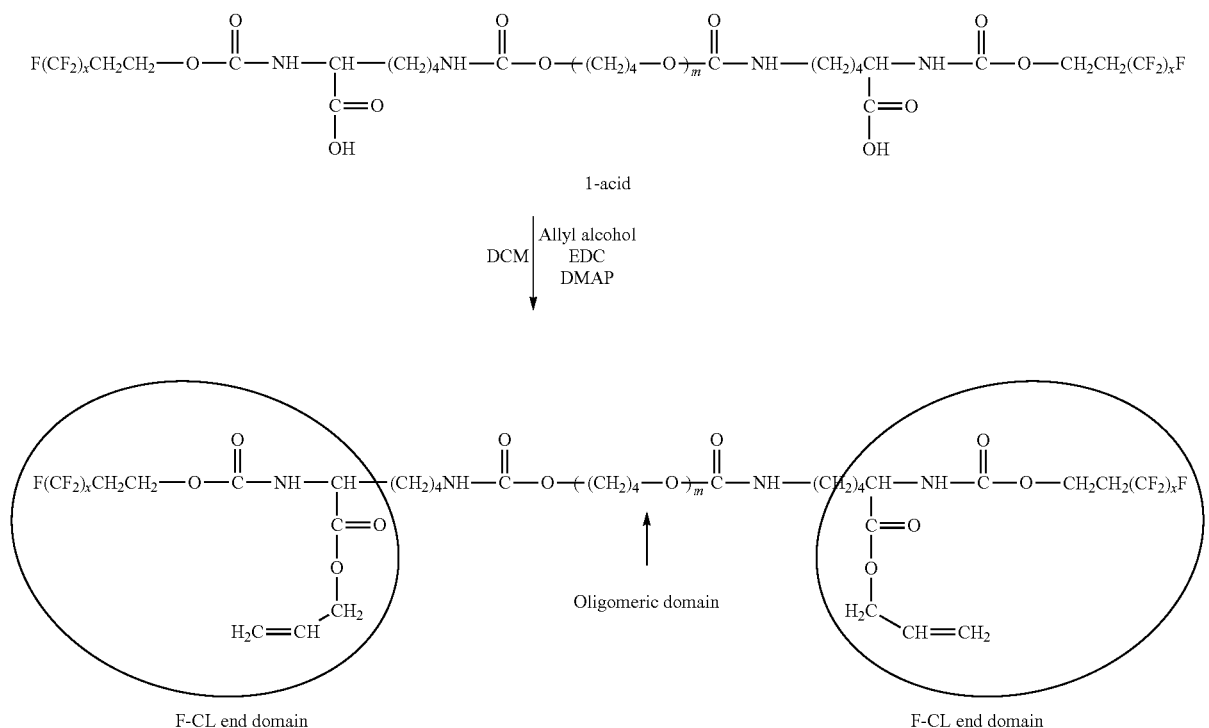

3

Compound 1-acid (12.03 g, 12.11 mmol), DMAP (0.74 g, 6.05 mmol), allyl alcohol (4.22 g, 72.64 mmol) and anhydrous DCM (100 mL) were weighed into a 250 mL flask equipped with a stir bar. The contents of the flask were magnetically stirred until all ingredients were dissolved. Then EDC (6.96 g, 36.32 mmol) white solid was added to the flask. The reaction flask was wrapped with aluminium foil and the solution was stirred at room temperature under N$_2$ for 3 days. After 3 days, DCM was removed by rotary evaporator at 25° C. to yield a viscous crude product. The crude product was washed three times with aqueous HCl (each time using a mixture of 30 mL of 0.1N HCl and 60 mL distilled water), and finally with distilled water (100 mL) itself. Extracting organic soluble materials (includes the desired product) into diethyl ether solvent, drying the organic solvent over solid MgSO$_4$, and removing the solvent by rotary evaporator at room temperature yielded a slightly robenzene (6.90 ppm) as the external reference against BAL at 2.46 ppm, PTMO at 3.42 ppm, LDI at 3.15 ppm and allyl at 5.92 ppm, to be 1845 g/mol. $^{19}$F-NMR (CDCl$_3$, 300 MHz, CFCl$_3$ as the internal reference standard): δ −81.26 (CF$_3$), −114.02 (CF$_2$), −122.41 (CF$_2$), −123.40 (CF$_2$), −124.15 (CF$_2$), −126.75 (CF$_2$). GPC analysis: the product was dissolved in dioxane and run on a GPC system with a polystyrene column and UV detector: no free monomer was detected. HPLC analysis: retention time of 40 minutes (Compound 3), no free allyl monomer detected. Reversed phase HPLC, C18 column, MeOH and pH 9 PBS mobile phase (gradient). FT-IR (KBr disc, neat): 3318 (N—H, broad), 2933-2794 (aliphatic C—H), 1704 (C═O), 1650 (C═C), 1530, 1436, 1355, 1255, 1100, 843, 809, 778, 745, 734, 707, 697 cm$^{-1}$.

Example 3: Synthesis of α,ω-Allyl-Poly(LDI(BAL)/PTMO) with Pendent Vinyl Groups (Compound 4)

Compound 4 was prepared by conjugating fluorinated groups to Compound 13 from Example 11.

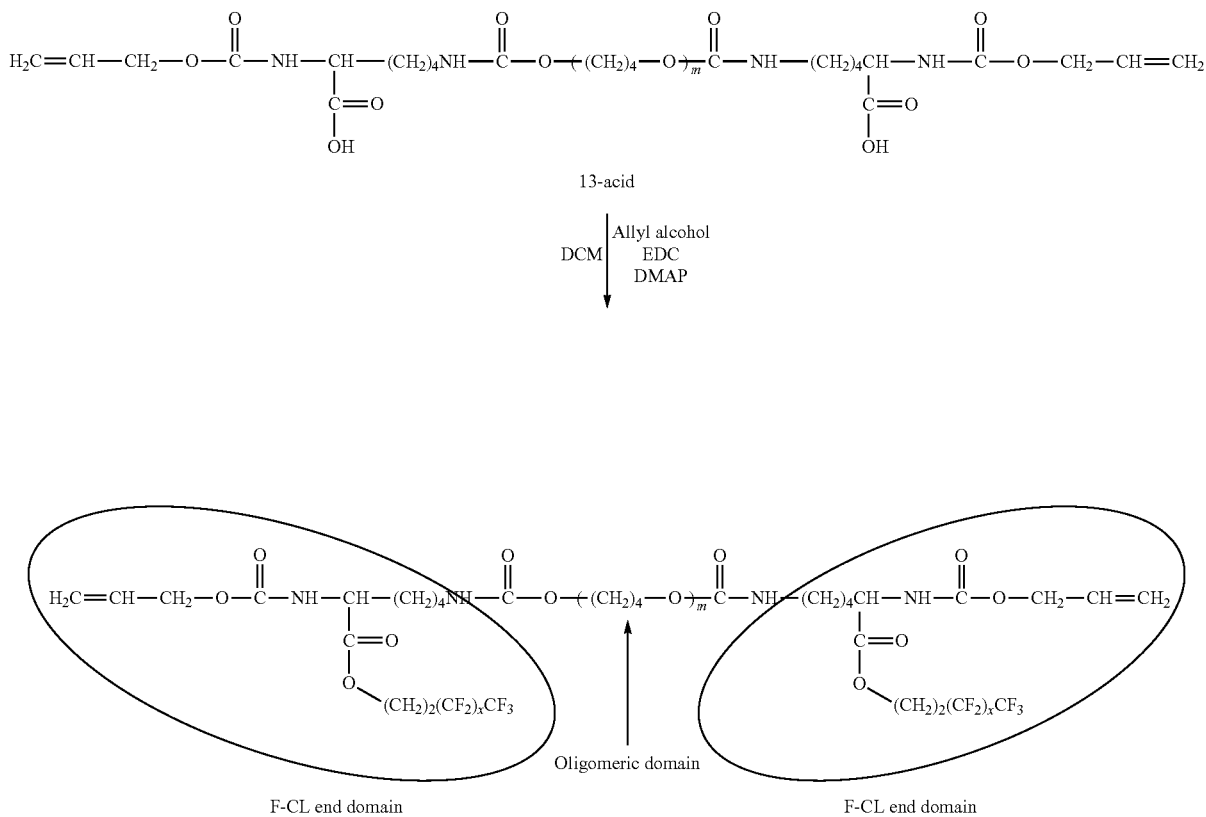

4

Compound 13-acid from Example 11 (7.52 g, 10.95 mmol), DMAP (0.67 g, 5.48 mmoL), BAL (23.06 g, 65.71 mmol, $M_n$=351 Daltons determined by $^1$H-NMR using pentafluorobenzene as the external reference), and anhydrous DCM (100 g) were weighed into a 250 mL flask equipped with a stir bar. The flask was magnetically stirred until all ingredients were dissolved. Then EDC (6.30 g, 32.86 mmol) white solid was added to the flask. The reaction flask was wrapped with aluminium foil and the solution was stirred at room temperature under $N_2$ for 5 days. After 5 days, DCM was removed by rotary evaporator at 25° C. to yield a yellow crude product. The crude product was washed three times with aqueous HCl (each time using a mixture of 30 mL of 0.1N HCl and 60 mL distilled water), and finally with distilled water (100 mL) itself. Extracting organic soluble materials (includes the desired product) into diethyl ether solvent, drying the organic solvent over solid $MgSO_4$, and removing the solvent by rotary evaporator at room temperature yielded a slightly yellow liquid. The liquid was dissolved in a small amount of acetone, and dropwise the acetone solution was added into a beaker containing methoxyperfluorobutane solvent (150 g), forming an emulsion. Centrifuging the emulsion at 3400 rpm and discarding the fluorinated solvent yielded a clear liquid, Compound 4. Elemental analysis: Theoretical based on reagent stoichiometry (%): C, 49.61; H, 6.60; F, 23.24; N, 2.74; 0, 17.80. Measured: C, 53.42; H, 7.76; F, 16.25; N, 2.70. $^1$H-NMR ($CDCl_3$, 300 MHz): δ 5.92 ($CH_2C\underline{H}CH_2$, allyl), 5.25 ($CH_2CHC\underline{H}_2$ (geminal, allyl)), 4.74 (N$\underline{H}$), 4.57 (C$\underline{H}_2$CHCH$_2$, allyl), 4.44 (OC$\underline{H}_2$, BAL), 4.32 (NHC$\underline{H}$, LDI), 4.08 (NH(O)COC$\underline{H}_2$, PTMO), 3.42 (OC$\underline{H}_2$, PTMO), 3.17 (NHC$\underline{H}_2$, LDI), 2.50 (OCH$_2$C$\underline{H}_2$, BAL), 1.87-1.20 ($CH_2$, LDI, and $CH_2$, PTMO). Based on integration of BAL at 2.47 ppm and LDI at 3.17 ppm, the amount of BAL attached onto the oligomer after the reaction was estimated to be 67%. The absolute number-average molecular weight (Mn) was estimated, using pentafluorobenzene (6.90 ppm) as the external reference against allyl at 5.92 ppm, PTMO at 3.42 ppm, BAL at 2.50 ppm and LDI at 3.17 ppm, to be 2007 g/mol. $^{19}$F-NMR ($CDCl_3$, 300 MHz, $CFCl_3$ as the internal reference standard): δ −81.14 ($CF_3$), −113.86 ($CF_2$), −122.19 ($CF_2$), −123.30 ($CF_2$), −123.89 ($CF_2$), −126.46 ($CF_2$). GPC analysis: the product was dissolved in dioxane and run on a GPC system with a polystyrene column and UV detector: no free monomer was detected. HPLC analysis: no free monomer detected. Reversed phase HPLC, C18 column, MeOH and pH 9 PBS mobile phase (gradient). FTIR (KBr, neat): 3315 (N—H, broad), 2933-2794 (aliphatic C—H), 1720 (C=O), 1644 (C=C), 1530, 1436, 1365, 1247, 1110, 778, 742, 733, 706, 696 $cm^{-1}$.

Example 4: Synthesis of α,ω-BAL-Poly(LDI/PTMO) with Pendent Amino Ethyl Methacrylate (Compound 5)

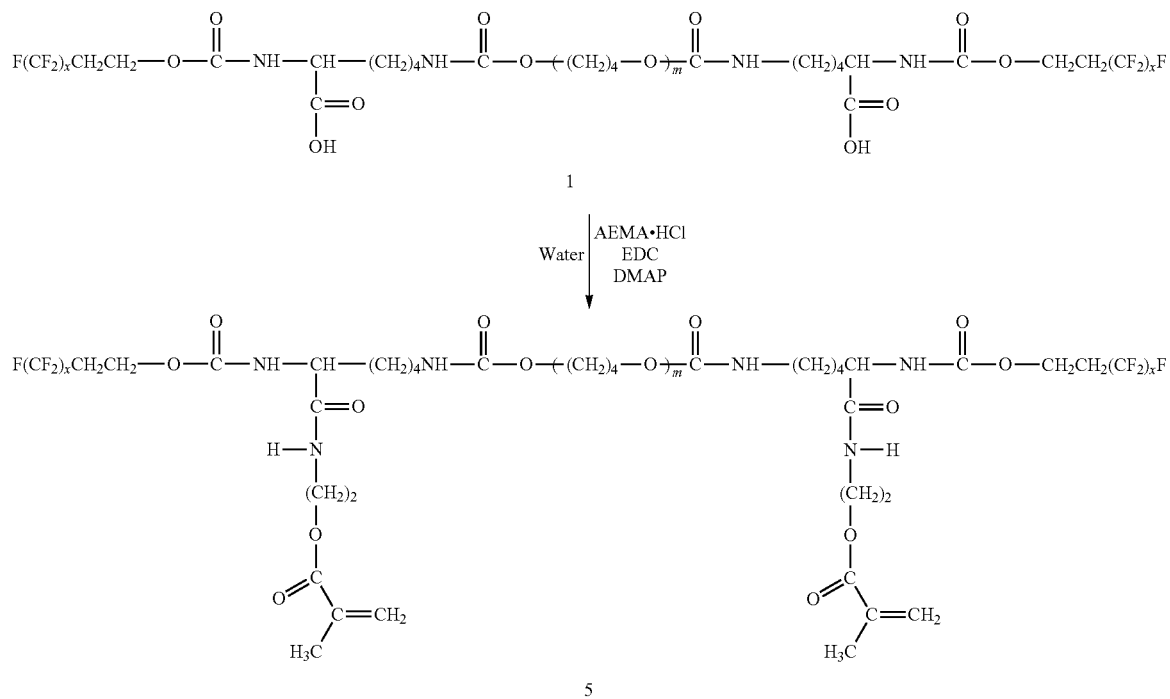

Compound 1-acid (0.5 gram, ~0.43 mmol acid) was weighed into a 2-neck flask, degassed, and dissolved in DMF (5 mL). The solution was chilled to 0° C., and to it was added EDC (0.245 g, 1.28 mmol) pre-dissolved in DMF (1 mL). The solution was raised to room temperature and stirred under nitrogen atmosphere and protection from light for two hours. Then, DMAP (0.026 g, 0.21 mmol) and AEMA.HCl (0.035 g, 0.21 mmol) were added to the flask, and stirred till all compounds were dissolved. The solution was kept stirring for one hour. The product (Compound 5) was precipitated and washed with water. The product was resuspended in acetone, dried with MgSO4, and the solvent was evaporated off at room temperature. $^1$H NMR (400 MHz, CDCl$_3$) δ (ppm) 6.13 (AEMA vinyl H), 5.61 (AEMA vinyl H), 4.36 (O—CH$_2$-BAL), 4.25 (CH$_2$, AEMA), 4.07 (—CH$_2$—O—CO PTMO), 3.75 (minor LDI ester CH$_3$), 3.41 (CH$_2$—O PTMO), 3.18 (C$\underline{H}_2$—NH, LDI), 2.45 (—CH$_2$—CF$_2$-BAL), 1.95 (—CH$_3$, AEMA), 1.62 (PTMO and LDI CH$_2$). GPC analysis: Compound 5 was dissolved in THF and run on a GPC system with a polystyrene column and UV detector. No free AEMA monomer detected in this analysis.

Example 5: Synthesis of α,ω-FEO1-Poly(LDI/PTMO) with Pendent Vinyl Groups (Compound 6)

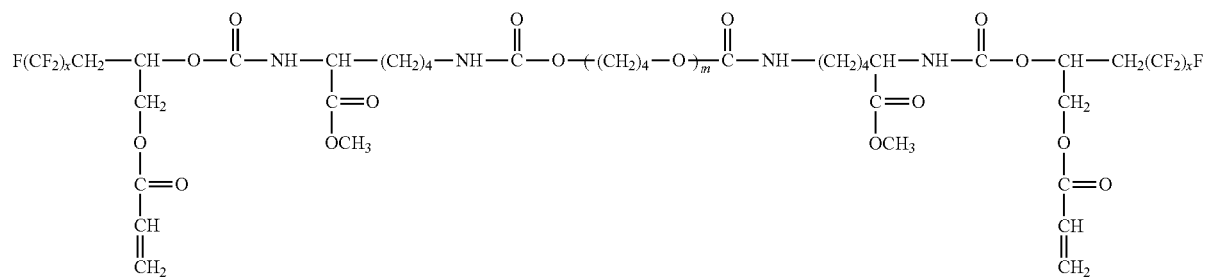

PTMO (10 g, 10 mmol, degassed) was dissolved in anhydrous DMAc (50 mL). LDI (4.11 g, 20 mmol, distilled) and DBDL catalyst were dissolved in anhydrous DMAc (25 mL) and added dropwise to the PTMO solution, and the reaction was maintained at 70° C. for two hours under N$_2$. The hydroxyperfluoroacrylate (4,4,5,5,6,6,7,7,8,8,9,9,10,10,11,11 heptadecafluoro-2-hydroxyundecyl acrylate) (FEO1, 12.058 g, 22 mmol) was dissolved in DMAc (25 mL) with DBDL and added dropwise to the reaction solution. The reactor was kept sealed under N$_2$ and stirred overnight at room temperature. The product was precipitated in water (2

L) and re-dissolved in diethyl ether (100 mL, 100 ppm BHT), dried with MgSO$_4$ and filtered. The ether solution was dropped into hexane (400 mL) to precipitate the product and extract un-reacted reagent. The hexane was decanted and the solvent extraction procedure was repeated twice. The purified product (Compound 6) was dissolved in diethyl ether (50 mL), and the solvent removed by rotary evaporation at room temperature. $^1$H NMR (400 MHz, CDCl$_3$) δ (ppm) 6.40-6.52 (FEO1 vinyl H), 6.09-6.23 (FEO1 vinyl H), 5.80-5.95 (FEO1 vinyl H), 4.15-4.53 (C—H FEO1, O—CH$_2$-FEO1), 4.00-4.15 (—CH$_2$—O—CO PTMO), 3.75 (LDI ester CH$_3$), 3.31-3.50 (CH$_2$—O PTMO), 3.05-3.25 (CH$_2$—NH, LDI), 2.35-2.61 (—CH$_2$—CF$_2$-FEO1), 1.25-1.73 (PTMO and LDI CH$_2$). GPC analysis: Compound 6 was dissolved in dioxane and run on a GPC system with a polystyrene column and UV detector. No free FEO1 monomer detected in this analysis. IR analysis: 1634 cm$^{-1}$ (C=C)

Example 6: Synthesis of α, ω-FEO2-Poly(LDI/PTMO) with Pendent Vinyl Groups (Compound 7)

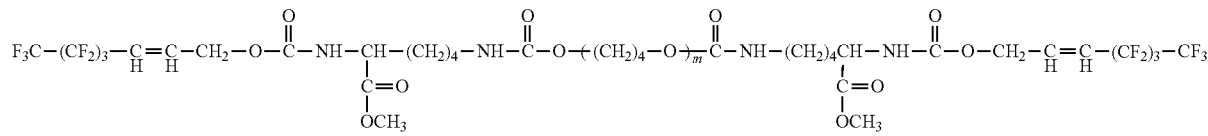

7

PTMO (2.012 g, 2 mmol, degassed) was dissolved in anhydrous DMAc (10 mL). LDI (0.848 g, 4 mmol, distilled) and DBDL catalyst were dissolved in anhydrous DMAc (5 mL) and was added dropwise to the PTMO solution. The pre-polymer reaction was maintained at 60-70° C. for two hours under N$_2$. The perfluor-en-ol (1H, 1H, 2H, 3H nonafluorohept-2-en-ol) (FEO2, 1.214 g, 4.4 mmol) was dissolved in DMAc (5 mL) with DBDL and added dropwise to the pre-polymer solution. The reactor was kept sealed under N$_2$ and stirred overnight at room temperature. The product was precipitated in water (0.5 L) and re-dissolved in diethyl ether (20 mL, 100 ppm BHT), dried with MgSO$_4$ and filtered. The ether solution was dropped into hexane (80 mL) to precipitate the product and extract un-reacted reagent. The hexane was decanted and the solvent extraction procedure was repeated twice. The purified product (Compound 7) was dissolved in diethyl ether (50 mL), and the solvent removed by rotary evaporation at room temperature. $^1$H NMR (400 MHz, CDCl$_3$) δ (ppm) 6.37-6.51 (vinyl H, FEO2), 5.76-5.95 (vinyl H, FEO2), 5.80-5.95 (FEO1 vinyl H), 4.66-4.87 (CH$_2$, FEO2), 4.24-4.38 ((—CH$_2$—O—CO LDI), 3.97-4.12 (—CH$_2$—O—CO PTMO), 3.66-3.77 (LDI ester CH$_3$), 3.27-3.52 (CH$_2$—O PTMO), 3.05-3.23 (CH$_2$—NH, LDI), 1.28-1.94 (PTMO and LDI CH$_2$). GPC analysis: (Compound 7) was dissolved in dioxane and run on a GPC system with a polystyrene column and UV detector. No free FEO2 monomer detected in this analysis. IR analysis: 1634 cm$^{-1}$ (C=C).

Example 7: Synthesis of α, ω-FEO3-Poly(LDI/PTMO) with Pendent Vinyl Groups (Compound 8)

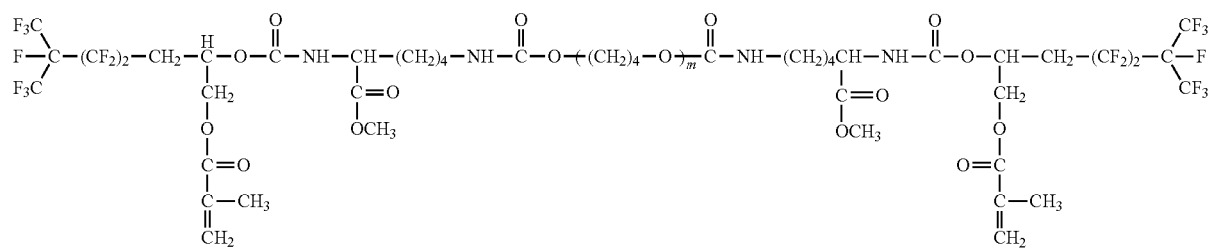

8

PTMO (10 g, 10 mmol, degassed) was dissolved in anhydrous DMAc (50 mL). LDI (4.241 g, 20 mmol, distilled) and DBDL catalyst were dissolved in anhydrous DMAc (22 mL) and was added dropwise to the PTMO solution. The pre-polymer reaction was maintained at 60-70° C. for two hours under $N_2$. The hydroxyperfluoroacrylate (3-(perfluoro-3-methylbutyl)-2-hydroxypropyl methacrylate) (FEO3, 9.068 g, 22 mmol) was dissolved in DMAc (23 mL) with DBDL and added dropwise to the pre-polymer solution. The reactor was kept sealed under $N_2$ and stirred overnight at room temperature. The product was precipitated in water (2 L) and re-dissolved in diethyl ether (100 mL, 100 ppm BHT), dried with $MgSO_4$ and filtered. The ether solution was dropped into hexane (400 mL) to precipitate the product and extract un-reacted reagent. The hexane was decanted and the solvent extraction procedure was repeated two times. The purified product (Compound 8) was dissolved in diethyl ether (50 mL), and the solvent removed by evaporation in a flow hood at room temperature. $^1$H NMR (400 MHz, $CDCl_3$) δ (ppm) 6.10-6.16 (FEO3 vinyl H), 5.66-5.89 (FEO3 vinyl H), 4.27-4.41 (—O—$CH_2$-FEO3), 4.15-4.27 (—O—$CH_2$-FEO3) 4.00-4.14 (—$CH_2$—O—CO PTMO), 3.75 (LDI ester $CH_3$), 3.27-3.52 ($CH_2$—O PTMO), 3.05-3.21 ($\underline{CH_2}$—NH, LDI), 2.34-2.61 (—$CH_2$—$CF_2$-FEO3), 1.90-1.99 ($CH_3$, FEO3), 1.22-1.90 (PTMO and LDI $CH_2$). GPC analysis: Compound 8 was dissolved in dioxane and run on a GPC system with a polystyrene column and UV detector. No free FEO3 monomer detected in this analysis. IR analysis: 1634 $cm^{-1}$ (C=C).

Example 7'

Synthesis of α,
ω-C8-Poly(LDI(hydroxyperfluoroacrylate)/PTMO)
with Pendent Vinyl Groups (Compound 9')

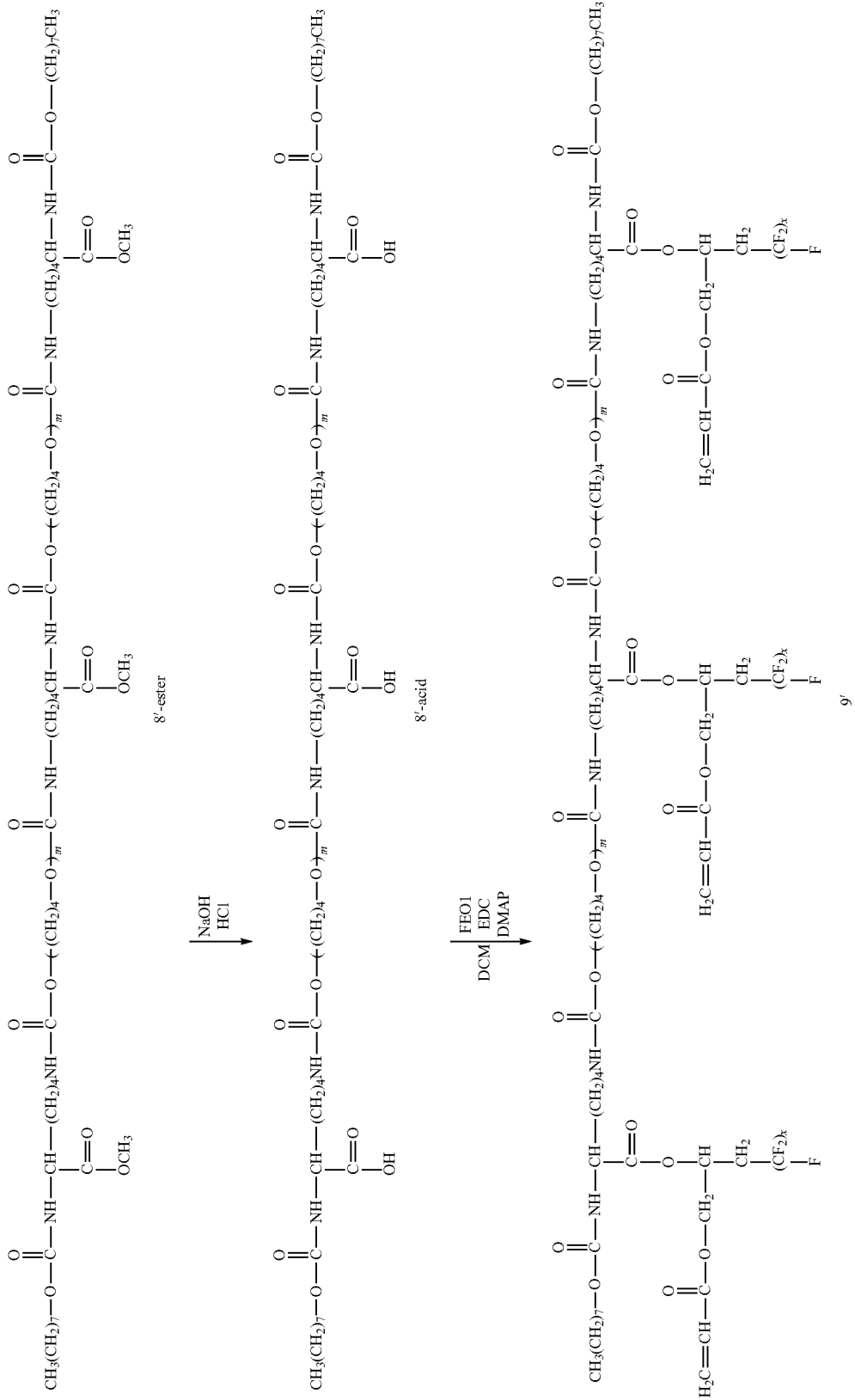

PTMO (10.0 g, 10.0 mmol) was weighed into a 250 mL round bottom flask equipped with a stir bar. The flask was heated to 30° C. using an oil bath, and was held under vacuum for 2 hours to remove trace amounts of water. The flask was cooled to room temperature and anhydrous DMAc (50 mL) was added to dissolve the PTMO. LDI (3.18 g, 15.0 mmol), DBDL and anhydrous DMAc (5 mL) were mixed and transferred to the flask via syringe. The reaction flask was heated to 70° C. in an oil bath, and the reaction mixture was stirred for 2 hours. Then, 1-octanol (1.43 g, 11 mmol) was introduced into the reactor by syringe injection, and the reaction mixture was kept stirring at room temperature overnight (17 hours). The next day, the reaction mixture was precipitated into 3 L of distilled water. The wash procedure was repeated twice with distilled water (3 L). The product was dried under a vacuum to yield the final product, Compound 8'-ester. $^1$H-NMR (CDCl$_3$, 300 MHz): δ 4.07 (NH(O)COC$\underline{H}_2$, PTMO), 3.74 (—OC$\underline{H}_3$, LDI), 3.41 (OC$\underline{H}_2$CH$_2$CH$_2$C$\underline{H}_2$O, PTMO, and (O)COC$\underline{H}_2$(CH$_2$)$_6$CH$_3$, octanol), 3.16 (NHC$\underline{H}_2$, LDI), 1.62 (CHC$\underline{H}_2$C$\underline{H}_2$CH$_2$CH$_2$NH, LDI, OCH$_2$CHCH$_2$CH$_2$O, PTMO, and (O)COCH$_2$(C$\underline{H}_2$)$_6$CH$_3$, octanol), 0.88 ((O)COCH$_2$(CH$_2$)$_6$C$\underline{H}_3$, octanol). The MW of Compound 8'-ester was higher compared to Compound 1 MW, as detected by GPC measurement.

Compound 8'-ester (5.0 g, 5.2 mmol ester) was weighed in a 250 mL beaker and was dissolved in acetone (50 mL). NaOH 1.0N (5.18 mL) was added dropwise to the beaker and the mixture was stirred at room temperature for 6 hours. The reaction mixture was then neutralized with 5.70 mL of 1.0 N aqueous HCl, and additional water was added to yield a white precipitate. Once the wash water was removed, the intermediate product was recovered and was washed twice with distilled water (1.0 L). The final product was dried under vacuum for 18 hours to yield an opaque viscous product, Compound 8'-acid. $^1$H-NMR (CDCl$_3$, 300 MHz): the singlet at 3.74 (—OCH$_3$) was used to monitor the degree of hydrolysis of the ester group.

Compound 8'-acid (0.43 g, 0.46 mmol acid), DMAP (27.2 mg, 0.22 mmoL), FEO1 (1.46 g, 2.67 mmol) and anhydrous DCM (7 mL) were weighed into a 50 mL flask equipped with a stir bar. The contents of the flask were magnetically stirred until all ingredients were dissolved. Then EDC (0.256 g, 1.3 mmol) white solid was added to the flask. The reaction flask was wrapped with aluminium foil and the solution was stirred at room temperature under N$_2$ overnight. The following day, the DCM was removed by rotary evaporation at 25° C. to yield a crude product. The crude product was washed using solvent and water extraction, dried over MgSO$_4$, and the solvent was removed by rotary evaporation. The final product (Compound 9') was dried under vacuum. $^1$H-NMR (CDCl$_3$, 300 MHz): δ 6.45, 6.19, 5.43 (vinyl H, FEO1), 4.07 (NH(O)COC$\underline{H}_2$, PTMO), 3.74 (minor —OC$\underline{H}_3$, LDI), 3.41 (OC$\underline{H}_2$CH$_2$CH$_2$C$\underline{H}_2$O$_2$, PTMO, and (O)COC$\underline{H}_2$(CH$_2$)$_6$CH$_3$, octanol), 3.16 (NHC$\underline{H}_2$, LDI), 2.42 (—CH$_2$—CF$_2$—, FEO1), 1.62 (CHC$\underline{H}_2$C$\underline{H}_2$CH$_2$CH$_2$NH, LDI, OCH$_2$C$\underline{H}_2$C$\underline{H}_2$CH$_2$O, PTMO, and (O)COCH$_2$(C$\underline{H}_2$)$_6$CH$_3$, octanol), 0.88 ((O)COCH$_2$(CH$_2$)$_6$C$\underline{H}_3$, octanol). GPC analysis: Compound 9' was dissolved in dioxane and run on a GPC system with a polystyrene column and UV detector. No free FEO1 monomer was detected in this analysis.

The above conjugation of FEO1 was reproduced using FEO3. Compound 8'-acid (2.5 g, 2.59 mmol acid), DMAP (0.158 g, 1.29 mmoL), FEO3 (6.396 g, 15.52 mmol) and anhydrous DCM (13 mL) were weighed into a 100 mL flask equipped with a stir bar. The contents of the flask were magnetically stirred until all ingredients were dissolved. Then EDC (1.487 g, 7.76 mmol) was added to the flask. The remaining synthesis and purification steps were identical to the FEO1 reaction. $^1$H-NMR (CDCl$_3$, 300 MHz): δ 6.14, 5.64 (vinyl H, FEO3), 4.07 (NH(O)COC$\underline{H}_2$, PTMO), 3.74 (minor —OC$\underline{H}_3$, LDI), 3.41 (OC$\underline{H}_2$CH$_2$CH$_2$C$\underline{H}_2$O, PTMO, and (O)COC$\underline{H}_2$(CH$_2$)$_6$CH$_3$, octanol), 3.16 (NHC$\underline{H}_2$, LDI), 2.4 (—CH$_2$—CF$_2$—, FEO3), 1.94 (CH$_3$, FEO3), 1.62 (CHC$\underline{H}_2$C$\underline{H}_2$CH$_2$ NH, LDI, OCH$_2$C$\underline{H}_2$C$\underline{H}_2$CH$_2$O, PTMO, and (O)COCH$_2$(C$\underline{H}_2$)$_6$CH$_3$, octanol), 0.88 ((O)COCH$_2$(CH$_2$)$_6$C$\underline{H}_3$, octanol). GPC analysis: Compound 9' (b) was dissolved in dioxane and run on a GPC system with a polystyrene column and UV detector. No free FEO3 monomer was detected in this analysis.

Example 8: Synthesis of α, ω-BAL-Poly(LDI(HEMA)/PSi) with Pendent Vinyl Groups (Compound 10)

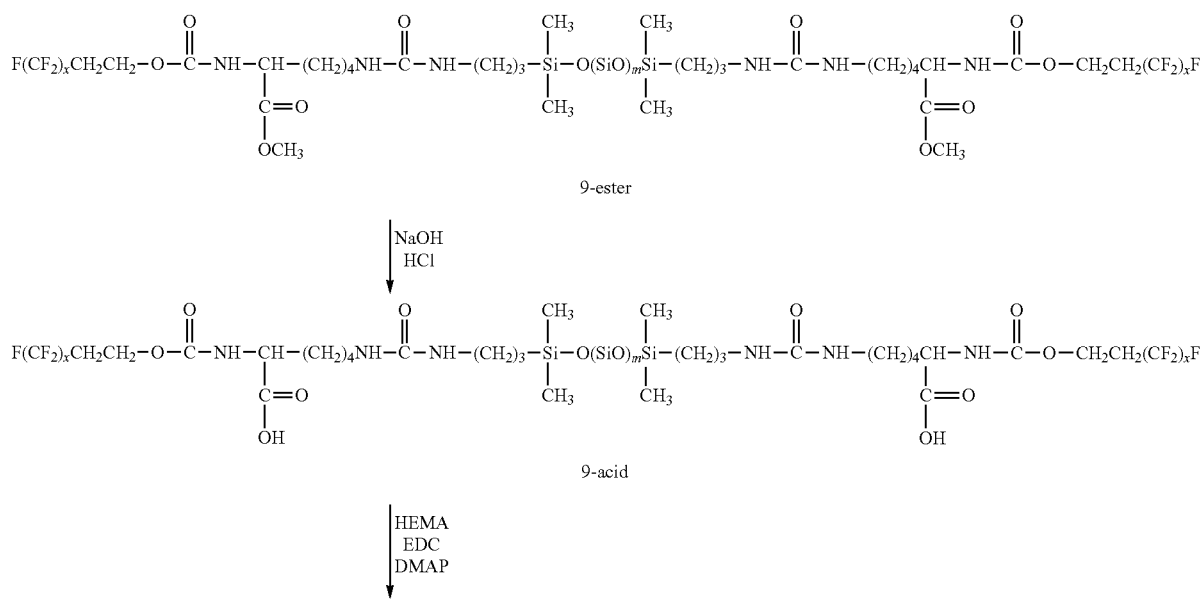

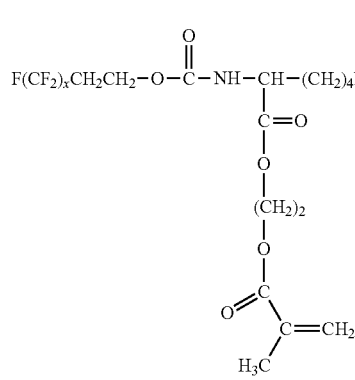
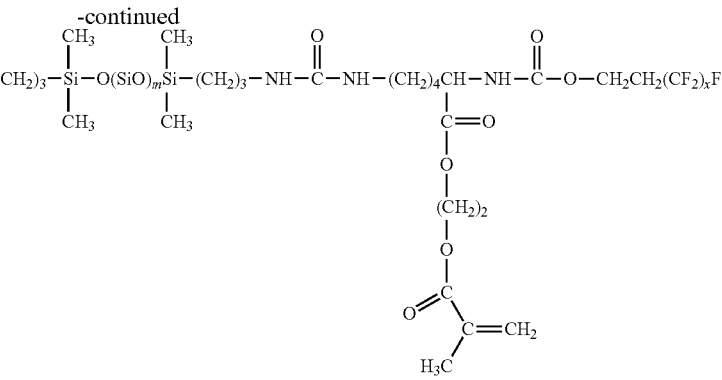

10

Poly(dimethylsiloxane), bis(3-aminopropyl) terminated (30.2 g, 12.1 mmol, $M_n$=2500, Aldrich) were weighed into a 250 mL round bottom flask equipped with a stir bar. The flask was heated to 45° C. using an oil bath, and under vacuum pumping for 2 hours to remove trace amounts of water. The flask was removed from the oil bath and allowed to cool to room temperature before it was transferred to a glove box with LDI, BAL, a 1 L bottle containing anhydrous DCM solvent and a flame-dry empty 250 mL round bottom flask equipped with a stir bar. In the glove box, LDI (5.13 g, 24.2 mmol) and anhydrous DCM (100 mL) was transferred to the empty flask. Anhydrous DCM (50 mL) was also transferred to the flask containing dry poly(dimethylsiloxane), and the flask was swirled until the content completely dissolved. The solution of poly(dimethylsiloxane) was then added dropwise to the flask containing LDI solution as the reaction mixture was stirred at room temperature. The addition complete in 10 minutes, and the reaction mixture was kept stirring for another 20 minutes. Then, BAL (8.48 g, 24.2 mmol, $M_n$=351 g/mol determined by $^1$H-NMR using pentafluorobenzene as the external reference) was transferred into the reactor. The reactor was capped by a rubber septum and removed from the glove box. While the reaction mixture was heated to 65° C. in an oil bath under $N_2$, DBDL (0.02 mL) was transferred to the reactor via. a syringe. The reactor was kept stirring at 65° C. overnight (17 hours). The next day, the reaction mixture was cooled to room temperature, and DCM solvent was removed by rotary evaporator to yield a liquid product (Compound 9-ester).

Compound 9-ester (30.5 g, 16.8 mmol) and DCM (100 mL) were transferred to a 500 mL flask containing a stir bar. Deionized water (3.33 g, 18.5 mmol) and NaOH in MeOH (0.10 N, 185 mL, 18.5 mmol) were added to the reactor. Note that if the ester-precursor solution turned cloudy during the addition of NaOH solution and water, more DCM solvent was required until the mixture became transparent. The reaction mixture was kept stirring at room temperature for 8 hours, and then neutralized with a 1.0 N $HCl_{(aq)}$ (20 mL, 20.0 mmol). Transferred the reaction mixture to a separatory funnel, washed it twice with deionized water and removed organic solvents by rotary evaporator yielded slightly yellow viscous liquid. Complete removal of residual organic solvents afforded transparent viscous liquid, Compound 9-acid.

Compound 9-acid (20.8 g, 11.56 mmol), DMAP (0.71 g, 5.78 mmol), HEMA (9.03 g, 69.37 mmol) and anhydrous DCM (150 mL) were transferred into a 500 mL flask equipped with a stir bar. The content of the flask were magnetically stirred until all ingredients were dissolved. Then white solid EDC (6.65 g, 34.69 mmol) was added to the flask. The reaction flask was wrapped with aluminium foil and kept stirring at room temperature under $N_2$ for 3 days. After 3 days, DCM was removed by rotary evaporator at 25° C. to yield a viscous crude product. The crude product was washed three times with distilled water (150 mL each time). Extracting organic soluble materials into diethyl ether solvent, drying the organic solvent over solid $MgSO_4$, and removing the solvent by rotary evaporator at room temperature yielded a viscous liquid. The viscous liquid was washed three times with MeOH (HPLC grade, 150 mL each time) to remove unreacted HEMA. MeOH solvent was discarded and removed completely by a vacuum pump to afford a transparent viscous liquid, Compound 10.

Example 9: Synthesis of α,ω-BAL-Poly(LDI(HEMA)/PCL) with Pendent Vinyl Groups (Compound 11')

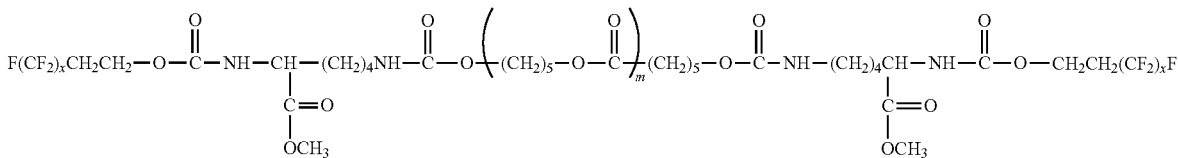

11-ester

↓ hydrolysis

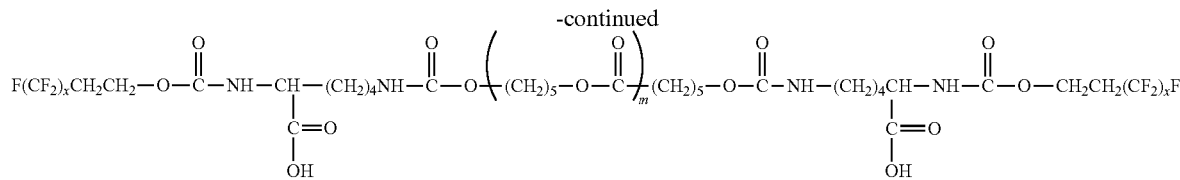

11-acid

DCM | HEMA
EDC
DMAP

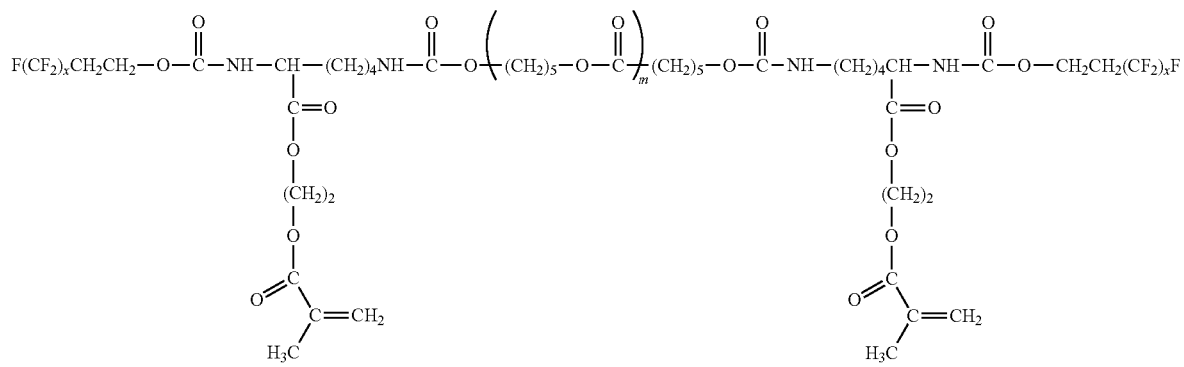

11'

Polycaprolactone diol (PCL diol) (10 grams, 8 mmol, degassed) was dissolved in anhydrous DMAc (50 mL). LDI (3.39 g, 16 mmol, distilled) and DBDL catalyst was dissolved in anhydrous DMAc (18 mL) and was added dropwise to the PCL diol solution. The pre-polymer reaction was maintained at 60-70° C. for two hours under $N_2$. BAL (7.39 g, 18 mmol) and DBDL were dissolved in anhydrous DMAc (25 mL) and were added dropwise to the pre-polymer solution. The reactor was kept sealed under $N_2$ and stirred overnight at room temperature. The product (Compound 11-ester) was precipitated in water (3 L), re-suspended in acetone, and purified by passing the acetone solution through SCX SPE columns. The acetone solution was evaporated at 40° C. in a flow oven, and the product was dried under vacuum. PCL diol and Compound 11-ester were dissolved in dioxane and were analyzed by GPC using polystyrene columns and UV detection: the Compound 11-ester chromatogram does not contain un-reacted PCL diol. $^1$H NMR (400 MHz, CDCl$_3$) δ (ppm) 4.28-4.46 (—C$\underline{H}_2$—O—CONH—, BAL), 4.16-4.27 (—C$\underline{H}_2$—O—CONH—, PCL), 3.98-4.11 (—CH$_2$—O—, PCL), 3.71-3.77 (CH$_3$, LDI), 3.09-3.22 (C$\underline{H}_2$—O—CONH—, LDI), 2.38-2.54 (CH$_2$—CF$_2$, BAL), 2.26-2.38 (O—CO—CH$_2$—, PCL), 1.45-1.76 (—CH$_2$—, PCL), 1.20-1.45 (—CH$_2$—, PCL).

Compound 11-ester (0.5 g, 0.4 mmol LDI ester) was dissolved in acetone (5 mL) and once dissolved, 1 N NaOH (0.4 mL, 0.4 mmol) was added with good stirring at room temperature for three hours. The product was neutralized with 1 N HCl (0.4 mL, 0.4 mmol) and water was added to complete the precipitation and wash the product. The product (Compound 11-acid) was dried under vacuum at 60° C. The conversion of ester functional groups to acid groups was monitored by proton NMR analysis.

Compound 11-acid (2.0 gram, 2.4 mmol acid), DMAP (0.145 g, 1.19 mmol), HEMA (1.863 g, 14.3 mmol) and DCM (10 mL) were added to a 100 mL flask, and were stirred until all compounds are dissolved. EDC (1.372 g, 7.16 mmol) was added to the DCM solution, and once the EDC was dissolved, the solution was stirred at room temperature for 24 hours under nitrogen atmosphere and protection from light. The reaction mixture was reduced to a viscous liquid by rotary evaporation and washed with water. The washed product was dissolved in ether and water was removed by mixing the solution with MgSO$_4$ for 1 hour. The solution was clarified by gravity filtration and the solvent was removed by rotary evaporation. The product (Compound 11') was re-dissolved in ether, and was purified by precipitation through hexane. $^1$H NMR (400 MHz, CDCl$_3$) δ (ppm) 6.08-6.17 (vinyl H, HEMA), 5.57-5.64 (vinyl H, HEMA), 4.30-4.54 (—C$\underline{H}_2$—O—CONH—, BAL), 4.21-4.27 (—C$\underline{H}_2$—O—CONH—, PCL), 3.99-4.13 (—CH$_2$—O—, PCL), 3.62-3.77 (minor, CH$_3$, LDI), 3.09-3.22 (C$\underline{H}_2$—O—CONH—, LDI), 2.43-2.56 (CH$_2$—CF$_2$, BAL), 2.24-2.40 (O—CO—CH$_2$—, PCL), 1.92-1.99 (CH$_3$, HEMA), 1.30-1.90 (—CH$_2$—, PCL).

Example 10: Synthesis of α,ω-FEO1-Poly(LDI/PCL) with Pendent Vinyl Groups (Compound 12)

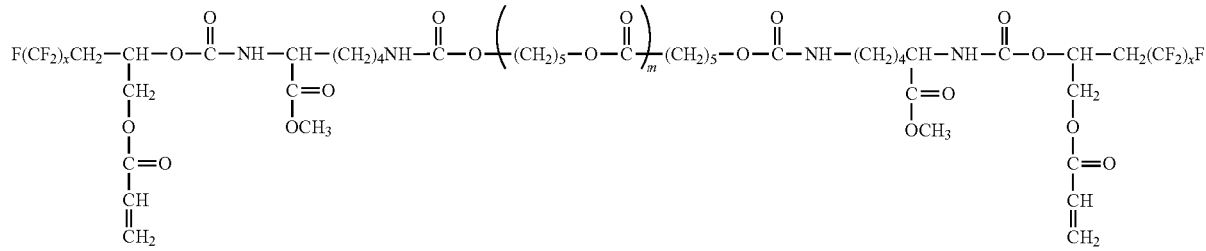

12

PCL diol (10 g, 8 mmol, degassed) was dissolved in anhydrous DMAc (50 mL). LDI (3.39 g, 16 mmol, distilled) and DBDL catalyst was dissolved in anhydrous DMAc (17 mL) and was added dropwise to the PCL diol solution. The pre-polymer reaction was maintained at 60-70° C. for two hours under $N_2$. FEO1 (9.648 g, 18 mmol) was dissolved in DMAc (24 mL) with DBDL and added dropwise to the pre-polymer solution. The reactor was kept sealed under $N_2$ and stirred overnight at room temperature. The product was precipitated in water (3 L) and re-dissolved in chloroform (100 mL, 100 ppm BHT), dried with $MgSO_4$, centrifuged and the supernatant decanted. The chloroform solution was dropped into hexane (400 mL) to precipitate the product and extract un-reacted reagent. The hexane was decanted and the solvent extraction procedure was repeated twice. The purified product (Compound 12) was dissolved in chloroform (50 mL), and the solvent removed at room temperature in a flow hood. $^1$H NMR (400 MHz, $CDCl_3$) δ (ppm) 6.41-6.49 (FEO1 vinyl H), 6.10-6.21 (FEO1 vinyl H), 5.87-5.94 (FEO1 vinyl H), 4.29-4.37 (O—$CH_2$, FEO1), 4.17-4.27 (—$CH_2$—O—CONH—, PCL, O—$CH_2$, FEO1), 3.98-4.11 (—$CH_2$—O—, PCL), 3.73-3.78 ($CH_3$, LDI), 3.64-3.73 (C—H, FEO1) 3.10-3.21 ($CH_2$—O—CONH—, LDI), 2.40-2.58 ($CH_2$—$CF_2$, FEO1), 2.26-2.38 (O—CO—$CH_2$—, PCL), 1.45-1.74 (—$CH_2$—, PCL), 1.18-1.44 (—$CH_2$—, PCL). GPC analysis: Compound 12 was dissolved in THF and run on a GPC system with a polystyrene column and UV detector. No free FEO1 monomer detected in this analysis. IR analysis: 1634 $cm^{-1}$ (C=C).

Example 11: Synthesis of α,ω-Allyl-Poly(LDI/PTMO) with Pendent Vinyl Groups (Compound 13)

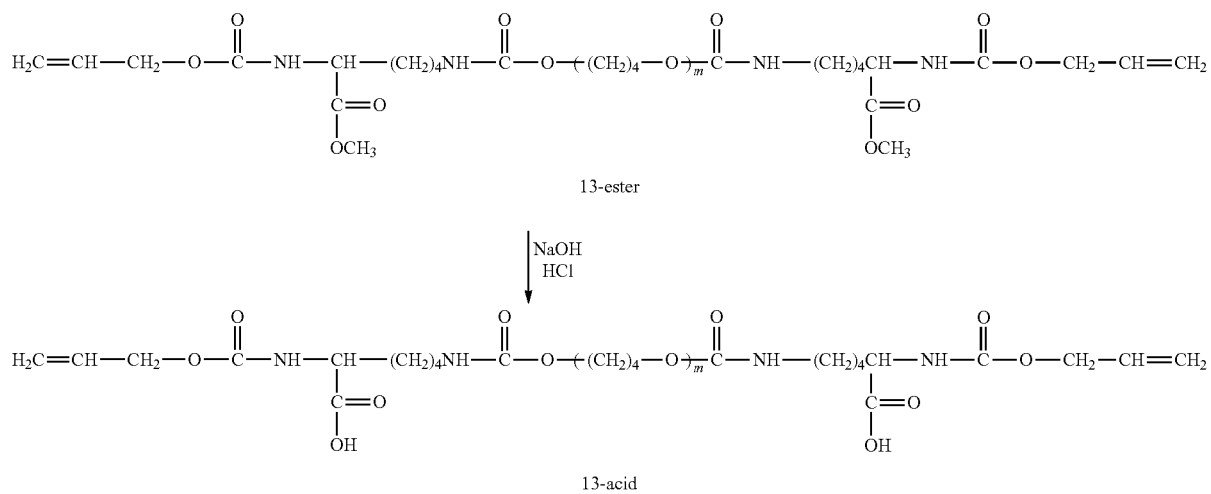

PTMO (20.00 g, 23.23 mmol, $M_n$=861 Daltons determined by $^1$H-NMR using pentafluorobenzene as the external reference) was weighed into a 250 mL round bottom flask equipped with a stir bar. The flask was heated to 45° C. using an oil bath, and was held under vacuum for 2 hours to remove trace amounts of water. The flask was removed from the oil bath and allowed to cool to room temperature before LDI (9.86 g, 46.46 mmol) and anhydrous DMAc (100 mL) were transferred to the flask via. two separate syringes. The reaction flask was heated to 65° C. in the oil bath and DBDL was syringed onto the flask. The reaction mixture was stirred at 65° C. for 3 hours, and then cooled to room temperature in an ice bath. Then, liquid allyl alcohol (2.70 g, 46.46 mmoL) was introduced into the reactor by syringe injection, and the reaction mixture was kept stirring at room temperature overnight (17 hours). The next day, the reaction mixture was poured into a 1 L beaker containing 900 mL distilled water in order to precipitate the polymer. Removing the wash water yielded a crude liquid product. Repeating the washing twice with distilled water (500 mL) generated a slightly yellow liquid. The liquid was dried under a vacuum for 18 hours, and yielded a liquid (Compound 13-ester). Elemental analysis: Theoretical based on reagent stoichiometry (%): C, 60.64; H, 9.46; N, 4.00; O, 25.90. Measured: C, 60.52; H, 9.55; N, 3.77; O, 25.36. $^1$H-NMR (CDCl$_3$, 300 MHz): δ 5.92 (CH$_2$C$\underline{H}$CH$_2$, allyl), 5.25 (CH$_2$CHC$\underline{H_2}$, geminal, allyl), 4.74 (N$\underline{H}$), 4.57 (C$\underline{H_2}$CHCH$_2$, allyl), 4.34 (NHC$\underline{H}$, LDI), 4.08 (NH(O)COC$\underline{H_2}$, PTMO), 3.74 (—OC$\underline{H_3}$, LDI), 3.42 (OC$\underline{H_2}$CH$_2$CH$_2$C$\underline{H_2}$O, PTMO), 3.17 (NHC$\underline{H_2}$, LDI), 1.87-1.20 (CHC$\underline{H_2}$C$\underline{H_2}$C$\underline{H_2}$CH$_2$NH, LDI, and OCH$_2$C$\underline{H_2}$C$\underline{H_2}$CH$_2$O, PTMO). Based on integration numbers of LDI at 3.17 ppm and allyl at 2.47 ppm, the 5.92 ppm, the amount of allyl groups attached onto the oligomer after the reaction was estimated to be 71%. The absolute number-average molecular weight (Mn) was estimated, using pentafluorobenzene (6.90 ppm) as the external reference against allyl at 5.92 ppm, PTMO at 3.42 ppm and LDI at 3.17 ppm, to be 1099 g/mol. GPC (DMF, 1 mL/min, linear PS as standards, UV at 280 nm and RI detector). FTIR (KBr, neat): 3315 (N—H, broad), 2933-2794 (aliphatic C—H), 1720 (C=O), 1644 (C=C), 1530, 1436, 1365, 1247, 1110, 778, 742 cm$^{-1}$.

Compound 13-ester (25.0 g, 35.67 mmoL) was weighed in a 500 mL flask containing 150 mL MeOH (HPLC grade) and a stir bar. A base solution of 1.62 g (40.5 mmoL) solid NaOH dissolved in 4.20 g of distilled water was added dropwise to the flask and the mixture was stirred at room temperature for 18 hours. The next day, the reaction mixture was neutralized with 7.0 mL of 6.0 N aqueous HCl, and then poured into a 2 L beaker containing 1.4 L distilled water, to yield a white precipitate. Extracting organic soluble materials (includes the desired product) into diethyl ether solvent, drying the organic solvent over solid MgSO$_4$, and removing the solvent by rotary evaporator at room temperature yielded a clear liquid. The organic solvent was further dried under vacuum for 18 hours to yield a clear viscous product, Compound 13-acid. Elemental analysis: Theoretical based on reagent stoichiometry (%): C, 60.13; H, 9.36; N, 4.08; O, 26.46. Measured: C, 60.05; H, 9.58; N, 3.36; O, 25.64. $^1$H-NMR (CDCl$_3$, 300 MHz): δ 5.92 (CH$_2$C$\underline{H}$CH$_2$, allyl), 5.25 (CH$_2$CHC$\underline{H_2}$, geminal, allyl), 4.74 (N$\underline{H}$), 4.57 (C$\underline{H_2}$CHCH$_2$, allyl), 4.34 (NHC$\underline{H}$, LDI), 4.08 (NH(O)COC$\underline{H_2}$, PTMO), 3.42 (OC$\underline{H_2}$CH$_2$CH$_2$C$\underline{H_2}$O, PTMO), 3.17 (NHC$\underline{H_2}$, LDI), 1.87-1.20 (CHC$\underline{H_2}$C$\underline{H_2}$C$\underline{H_2}$CH$_2$NH, LDI, and OCH$_2$C$\underline{H_2}$C$\underline{H_2}$CH$_2$O, PTMO). The singlet at 3.74 (—OCH$_3$) disappeared almost completely, confirming the hydrolysis of the ester group. Based on the peak integration the estimated conversion of ester to acid group was 97%. FTIR (KBr, neat): 3315 (N—H, broad), 2933-2794 (aliphatic C—H), 1720 (C=O), 1644 (C=C), 1530, 1436, 1365, 1247, 1110, 778, 742 cm$^{-1}$.

Example 12: Synthesis of α, ω-C8-Poly(LDI(HEMA)/PTMO) with Pendent Vinyl Groups (Compound 15)

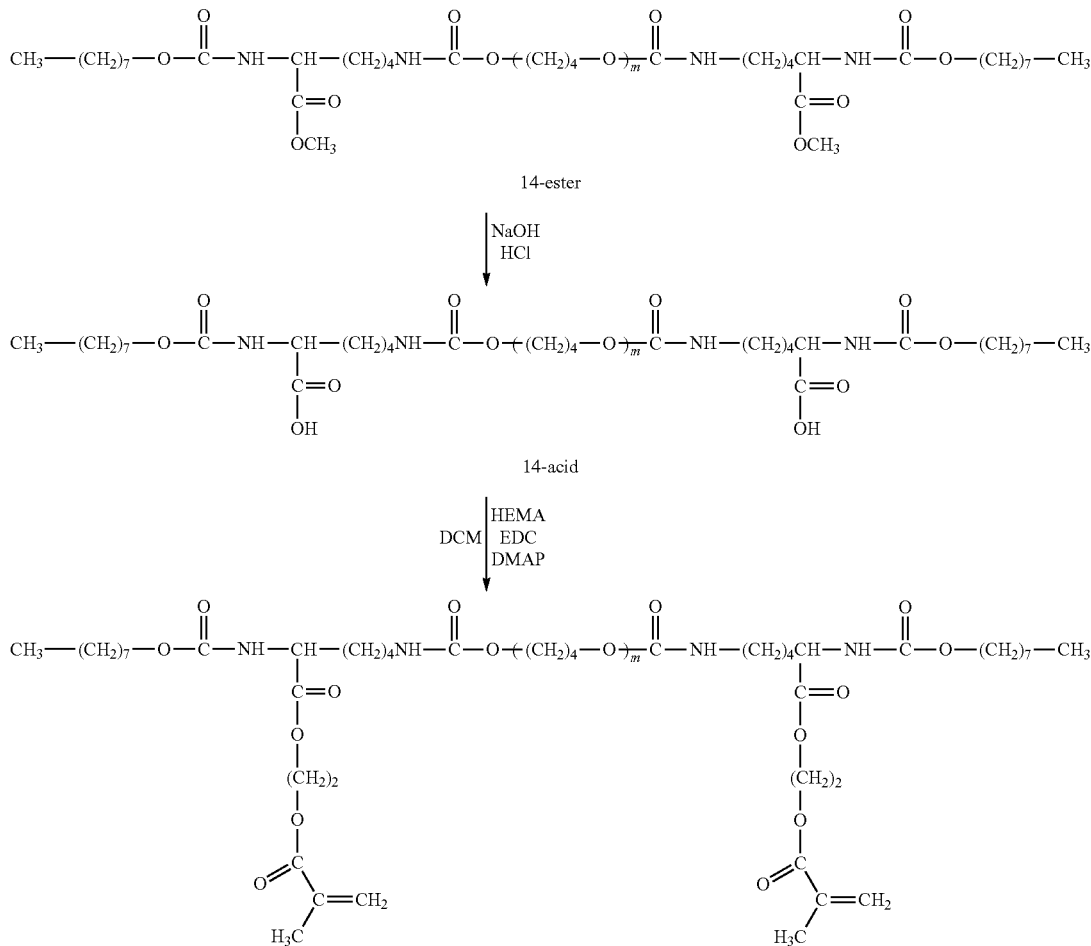

14-ester 14-acid

15

PTMO (41.29 g, 40.01 mmol, Mn=1032 Daltons, determined by titration of hydroxyl groups) was weighed into a 250 mL round bottom flask equipped with a stir bar. The flask was heated to 45° C. using an oil bath, and was held under vacuum for 2 hours to remove trace amounts of water. The flask was removed from the oil bath and allowed to cool to room temperature before LDI (16.97 g, 80.02 mmol) and anhydrous DMAc (100 mL) were transferred to the flask via two separate syringes. The reaction flask was heated to 65° C. in the oil bath and DBDL (0.05 mL) was syringed into the flask. The reaction mixture was stirred at 65° C. for 3 hours. Then, 1-octanol (10.42 g, 80.02 mmoL) was introduced into the reactor by syringe injection, and the reaction mixture was kept stirring at 65° C. overnight (17 hours). The next day, the reaction mixture was cooled to room temperature and poured into a 1 L beaker containing 900 mL distilled water in order to precipitate the polymer. Removing the wash water yielded a crude liquid product. Repeating the washing twice with distilled water (500 mL) generated a slightly yellow liquid (Compound 14-ester). The liquid was dried under a vacuum for 18 hours, and yielded a liquid with increased viscosity. Elemental analysis: Theoretical, based on reagent stoichiometry (%): C, 63.13; H, 10.24; N, 3.26; 0, 23.36. Measured: C, 62.28; H, 10.13; N, 3.33; 0, 24.19. $^1$H-NMR (CDCl$_3$, 300 MHz): δ 5.23 (N$\underline{H}$), 4.72 (N$\underline{H}$), 4.34 (NHCH, LDI), 4.08 (NH(O)COC$\underline{H}_2$, PTMO), 3.74 (—OC$\underline{H}_3$, LDI), 3.42 (OC$\underline{H}_2$CH$_2$CH$_2$C$\underline{H}_2$O, PTMO, and (O)COC$\underline{H}_2$(CH$_2$)$_6$CH$_3$, octanol), 3.17 (NHC$\underline{H}_2$, LDI), 1.84-1.18 (CHC$\underline{H}_2$C$\underline{H}_2$C$\underline{H}_2$CH$_2$NH, LDI, OCH$_2$C$\underline{H}_2$C$\underline{H}_2$CH$_2$O, PTMO, and (O)COCH$_2$(C$\underline{H}_2$)$_6$CH$_3$, octanol), 0.89 ((O)COCH$_2$(CH$_2$)$_6$C$\underline{H}_3$, octanol). Based on integration numbers of LDI at 3.17 ppm and octanol at 0.89 ppm, the amount of octanol attached onto the oligomer after the reaction was estimated to be 89%. The absolute number-average molecular weight (Mn) was estimated, using pentafluorobenzene (6.90 ppm) as the external reference against octanol at 0.89 ppm, PTMO at 3.42 ppm and LDI at 3.17 ppm, to be 1425 g/mol. FTIR (KBr, neat): 3314 (N—H, broad), 2933-2728 (aliphatic C—H), 1710 (C=O), 1524, 1437, 1364, 1245, 1238, 1204, 1107, 778 cm$^{-1}$.

Compound 14-ester (45.0 g, 52.4 mmoL) was weighed in a 500 mL flask containing 150 mL MeOH (HPLC grade) and a stir bar. A base solution of 2.31 g (57.7 mmoL) solid NaOH dissolved in 6 g of distilled water was added dropwise to the flask and the mixture was stirred at room temperature for 21 hours. The next day, the reaction mixture was neutralized with 11.0 mL of 6.0 N aqueous HCl, and then poured into a 2 L beaker containing 1.4 L distilled water, to yield a white precipitate. Once the wash water was removed, a crude waxy product was obtained. This was washed twice with distilled water (1.0 L), and the final product was dried under vacuum for 18 hours to yield an opaque viscous product (Compound 14-acid). Elemental analysis: Theoretical, based on reagent stoichiometry (%): C, 62.76; H, 10.18; N, 3.32; 0, 23.74. Measured: C, 62.08; H, 10.15; N, 3.32; 0, 23.19. $^1$H-NMR (CDCl$_3$, 300 MHz): δ δ 5.23 (N$\underline{H}$), 4.72 (N$\underline{H}$), 4.34 (NHC$\underline{H}$, LDI), 4.08 (NH(O)COC$\underline{H}_2$, PTMO), 3.42 (OC$\underline{H}_2$CH$_2$CH$_2$C$\underline{H}_2$O, PTMO, and (O)COC$\underline{H}_2$(CH$_2$)$_6$CH$_3$, octanol), 3.17 (NHC$\underline{H}_2$, LDI), 1.84-1.18 (CHC$\underline{H}_2$C$\underline{H}_2$C$\underline{H}_2$CH$_2$NH, LDI, OCH$_2$C$\underline{H}_2$C$\underline{H}_2$CH$_2$O, PTMO, and (O)COCH$_2$(C$\underline{H}_2$)$_6$CH$_3$, octanol), 0.89 ((O)COCH$_2$(CH$_2$)$_6$C$\underline{H}_3$, octanol). The singlet at 3.74 (—OCH$_3$) disappeared, confirming the hydrolysis of the ester group. Based on the peak integration the estimated conversion of ester to acid group was 81%. The absolute number-average molecular weight (Mn) was estimated, using pentafluorobenzene (6.90 ppm) as the external reference against octanol at 0.89 ppm, PTMO at 3.42 ppm and LDI at 3.17 ppm, to be 1430 g/mol. FTIR (KBr, neat): 3314 (N—H, broad), 2933-2728 (aliphatic C—H), 1710 (C=O), 1524, 1437, 1364, 1245, 1238, 1204, 1107, 778 cm$^{-1}$.

Compound 14-acid (12.20.0 g, 14.45 mmol), DMAP (0.88 g, 7.23 mmoL), HEMA (11.28 g, 86.70 mmol) and anhydrous DCM (150 g) were weighed into a 250 mL flask equipped with a stir bar. The contents of the flask were magnetically stirred until all ingredients were dissolved. Then EDC (8.31 g, 43.35 mmol) was added to the flask. The reaction flask was wrapped with aluminium foil and the solution was stirred at room temperature under N$_2$ for 5 days. After 5 days, DCM was removed by rotary evaporator at 25° C. to yield a viscous crude product. The crude product was washed three times with aqueous HCl (each time using a mixture of 30 mL of 0.1N HCl and 60 mL distilled water), and finally with distilled water (100 mL) itself. Extracting organic soluble materials (includes the desired product) into diethyl ether solvent, drying the organic solvent over solid MgSO$_4$, and removing the solvent by rotary evaporator at room temperature yielded a slightly yellow liquid. Column chromatography of the viscous liquid using first diethyl ether, a diethyl ether/DCM mixture (50/50, w/w), DCM itself, and then a DCM/MeOH mixture (70/30, w/w) yielded a clear viscous liquid (Compound 15), 6.35 g (46%). Elemental analysis: Theoretical, based on reagent stoichiometry (%): C, 62.95; H, 9.83; N, 2.93; 0, 24.31. Measured: C, 62.17; H, 9.84; N, 3.18; 0, 24.11. $^1$H-NMR (CDCl$_3$, 300 MHz): δ 6.12 (geminal C$\underline{H}$, HEMA), 5.60 (geminal C$\underline{H}$, HEMA), 5.24 (N$\underline{H}$), 5.23 (N$\underline{H}$), 4.77 (N$\underline{H}$), 4.34 (NHC$\underline{H}$, LDI, and OC$\underline{H}_2$CH$_2$O, HEMA), 4.08 (NH(O)COC$\underline{H}_2$, PTMO), 3.51-3.30 (OC$\underline{H}_2$CH$_2$CH$_2$C$\underline{H}_2$O, PTMO, and (O)COC$\underline{H}_2$(CH$_2$)$_6$CH$_3$, octanol), 3.14 (NHC$\underline{H}_2$, LDI), 1.95 ((O)CC(C$\underline{H}_3$)CH$_2$, HEMA), 1.84-1.18 (CHC$\underline{H}_2$C$\underline{H}_2$C$\underline{H}_2$CH$_2$NH, LDI, OCH$_2$C$\underline{H}_2$C$\underline{H}_2$CH$_2$O, PTMO, and (O)COCH$_2$(C$\underline{H}_2$)$_6$CH$_3$, octanol), 0.89 ((O)COCH$_2$(CH$_2$)$_6$C$\underline{H}_3$, octanol). The estimate conversion of COOH to CO-HEMA is 48% based on $^1$H-NMR shift area of 6.12 ppm (HEMA) and 3.14 ppm (LDI). The absolute number-average molecular weight (Mn) was estimated, using pentafluorobenzene (6.90 ppm) as the external reference against octanol at 0.89 ppm, PTMO at 3.42 ppm and LDI at 3.17 ppm, to be 1722 g/mol. GPC analysis: the product was dissolved in dioxane and run on a GPC system with a polystyrene column and UV detector: no free monomer was detected. HPLC analysis: retention time of 41 minutes (Compound 15), no free monomer detected. Reversed phase HPLC, C18 column, MeOH and pH 9 PBS mobile phase (gradient). FTIR (KBr, neat): 3314 (N—H, broad), 2933-2728 (aliphatic C—H), 1710 (C=O), 1636 (C=C), 1524, 1437, 1364, 1245, 1238, 1204, 1107, 778 cm$^{-1}$.

Example 13: Synthesis of α,ω-C8-Poly(LDI(Allyl)/PTMO) with Pendent Vinyl Groups (Compound 16)

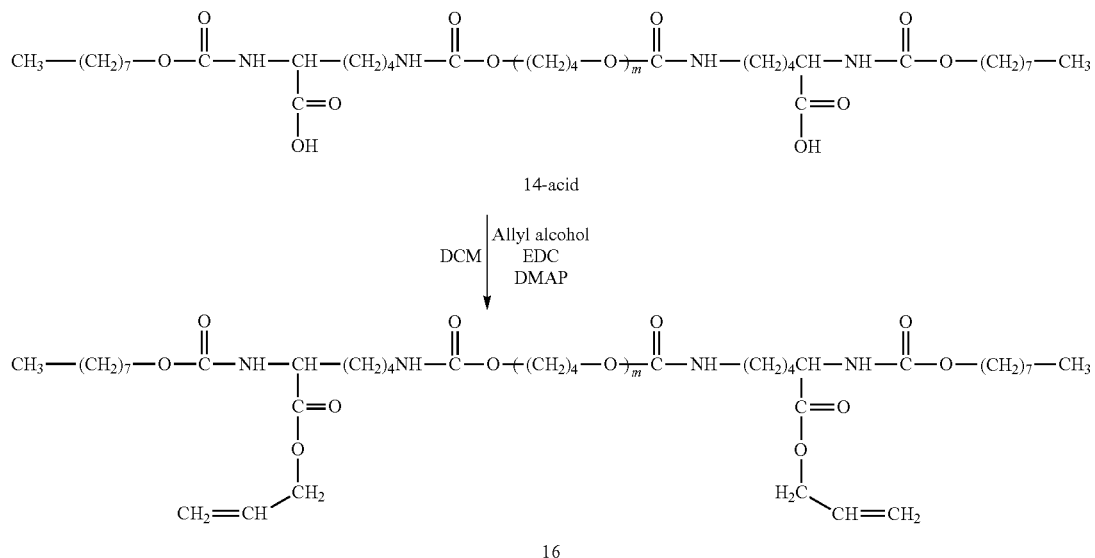

16

Compound 14-acid (9.83 g, 11.64 mmol), DMAP (0.71 g, 5.82 mmol), allyl alcohol (4.06, 69.86 mmol) and anhydrous DCM (100 g) were weighed into a 250 mL flask equipped with a stir bar. The contents of the flask were magnetically stirred until all ingredients were dissolved. Then EDC (6.70 g, 34.93 mmol) white solid was added to the flask. The reaction flask was wrapped with aluminium foil and the solution was stirred at room temperature under $N_2$ for 3 days. After 3 days, DCM was removed by rotary evaporator at 25° C. to yield a viscous crude product. The crude product was washed three times with aqueous HCl (each time using a mixture of 30 mL of 0.1N HCl and 60 mL distilled water), and finally with distilled water (100 mL) itself. Extracting organic soluble materials (includes the desired product) into diethyl ether solvent, drying the organic solvent over solid $MgSO_4$, and removing the solvent by rotary evaporator at room temperature yielded a clear liquid. Column chromatography of the viscous liquid using first diethyl ether, a diethyl ether/DCM mixture (50/50, w/w), DCM itself, and then a DCM/MeOH mixture (70/30, w/w) yielded a clear viscous product (Compound 16), 6.21 g (60% yield). Elemental analysis: Theoretical based on reagent stoichiometry (%): C, 63.99; H, 10.17; N, 3.17; O, 22.67. Measured: C, 62.51; H, 9.97; N, 3.19; O, 24.01. $^1$H-NMR (CDCl$_3$, 300 MHz): δ 5.92 (CH$_2$CHCH$_2$, allyl), 5.28 (CH$_2$CHCH$_2$ (geminal, allyl)), 4.74 (NH), 4.64 (CH$_2$CHCH$_2$, allyl), 4.35 (NHCH, LDI), 4.08 (NH(O)COCH$_2$, PTMO), 3.42 (OCH$_2$CH$_2$CH$_2$CH$_2$O, PTMO, and (O)COCH$_2$(CH$_2$)$_6$CH$_3$, octanol), 3.15 (NHCH$_2$, LDI), 1.84-1.18 (CHCH$_2$CH$_2$CH$_2$CH$_2$NH, LDI, OCH$_2$CH$_2$CH$_2$CH$_2$O, PTMO, and (O)COCH$_2$(CH$_2$)$_6$CH$_3$, octanol), 0.89 ((O)COCH$_2$(CH$_2$)$_6$CH$_3$, octanol). The estimate conversion of COOH to CO-allyl alcohol is 38% based on $^1$H-NMR shift area of 5.92 ppm (allyl) and 3.15 ppm (LDI). The absolute number-average molecular weight (Mn) was estimated, using pentafluorobenzene (6.90 ppm) as the external reference against octanol at 0.89 ppm, allyl at 5.92 ppm, PTMO at 3.42 ppm and LDI at 3.17 ppm, to be 1576 g/mol. GPC analysis: the product was dissolved in dioxane and run on a GPC system with a polystyrene column and UV detector: no free monomer was detected. HPLC analysis: retention time of 41 minutes (Compound 16), no free monomer detected. Reversed phase HPLC, C18 column, MeOH and pH 9 PBS mobile phase (gradient). FTIR (KBr, neat): 3314 (N—H, broad), 2933-2728 (aliphatic C—H), 1710 (C=O), 1650 (C=C), 1524, 1437, 1364, 1245, 1238, 1204, 1107, 778 cm$^{-1}$.

Cured System Based on Homo Cross-Linking

Example 14: Homo Cross-Linked Films of Compound 2 Prepared by UV Cure in Air Compound 2 (0.50 g) and HMP (0.0025 g) were weighed a 20 mL vial. A small amount of MeOH (HPLC grade, 0.3 g) was added to the vial to reduce the viscosity of the mixture and to ensure good mixing. The vial was vortexed until the components were completely well blended. The mixture was cast onto various substrates including stainless steel discs or plates, an aluminum weighing pan and a KBr disc. MeOH solvent was allowed to evaporate at room temperature for 1 h under an aluminum foil. The stainless steel substrates, weighing pan and KBr disc containing liquid samples were placed in the center of the UV box before the UV lamp was turned on for 5 minutes, to yield the solid polymer films. All substrates were removed from the box and cooled to room temperature before carrying out film analysis.

Gel content, swell ratio, contact angle measurements, DSC and TGA analysis were performed on films prepared on stainless steel substrates. The typical thickness of these films was 0.4 mm. XPS analysis was performed on films cast in weighing pans. Gel content: 98%±3 (n=3). Swell ratio: 1.6±0.2 (n=3). Contact angle: 131.0°±2.7 (5 spots, 3 measurements/spot). XPS analysis (90°): (top surface: C: 68.84%, N: 4.08%, O: 14.24%, F: 28.44%.) DSC: negative heat flow: −70.34° C. ($T_g$ of PTMO). TGA: 2 onset points: (A) 259.1° C., 28.3% mass loss, and (B) 404.9° C., 69.4% mass loss. The C=C group conversion was monitored on films prepared on KBr discs: C=C conversion was recorded.

Example 15: Homo Cross-Linked Films of Compound 2 Prepared by UV Cure Under Argon with Two Different Concentrations of Initiator (0.5 and 1 wt %)

Compound 2 (2.9815 g or 2.9542 g) and HMP (0.0145 g or 0.0298 g) were weighed in a 20 mL vial. MeOH (HPLC grade, 5 g) was added to the vial to reduce the viscosity of the mixture and to ensure good mixing. The vial was vortexed until the components were completely well blended. If air bubbles appeared, the vial was allowed to sit at room temperature until all bubbles dissipated, before the mixture was cast onto the desired substrates such as Teflon molds, stainless steel discs, an aluminum weighing pan and a KBr disc. MeOH solvent was allowed to evaporate at room temperature for 1 hour or 24 hours under an aluminum foil. After 1 hour, the stainless steel discs, aluminum weighing pan and KBr disc containing liquid samples were placed in the center of the UV box. The box was purged with argon gas for 10 minutes before the UV lamp was turned on for 5 minutes. All substrates were removed from the box and cooled to room temperature before carrying out film analysis. After 24 hours, the UV cure procedure was repeated to samples cast on Teflon molds. Gel content, swell ratio, contact angle measurements, TGA analysis were performed on films prepared on stainless steel discs. The typical thickness of these films was 0.4 mm. XPS analysis was performed on films cast in weighing pans. The C=C group conversion was monitored by FTIR and performed on films prepared on KBr discs. The average thickness of these latter two films was about 0.03 mm. For tensile measurements, transparent polymer films free of air bubbles were removed from the molds and cut into to dog-bone shape (FIG. 1). The dog-bone samples were air-tightened on an instron machine for subsequent tensile test measurements. An Instron 4301 system was used to test the samples with a cross-head load of 50 N at the rate of 10 mm/min, at 23° C. and relative humidity of 57%. Sample thickness was measured by a caliper ranged from 0.1 to 0.3 mm. The results of each example represent an average of 4 or 5 dog-bone samples.

TABLE 2

Polymer film properties after Compound 2 was UV cured with 0.5 and 1.0 wt % photoinitiator under an inert atmosphere.

| | 0.5 wt % photoinitiator | 1.0 wt % photoinitiator |
|---|---|---|
| C=C conversion (%) | Recorded | Recorded |
| Gel content (%) | 98 ± 3 (n = 3) | 97 ± 1 (n = 3) |
| Swell ratio | 1.43 ± 0.05 (n = 3) | 1.41 ± 0.04 (n = 3) |
| Contact angle (°) | 133.4 ± 2.2 | 132.4 ± 2.2 |
| XPS (90°) | C: 53.39%, N: 4.24%, O: 14.15%, F: 28.12%. | C: 52.03%, N: 4.06%, O: 14.17%, F: 29.50%. |
| TGA | 265.1° C., 27.8% mass loss 412.9° C., 69.6% mass loss | 251.7° C., 18.2% mass loss 401.9° C., 75.9% mass loss |
| Tensile testing | n = 3 Stress at break: 3.0 MPa Strain at break: 41% Initial modulus (10% strain): 0.084 Toughness: 66.4 MPa | n = 3 Stress at break: 2.9 MPa Strain at break: 37.5% Initial modulus (10% strain): 0.085 Toughness: 61.6 MPa |

Example 16: Homo Cross-Linked Films of Compound 3 Prepared by UV Cure

Compound 3 (0.5934 g), HMP (0.0029 g) and MeOH (HPLC grade, 0.3 g) were weighed in a 20 mL vial. The vial was vortexed until all the components were well blended. If air bubbles appeared, the vial was allowed to sit at room temperature until all bubbles dissipated, before the mixture was cast onto the desired substrates (stainless steel discs, an aluminum weighing pan and a KBr disc). MeOH solvent was allowed to evaporate at room temperature for 1 h under an aluminum foil. The stainless steel discs, aluminum weighing pan and KBr disc containing liquid samples were placed in the center of the UV box. The box was purged with argon gas for 10 minutes before the UV lamp was turned on for 5 minutes. All substrates were removed from the box and cooled to room temperature before carrying out film analysis. Gel content, swell ratio, contact angle measurements, DSC and TGA analysis were performed on films prepared on stainless steel disks. The typical thickness of these films was 0.4 mm. XPS analysis was performed on films cast in aluminum weighing pans. The C=C group conversion was monitored by FTIR, and performed on films prepared on KBr disks. The average thickness of the latter two films was about 0.03 mm. Gel content: 56.3% Contact angle: spread and detached in about 4.5 minutes, with an average angle of detached droplet=71°. DSC: negative heat flow −67° C. TGA: 2 onset points: (A) 240.8° C., 34.09% mass loss, (B) 417.5° C., 62.99% mass loss. XPS: C: 56.2%, N: 3.80%, O: 14.14%, F: 25.79%.

Example 17: Homo Cross-Linked Films of Compound 4 Prepared by UV Cure

Compound 4 (0.4056 g) and HMP (0.0022 g) were weighed in a 20 mL vial. A small amount of MeOH (HPLC grade, 0.3 g) was added to the vial to reduce the viscosity of the mixture and to ensure good mixing. The vial was vortexed until all components were well mixed. The mixture was cast onto various substrates including stainless steel discs, an aluminum weighing pan and a KBr disc. MeOH solvent was allowed to evaporate at room temperature for 1 h under an aluminum foil. The stainless steel substrates, aluminum weighing pans and KBr disc containing opaque liquid samples were placed in the center of the UV box. The box was purged with argon gas for 10 minutes before the UV lamp was turned on for 5 minutes. All substrates were removed from the box and cooled to room temperature before carrying out film analysis. Gel content, swell ratio, contact angle measurements, DSC and TGA analysis were performed on films prepared on stainless steel discs. The typical thickness of these films was 0.4 mm. XPS analysis was performed on films cast in aluminum weighing pans. The C=C group conversion was monitored by FTIR, and performed on films prepared on KBr disks. The average thickness of the latter two films was about 0.03 mm. Gel extraction analysis (acetone): 56.3% gel, 550% swelling. Contact angle: Spreading as water droplet contact the surface and detached from the needle in about 1 minute. DSC: negative heat flow −68° C. TGA: 2 onset points: (A) 288.4° C., 31.4% mass loss, (B) 411.8° C., 67.2% mass loss. XPS: C: 58.31%, N: 2.86%, O: 15.97%, F: 21.89%.

Example 18: Homo Cross-Linked Films of Compound 10 Prepared by UV Cure

Compound 10 (3.9782 g) and HMP (0.0191 g) were weighed in a 20 mL vial. DCM (6 g) was added to the vial to reduce the viscosity of the mixture and to ensure good mixing. The vial was vortexed until all components were well mixed. The solution appeared transparent. If air bubbles appeared, the vial was allowed to sit at room temperature until all bubbles dissipated, before the mixture was cast onto the desired substrates such as Teflon molds, stainless steel discs, an aluminum weighing pan and a KBr disc. DCM solvent was allowed to evaporate at room temperature for 1 hour or 24 hours under an aluminum foil. After 1 hour, the stainless steel discs, aluminum weighing pan and KBr disc containing liquid samples were placed in the center of the UV box. Samples appeared transparent. The box was purged with argon gas for 10 minutes before the UV lamp was turned on for 5 minutes. All substrates were removed from the box and cooled to room temperature before carrying out film analysis. After 24 hours, the UV cure procedure was repeated for samples cast on Teflon molds. Film characteristics were recorded.

Example 19: Homo Cross-Linked Films of Compound 2 Prepared by Heat Cure with a Range of BPO Initiator Concentration A range of BPO concentrations (0, 0.05, 0.1, 0.5, and 1 wt % BPO) were evaluated for effectiveness of cure of Compound 2. Compound 2 was dissolved in toluene (0.1 g/mL) prepared with BPO (0, 0.05, 0.1, 0.5, and 1 wt %). 500 µL of these solutions were cast into 4 mL glass vials, the toluene was evaporated off at room temperature, and the films were cured at 60° C. in an $N_2$ purged oven. Films prepared with 0, 0.05, and 0.1 wt % BPO content did not cure enough to permit physical manipulation. Films prepared with 0.5 and 1 wt % BPO were analyzed for gel content (acetone extraction): 1 wt % BPO film (100% gel), 0.5 wt % BPO film (58% gel). Equivalent films were also prepared on KBr disks using 25 µL of the polymer solutions, and these films were analyzed by FTIR. The films prepared with 0-0.1 wt % BPO have signal at 1634 $cm^{-1}$ (C=C peak), whereas films prepared with 0.5 and 1 wt % BPO have no visible 1634 $cm^{-1}$ signal.

Figure 2:
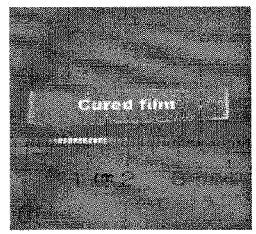
FIG. 2 is an image of a heat cured film of Compound 2, demonstrating Compound 2 processing capability.

Larger films of Compound 2 with 1 wt % BPO initiator were prepared for further analysis. Compound 2 was dissolved in toluene (0.1 g/mL) containing BPO initiator (1 mg, 1 wt % of Compound 2 mass). The toluene solution was cast into a 4 cm×4 cm PTFE wells (6 mL per well), and the PTFE casting plate was placed in a semi-enclosed chamber at room temperature for 1 day. The Compound 2 films were then cured for 12 hours in an $N_2$ purged 60° C. oven. The resulting films were clear and elastomeric (FIG. 2). Gel extraction analysis (acetone): 95% gel, 129% swelling. Contact angle analysis: water: 118°, porcine plasma: 113°, porcine blood: 121°. XPS analysis (90°): (top surface: C: 41.4%, N: 1.1%, O: 9.9%, F: 45.4%.) (bottom surface: C: 46.3%, N: 2.2%, O: 11.1%, F: 39.5%). DSC analysis: Tg=−69° C. TGA analysis: decomposition onset at 174° C.

Films of Compound 2 were prepared with 1 wt % V-70 initiator, and were cured in the same manner as the BPO cured film. By DSC analysis, the V-70 was found to be an effective initiator.

Figure 3:
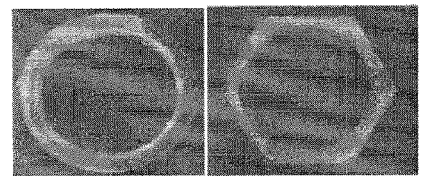
FIG. 3 is an image of heat cured shaped articles of Compound 2, showing how an article can be made from Compound 2.

Shaped articles of Compound 2 were prepared. Compound 2 was dissolved in toluene (0.1 g/mL) containing BPO initiator (1 mg, 1 wt % of Compound 2 mass). The toluene solution was cast into circular and hexagonal molds, and the molds were placed in a semi-enclosed chamber at room temperature for 1 day. The Compound 2 films were then cured for 12 hours in an $N_2$ purged 60° C. oven. The resulting shaped articles could be removed from the molds, and were elastomeric (FIG. 3).

Example 20: Homo Cross-Linked Films of Compound 6 Prepared by Heat Cure

Compound 6 was dissolved in toluene (0.1 g/mL) prepared with BPO (0, 0.05, 0.1, 0.5, and 1 wt %). 1.5 mL of each solution were cast into 24 mL glass vials, the toluene was evaporated off at room temperature, and the films were cured at 60° C. in an $N_2$ purged oven. All films excepting the 0% BPO film were firm and clear. The film prepared with 0% BPO was soft and tacky. Gel content (acetone extraction): 0 wt % BPO film (completely dissolved), 0.05, 0.1, 0.5 and 1 wt % BPO films (>99% gel). The acetone extraction solutions were reduced to dryness, and analyzed by $^1H$ NMR (400 MHz, $CDCl_3$): all extractions had NMR signatures consistent with the Compound 6 spectra. The 0 and 0.05 wt % BPO film extraction spectra contained vinyl signals (5.80-6.40 ppm) consistent with un-cured Compound 6, whereas the remaining extraction spectra did not show evidence of vinyl chemistry. Extractions of films containing BPO also had weak signals at 7.1 and 8.1 ppm, suggestive of the BPO initiator. Cured films were also prepared on KBr disks using 25 µL of the above polymer solutions, and these films were analyzed by FTIR.

Figure 4:
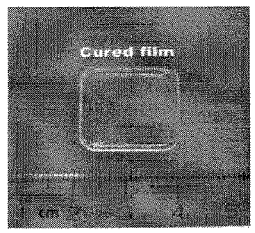
FIG. 4 is an image of a heat cured film of Compound 6, demonstrating Compound 6 processing capability.
Figure 5:
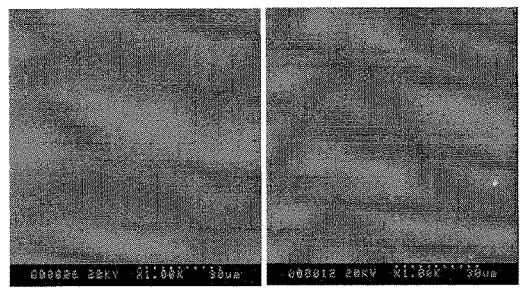
FIG. 5 is two SEM images of heat cured films of Compound 6, before and after toluene extraction, showing the final product properties to remain intact.

Larger films of Compound 6 with 1 wt % BPO were prepared for further analysis. Compound 6 films were prepared using 1 wt % BPO. Compound 6 was dissolved in toluene (0.05 or 0.1 g/mL) containing BPO initiator (1 wt % of Compound 6). The toluene solutions (6 mL) were cast into 4 cm×4 cm PTFE wells, and the PTFE casting plates were placed in a casting tank at room temperature for 1 day. The Compound 6 films were cured for 12 hours in an $N_2$ purged 60° C. oven. The resulting films were clear and elastomeric (FIG. 4). Gel content of 0.1 g/mL films (acetone extraction): 96% gel, 126% swelling. Gel content of 0.05 mg/mL films (toluene extraction): 92% gel, 193% swelling. Gel content of 0.1 mg/mL films (toluene extraction): >99% gel, 180% swelling. FIG. 5 shows films of cured Compound 6 prepared using the 0.05 and 0.1 g/mL solutions, before and after toluene exposure, indicating no change to film morphology. Contact angle analysis: water: 114°, porcine plasma: 119°, porcine blood: 116°. XPS analysis (90°): (top surface: C: 56.5%, N: 2.6%, O: 16.4%, F: 23.7%.) (bottom surface: C: 52.6%, N: 2.4%, O: 14.0%, F: 30.3%). DSC analysis: $T_g$=−65° C. TGA analysis: decomposition onset at 200° C. Tensile testing: stress at break=2.4 MPa, strain at break=42%. Films of Compound 6 were also prepared with 1 wt % V-70 initiator, and were cured in the same manner as the BPO cured film. By DSC analysis, the V-70 was found to be an effective initiator.

Example 21: Homo Cross-Linked Films of Compound 8 Prepared by Heat Cure

Compound 8 was dissolved in toluene (0.1 gram/mL) containing BPO (1 wt % of Compound 8). The toluene solution (6 mL) was cast into 4 cm×4 cm PTFE wells, and the PTFE casting plate was placed in a casting tank at room temperature for 1 day. The Compound 8 films were cured for 12 hours in an $N_2$ purged 60° C. oven. The resulting films were clear, tacky, and elastomeric. Gel extraction analysis: 91% gel, 117% swelling. Contact angle analysis: advancing angle: 119°. XPS analysis (90°): (top surface: C: 59.9%, N: 2.8%, O: 17.5%, F: 19.8%.) (bottom surface: C: 58.0%, N: 2.5%, O: 16.3%, F: 23%). Tensile testing: stress at break=1.5 MPa, strain at break=35%. Films of Compound 8 were also prepared with 1 wt % V-70 initiator, and were cured in the same manner as the BPO cured film. By DSC analysis, the V-70 was found to be an effective initiator.

Example 22: Homo Cross-Linked Films of Compound 12 Prepared by Heat Cure

Figure 6:
FIG. 6 is an image of a heat cured film of Compound 12, demonstrating Compound 12 processing capability.

Compound 12 was dissolved in THF (0.1 gram/mL) containing BPO (1 wt % of Compound 12). The THF solution (6 mL) was cast into 4 cm×4 cm PTFE wells, and the PTFE casting plate was placed in a casting tank at room temperature for 1 day. The Compound 12 films were cured for 12 hours in an $N_2$ purged 60° C. oven. The resulting films were translucent and elastomeric (FIG. 6). Gel extraction analysis (acetone): 97% gel, 136% swelling. Contact angle analysis: advancing angle: 118°. XPS analysis (90°): (top surface: C: 50.6%, N: 1.9%, O: 14.5%, F: 32.8%.) (bottom surface: C: 49.7%, N: 1.7%, O: 13.3%, F: 35.3%). Tensile testing: stress at break=2.0 MPa, strain at break=33%.

Cured System Based on Hetero Cross-Linking

Example 23: Hetero Cross-Linked Films of Blended Compound 2 and Compound 15, Prepared by UV Cure Compound 2 (2.0311 g), Compound 15 (2.0345 g) and HMP (0.0195 g) were weighed in a 20 mL vial. MeOH (HPLC grade, 5 g) was added to the vial to reduce the viscosity of the mixture and to ensure good mixing. The vial was vortexed until the compounds were all very well mixed. If air bubbles appeared, the vial was allowed to sit at room temperature until all bubbles dissipated, before the mixture was cast onto the desired substrates (Teflon molds, stainless steel discs, an aluminum weighing pan and a KBr disc). The solution appeared transparent. MeOH solvent was allowed to evaporate at room temperature for 1 hour and 24 hours under an aluminum foil. All films appeared opaque. The stainless steel substrates, aluminum weighing pans and KBr disc containing opaque liquid samples were placed in the center of the UV box. The box was purged with argon gas for 10 minutes before the UV lamp was turned on for 5 minutes. All substrates were removed from the box and cooled to room temperature before carrying out film analysis. After 24 hours, the UV cure procedure was repeated to samples cast on Teflon molds. Gel content, swell ratio, contact angle measurements, and TGA analysis were performed on films prepared on stainless steel discs. The typical thickness of these films was 0.4 mm. XPS analysis was performed on films cast in aluminum weighing pans. The C=C group conversion was monitored by FTIR, and performed on films prepared on KBr disc. The average thickness of these latter two films was about 0.03 mm. For tensile measurements, opaque polymer films free of air bubbles were removed from the molds and cut into to dog-bone shape. The dog-bone samples were air-tightened on an instron machine for subsequent tensile test measurements. An Instron 4301 system was used to test the samples with a cross-head load of 50 N at the rate of 10 mm/min, at 23° C. and relative humidity of 57%. Sample thickness measured by a caliber ranged from 0.1 to 0.3 mm. The results of each example represented an average of 5 dog-bone samples.

TABLE 3

Comparison of film properties prepared from a blend of Compound 2 and Compound 15 to films prepared from Compound 15 itself. Photoinitiator concentration in both systems was kept at 0.5 wt %.

|  | Blend of Compound 2 and Compound 15 | Compound 15 |
|---|---|---|
| C=C conversion (%) | Recorded | Recorded |
| Gel content (%) | 83 | 88 |
| Contact angle (°) | From 138 down to 75 in 5 minutes. Remained intact after 5 minutes | 104.1 ± 2.8 |
| XPS | C: 51.45%, N: 4.56%, O: 11.92%, F: 31.98%. | C: 52.89%, N: 3.47%, O: 21.55%, F: 0%. |
| DSC | $T_g$ = −68.70° C. | $T_g$ = −67.37° C. |
| TGA | 264.1° C., 20% mass loss | 273.8° C., 12% mass loss |
|  | 411.4° C., 75% mass loss | 406.9° C., 84% mass loss |
| Tensile testing | Stress at break = 1.4 MPa | Stress at break = 1.2 MPa |
|  | Strain at break = 32.3% | Strain at break = 36.5% |

Example 24: Hetero Cross-Linked Films of Blended Compound 2 and Compound 10, Prepared by UV Cure Compound 10 (1.9639 g), Compound 2 (2.0037 g), and HMP (0.0221 g) were weighed in a 20 mL vial. DCM (5 g) was added to the vial and the vial was vortexed until all components were well dissolved. The solution appeared translucent and exhibited phase separating. Diethyl ether (4 g) was then added to the vial, and the vial was vortexed and allowed to sit at room temperature. Again, phase separation occurred. The mixture was cast onto the desired substrates such as Teflon molds, stainless steel discs, an aluminum weighing pan and a KBr disc. DCM and diethyl ether solvents were allowed to evaporate at room temperature for 1 hour or 24 hours under an aluminum foil. After 1 hour, the stainless steel discs, aluminum weighing pan and KBr disc containing liquid samples were placed in the center of the UV box. Samples on all substrates appeared clear with visual droplets. The box was purged with argon gas for 10 minutes before the UV lamp was turned on for 5 minutes. All substrates were removed from the box and cooled to room temperature before carrying out film analysis. After 24 hours, the UV cure procedure was repeated for samples cast on Teflon molds.

Example 25: Hetero Cross-Linked Films of Blended Compound 2 and Vinyl Pyrrolidone, Prepared by UV Cure Compound 2 (2.9929 g), vinyl pyrrolidone (0.9822 g), HMP (0.0191 g) and MeOH (HPLC grade, 5 g) were weighed in to a 20 mL vial. The vial was vortexed until all contents was well mixed. If air bubbles appeared, the vial was allowed to sit at room temperature until all bubbles dissipated before the mixture was cast on Teflon molds, stainless steel substrates, an aluminum weighing pan and a KBr disc. MeOH solvent was allowed to evaporate at room temperature for 1 hour or 24 hours under an aluminum foil. After 1 hour, the stainless steel discs, aluminum weighing pan and KBr disc containing liquid samples were placed in the center of the UV box. The box was purged with argon gas for 10 minutes before the UV lamp was turned on for 5 minutes. All substrates were removed from the box and cooled to room temperature before carrying out film analysis. After 24 hours, the UV cure procedure was repeated to samples cast on Teflon molds. Gel content, swell ratio, contact angle measurements and TGA analysis were performed on films prepared on the stainless steel substrates. The typical thickness of these films was 0.4 mm. XPS analysis was performed on films cast on aluminum weighing pans (0.03 mm thick). Gel extraction analysis: 85% gel, 180% swelling. Contact angle: 134.5°±2.1. TGA: 2 onset points: (A) 293.2° C., 25.9% mass loss, (B) 418.2° C., 68.5% mass loss. FTIR analysis: the elimination of the C=C group was monitored to observe the polymerization of the materials prepared on the KBr disc. Tensile testing: stress at break=7.3 MPa, strain at break=69.8%. XPS analysis (90°): C: 47.65%, N: 3.45%, O: 10.53%, F: 38.42%.

Example 26: Hetero Cross-Linked Films of Blended Compound 2 and HEMA, Prepared by UV Cure Compound 2 (0.4003 g), HEMA (0.1485 g) and HMP (0.0033 g) were weighed in to a 20 mL vial. The vial was vortexed until Compound 2 was completely dissolved. If air bubbles appeared, the vial was allowed to sit at room temperature until all bubbles dissipated, before the mixture was cast onto the desired substrates (stainless steel discs, an aluminum weighing pan and a KBr disc). The stainless steel substrates, weighing pans and KBr disc containing liquid samples were placed in the center of the UV box. The box was purged with argon gas for 10 minutes before the UV lamp was turned on for 5 minutes. All substrates were removed from the box and cooled to room temperature before carrying out film analysis. Gel content, swell ratio, contact angle measurements and TGA analysis were performed on films prepared on the stainless steel substrates. The typical thickness of these films was 0.4 mm. XPS analysis was performed on films cast on aluminum weighing pans (0.03 mm thick). Gel extraction analysis: 90.3% gel, 192% swelling. Contact angle: The water droplet spread quickly on the film surface and detached from the needle in about 1 minute. The contact angle of the detached droplet is about 65°±2 (n=3). DSC: Tg=10.3° C. TGA: 2 onset points: (A) 299.4° C., 27.8% mass loss, (B) 414.7° C., 66.1% mass loss. IR: the C=C group conversion was monitored by FTIR and performed on films prepared on the KBr disc. XPS analysis (90°): C: 50.94%, N: 3.38%, O: 11.41%, F: 34.27%.

Example 27: Hetero Cross-Linked Films of Blended Compound 2 and Methacrylic Acid, Prepared by UV Cure Compound 2 (0.4047 g), MAA (0.1321 g) and HMP (0.0035 g) were weighed in to a 20 mL vial. The vial was vortexed until Compound 2 was completely dissolved. If air bubbles appeared, the vial was allowed to sit at room temperature until all bubbles dissipated, before the mixture was cast onto desired substrates (stainless steel discs, an aluminum weighing pan and a KBr disc). The stainless steel substrates, aluminum weighing pan and KBr disc containing liquid samples were placed in the center of the UV box. The box was purged with an argon gas for 10 minutes before the UV lamp was turned on for 5 minutes. All substrates were removed from the box and cooled to room temperature before carrying out film analysis. Gel content, swell ratio, contact angle measurements, DSC and TGA analysis were performed on films prepared on stainless steel substrates. The typical thickness of these films was 0.4 mm. Gel extraction analysis: 91.4% gel, 175% swelling. Contact angle: The water droplet spread on the film surface and detached from the needle in about 5 minutes. The contact angle of the detached droplet is about 74°±1 (n=4). DSC: 1$^{st}$ heat: negative heat flow at 23.5° C. This represents a shift in the $T_g$ of pure PTMO polymers (~-70° C.) towards that of pure MAA polymers ($T_g$ of ~228° C.). TGA: 2 onset points: (A) 234.9° C., 30.2% mass loss, (B) 407.4° C., 65.5% mass loss. IR: The C=C group conversion was monitored by FTIR and performed on films prepared on KBr discs.

Example 28: Hetero Cross-Linked Films of Blended Compound 2 and Methyl Methacrylate, Prepared by UV Cure Compound 2 (3.0335 g), MMA (3.0182 g) and HMP (0.0200 g) were weighed in to a 20 mL vial. The vial was vortexed until Compound 2 was completely dissolved. If air bubbles appeared, the vial was allowed to sit at room temperature until all bubbles dissipated, before the mixture was cast onto the desired substrates (Teflon molds, stainless steel substrates, an aluminum weighing pan and a KBr disc). The Teflon molds, stainless steel substrates, weighing pans and KBr disc containing liquid samples were placed in the center of the UV box. The box was purged with an argon gas for 1 minute before the UV lamp was turned on for 5 minutes. All substrates were removed from the box and cooled to room temperature before carrying out film analysis. Gel content, swell ratio, contact angle measurements and TGA analysis were performed on films prepared on the stainless steel substrates. The typical thickness of these films was 0.4 mm. XPS analysis was performed on films cast on aluminum weighing pans (0.03 mm thick). Gel extraction analysis: 93.5% gel, 230% swelling. Contact angle: 132.9°±2.2. TGA: 2 onset points: (A) 296.5° C., 27.4% mass loss, (B) 411.4° C., 69.5% mass loss. IR: the C=C group conversion was monitored by FTIR and performed on films prepared on the KBr discs. Tensile testing: stress at yield=9.2 MPa, stress at break=13.6 MPa, strain at break=9.9%. XPS analysis (90°): C: 47.5%, N: 3.93%, O: 11.02%, F: 37.45%.

Example 28': Hetero Cross-Linked Films of Blended Compound 2 and TEGMA, Prepared by UV Cure Compound 2 (0.37500 g), TEGDMA (0.1250 g) and HMP (0.005 g) were weighed in to a 20 mL vial. The vial was vortexed until Compound 2 was completely dissolved. If air bubbles appeared, the vial was allowed to sit at room temperature until all bubbles dissipated, before the mixture was cast onto the desired substrates (stainless steel substrates, an aluminum weighing pan and a KBr disc). The stainless steel substrates, weighing pans and KBr disc containing liquid samples were placed in the center of the UV box. The box was purged with an argon gas for 1 minute before the UV lamp was turned on for 5 minutes. All substrates were removed from the box and cooled to room temperature before carrying out film analysis. Gel content, swell ratio, contact angle measurements and TGA analysis were performed on films prepared on stainless steel substrates. The typical thickness of these films is 0.4 mm. XPS analysis was performed on films cast on aluminum weighing pans (0.03 mm thick). Gel extraction analysis: 89.8% gel, 140% swelling. Contact angle: spread quickly. TGA: 246.5° C., 97.35% mass loss. IR: the C=C group conversion was monitored by FTIR performed on films cast on KBr disks. XPS analysis (90°): C: 49.07%, N: 3.14%, O: 12.56%, F: 35.22%.

Example 29: Hetero Cross-Linked Films of Compound 2 and SIBS Polymer, Prepared by UV Cure SIBS solution (0.5 g/mL in toluene) was cast on stainless steel substrates and an aluminum weighing pan. The toluene was allowed to evaporate at room temperature overnight. In a 20 mL vial, Compound 2, HMP, and MeOH (HPLC grade) were weighed. The vial was vortexed until the components were completely well blended. If air bubbles appeared, the vial was allowed to sit at room temperature until all bubbles dissipated The Compound 2 solution was transferred from the vial to a 50 mL HDPE spraying bottle. The spraying bottle was used to deposit a thin layer of Compound 2 and HMP on top of the SIBS film. MeOH solvent was allowed to evaporate at room temperature for 1 hour under an aluminum foil. The stainless steel substrates and weighing pans containing SIBS films coated with Compound 2 and HMP were placed in the center of the UV box. The box was purged with an argon gas for 5 minutes before the UV lamp was turned on for 5 minutes. All substrates were removed from the box and cooled to room temperature before carrying out film analysis. Contact angle: 128°. XPS analysis (90°): (SIBS) C: 98.90%, N: 0.18%, O: 0.45%, F: 0.47%. (SIBS+Compound 2) C: 53.50%, N: 3.95%, O: 15.11%, F: 27.63%.

Example 30: Hetero Cross-Linked Films of Compound 2 and EVA Polymer, Prepared by UV Cure EVA solution (0.5 g/mL in toluene) was cast on stainless steel substrates and an aluminum weighing pan. The toluene was allowed to evaporate at room temperature overnight. In a 20 mL vial, Compound 2, HMP, and MeOH (HPLC grade) were weighed. The vial was vortexed until the components were completely well blended. If air bubbles appeared, the vial is allowed to sit at room temperature until all bubbles dissipated. The Compound 2 solution was transferred from the vial to a 50 mL HDPE spraying bottle. The spraying bottle was used to deposit a thin layer of Compound 2 and HMP on top of the EVA film. MeOH solvent was allowed to evaporate at room temperature for 1 hour under an aluminum foil. The stainless steel substrates and weighing pans containing EVA films coated with Compound 2 and HMP were placed in the center of the UV box. The box was purged with an argon gas for 5 minutes before the UV lamp was turned on for 5 minutes. All substrates were removed from the box and cooled to room temperature before carrying out film analysis. Contact angle: 1260. XPS analysis (900): (EVA) C: 84.61%, N: 4.03%, O: 11.36%, F: 0%. (EVA+Compound 2) C: 72.72%, N: 4.08%, O: 12.59%, F: 10.21%.

Example 31: Hetero Cross-Linked Films Prepared with a Mixture of Compound 2 and Compound 6

Figure 7:
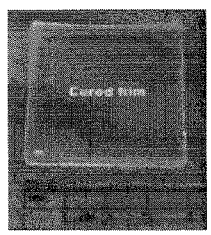
FIG. 7 is an image of a heat cured film of Compound 2 and Compound 6, showing Compound 2 and Compound 6 processing capability.

Compound 2 (0.3 g) was dissolved in toluene (0.1 g/mL) containing BPO (3 mg, 1 wt % of Compound 2 mass). Compound 6 (0.3 g) was dissolved in toluene (0.1 g/mL) containing BPO (3 mg, 1 wt % of Compound 6 mass). These two solutions were mixed in a 50:50 ratio, and 6 mL of this combined solution were cast into 4 cm×4 cm PTFE wells. The PTFE casting plate was placed in a semi-enclosed chamber at room temperature for 1 day. The film was then cured for 12 hours in an $N_2$ purged 60° C. oven. The resulting film was clear, elastomeric, and non-tacky (FIG. 7). Gel extraction analysis (acetone): 96% gel, 141% swelling. Contact angle analysis: advancing angle: 1160. XPS analysis (90°): (top surface: C: 51.4%, N: 2.5%, O: 14.8%, F: 31.1%.) (bottom surface: C: 48.7%, N: 1.9%, O: 13.0%, F: 35.5%).

Example 32: Hetero Cross-Linked Films Prepared with a Combination of Compound 6 and Compound 8

Figure 8:
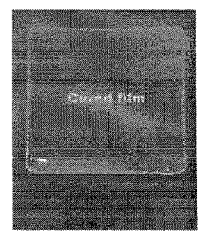
FIG. 8 is an image of a heat cured film of Compound 6 and Compound 8, showing Compound 6 and Compound 8 processing capability.

Compound 6 (0.3 g) was dissolved in toluene (0.1 g/mL) containing BPO (3 mg, 1 wt % of Compound 6 mass). Compound 8 (0.3 g) was dissolved in toluene (0.1 g/mL) containing BPO (3 mg, 1 wt % of Compound 8 mass). These two solutions were mixed in a 50:50 ratio, and 6 mL of this combined solution were cast into 4 cm×4 cm PTFE wells. The PTFE casting plate was placed in a semi-enclosed chamber at room temperature for 1 day. The film was then cured for 12 hours in an $N_2$ purged 60° C. oven. The resulting film was clear, elastomeric, resistant to tearing, and non-tacky (FIG. 8). Gel extraction analysis (acetone): 96% gel, 154% swelling. Contact angle analysis: advancing angle: 127°. XPS analysis (900): (top surface: C: 54.2%, N: 2.5%, O: 16.4%, F: 26.8%.) (bottom surface: C: 49.2%, N: 1.8%, O: 12.2%, F: 36.1%).

Example 33: Hetero Cross-Linked Films Prepared with a Combination of Compound 6 and a Vinyl Monomer (FEO1)

Figure 9:
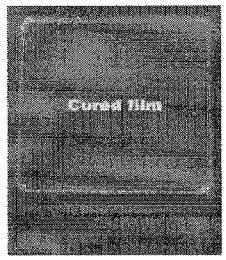
FIG. 9 is an image of a heat cured film of Compound 6 and FEO1, demonstrating Compound 6 processing capability.

Compound 6 (0.3 g) was dissolved in toluene (0.1 g/mL) containing BPO (3 mg, 1 wt % of Compound 6 mass). FEO1 (0.3 g) was dissolved in toluene (0.1 g/mL) containing BPO (3 mg, 1 wt % of FEO1 mass). These two solutions were mixed in a 50:50 ratio, and 6 mL of this combined solution were cast into 4 cm×4 cm PTFE wells. The PTFE casting plate was placed in a semi-enclosed chamber at room temperature for 1 day. The film was then cured for 12 hours in an $N_2$ purged 60° C. oven. The resulting film was clear, elastomeric, resistant to tearing, and non-tacky (FIG. 9). Gel extraction analysis (acetone): 93% gel, 133% swelling. Contact angle analysis: advancing angle: 104°. XPS analysis (90°): (top surface: C: 47.8%, N: 1.0%, O: 13.4%, F: 36.2%.) (bottom surface: C: 46.2%, N: 0.6%, O: 11.7%, F: 39.0%).

Example 34: Hetero Cross-Linked Films Prepared with a Combination of Compound 6 and a Vinyl Monomer (HEMA)

Figure 10:
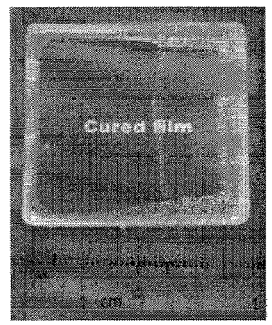
FIG. 10 is an image of a heat cured film of Compound 6 and HEMA, showing Compound 6 processing capability.

Compound 6 (0.3 g) was dissolved in toluene (0.1 g/mL) containing BPO (3 mg, 1 wt % of Compound 6 mass). HEMA (0.3 g) was dissolved in toluene (0.1 g/mL) containing BPO (3 mg, 1 wt % of HEMA mass). These two solutions were mixed in a 50:50 ratio, and 6 mL of this combined solution were cast into 4 cm×4 cm PTFE wells. The PTFE casting plate was placed in a semi-enclosed chamber at room temperature for 1 day. The film was then cured for 12 hours in an $N_2$ purged 60° C. oven. The resulting cured material was tough and opaque (FIG. 10). Gel extraction analysis (acetone): 93% gel, 153% swelling. XPS analysis (900): (top surface: C: 53.4%, N: 2.5%, O: 16.2%, F: 27.2%.) (bottom surface: C: 51.1%, N: 1.8%, O: 13.1%, F: 33.8%).

Example 35: Hetero Cross-Linked Films Prepared with a Combination of Compound 2 and Compound 1

Compound 2 (0.1 g) was dissolved in toluene (0.1 g/mL) containing BPO (1 mg, 1 wt % of Compound 2 mass).

Compound 1-ester (0.1 g) was dissolved in toluene (0.1 g/mL) containing BPO (1 mg, 1 wt % of Compound 1-ester mass). These two solutions were mixed in a 50:50 ratio, and 2 mL of this combined solution were cast into 2 cm×2 cm PTFE wells. The PTFE casting plate was placed in a semi-enclosed chamber at room temperature for 1 day. The film was then cured for 12 hours in an $N_2$ purged 60° C. oven. The resulting cured material was homogeneous and firm. Gel extraction analysis (acetone): 87% gel. XPS analysis (90°): top surface: C: 41.4%, N: 1.1%, O: 9.9%, F: 45.4%.

Example 36: Homo Cross-Linked Films Prepared Using HEMA Monomer

HEMA (0.6 g) was dissolved in toluene (6 mL, 0.1 g/mL) containing BPO (6 mg, 1 wt % of HEMA mass), and this solution was cast into a 4 cm×4 cm PTFE well. The PTFE casting plate was placed in a semi-enclosed chamber at room temperature for 1 day. The film was then cured for 12 hours in an $N_2$ purged 60° C. oven. The resulting cured material was hard and inconsistent in thickness. Gel extraction analysis (acetone): >99% gel, 136% swelling.

Example 37: Homo Cross-Linked Films Prepared Using FEO1 Monomer

FEO1 (0.6 g) was dissolved in toluene (6 mL, 0.1 g/mL) containing BPO (6 mg, 1 wt % of FEO1 mass), and this solution was cast into a 4 cm×4 cm PTFE well. The PTFE casting plate was placed in a semi-enclosed chamber at room temperature for 1 day. The film was then cured for 12 hours in an $N_2$ purged 60° C. oven. The resulting cured material was hard and inconsistent in thickness. Gel extraction analysis (acetone): 84% gel.

Example 38: Hetero Cross-Linked Films Prepared Using a Blend of Compound 1 and HEMA Monomer Compound 1-ester (0.3 g) was dissolved in toluene (0.1 g/mL) containing BPO (3 mg, 1 wt % of Compound 1-ester mass). HEMA (0.3 g) was dissolved in toluene (0.1 g/mL) containing BPO (3 mg, 1 wt % of HEMA mass). These two solutions were mixed in a 50:50 ratio, and 6 mL of this combined solution were cast into 4 cm×4 cm PTFE wells. The PTFE casting plate was placed in a semi-enclosed chamber at room temperature for 1 day. The film was cured for 12 hours in an $N_2$ purged 60° C. oven. The resulting cured material was more firm than pure Compound 1 but shrank within the casting form, and was too soft to handle as a film.

Example 39: Hetero Cross-Linked Films Prepared Using a Blend of Compound 1 and FEO1 Monomer Compound 1-ester (0.3 g) was dissolved in toluene (0.1 g/mL) containing BPO (3 mg, 1 wt % of Compound 1-ester mass). FEO1 (0.3 g) was dissolved in toluene (0.1 g/mL) containing BPO (3 mg, 1 wt % of FEO1 mass). These two solutions were mixed in a 50:50 ratio, and 6 mL of this combined solution were cast into 4 cm×4 cm PTFE wells. The PTFE casting plate was placed in a semi-enclosed chamber at room temperature for 1 day. The film was then cured for 12 hours in an $N_2$ purged 60° C. oven. The resulting cured material was firm and even-looking within the casting form, but was too soft to handle as a film.

Polymerization on a Stent Platform

Figure 11:
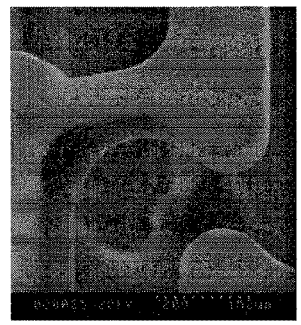
FIG. 11 is an image of a stent coated with heat cured Compound 2, showing good coverage with minimal webbing.
Figure 12:
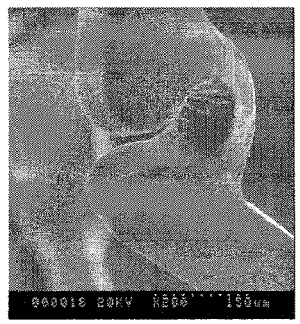
FIG. 12 is an image of an air-deployed stent, coated with heat cured Compound 2, showing good coverage with minimal webbing.

Example 40: Coating of Compound 2 on a Stent, Prepared by Spraying and Heat Cure Compound 2 (200 mg) was dissolved in toluene (4 mL, 0.05 g/mL), stirred for 90 minutes at room temperature and BPO (2 mg, 1 wt % of Compound 2 mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 11) indicated that the stents were uniformly coated. In addition, a Compound 2 coated stent was crimped on a balloon and deployed at 10 psi. Coating remained intact (FIG. 12).

Figure 13:
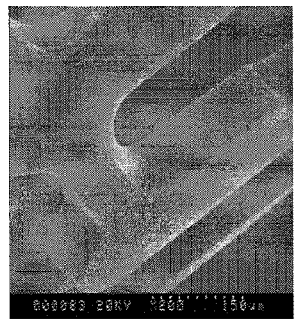
FIG. 13 is an image of a stent coated with heat cured Compound 6, demonstrating good coverage with minimal webbing.
Figure 14:
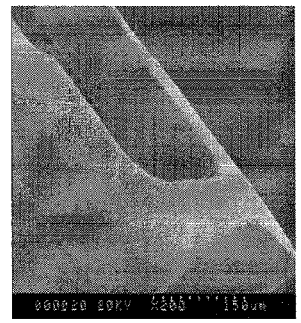
FIG. 14 is an image of a stent coated with heat cured Compound 6, extracted with toluene, demonstrating the final product properties to remain intact.
Figure 15:
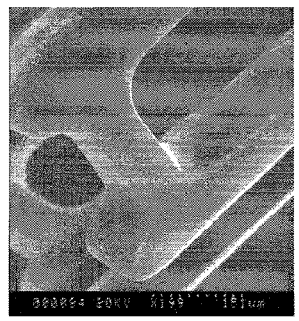
FIG. 15 is an image of a stent coated with heat cured Compound 6, extracted with buffer, showing the final product properties to remain intact.

Example 41: Coating of Compound 6 on a Stent, Prepared by Spraying and Heat Cure Compound 6 (200 mg) was dissolved in toluene (4 mL, 0.05 g/mL), stirred for 90 minutes at room temperature and BPO (2 mg, 1 wt % of Compound 6 mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 13) indicated that the stents were uniformly coated. A Compound 6 coated stent was extracted with toluene after curing for 24 hrs and SEM images suggested that the coating remained intact after solvent extraction (FIG. 14). In addition, Compound 6 coated stent was also extracted in PBS 7.4 buffer for 24 hrs and SEM images suggested that the coating remained intact after buffer extraction (FIG. 15).

Figure 16:
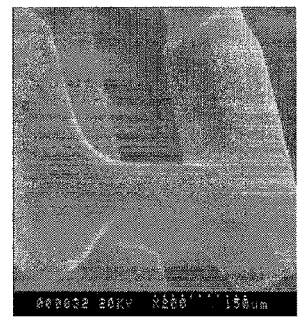
FIG. 16 is an image of a stent coated with heat cured Compound 8, demonstrating good coverage with minimal webbing.

Example 42: Coating of Compound 8 on a Stent, Prepared by Spraying and Heat Cure Compound 8 (200 mg) was dissolved in toluene (4 mL, 0.05 g/mL), stirred for 90 minutes at room temperature and BPO (2 mg, 1 wt % of Compound 8 mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 16) indicated that the stents were uniformly coated.

Example 43: Coating of Compound 12 on a Stent, Prepared by Spraying and Heat Cure (Toluene Solvent)

Figure 17:
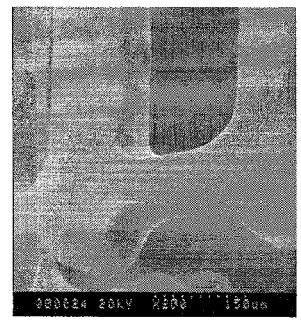
FIG. 17 is an image of a stent coated with heat cured Compound 12 (toluene solvent), showing good coverage with minimal webbing.

Compound 12 (200 mg) was dissolved in toluene (4 mL, 0.05 g/mL), stirred for 90 minutes at room temperature and BPO (2 mg, 1 wt % of Compound 12 mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 17) indicated that the stents showed decent coating.

Example 44: Coating of Compound 12 on a Stent, Prepared by Spraying and Heat Cure (Toluene/THF Solvent)

Figure 18:
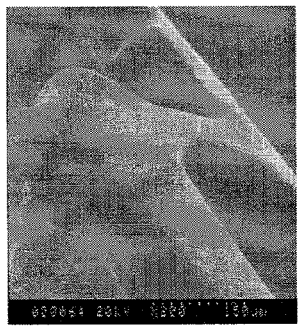
FIG. 18 is an image of a stent coated with heat cured Compound 12 (toluene:THF solvent), showing good coverage with minimal webbing.

Compound 12 (200 mg) was dissolved in 75:25 toluene: THF (4 mL, 0.05 g/mL), stirred for 90 minutes at room temperature and BPO (2 mg, 1 wt % of Compound 12 mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 18) indicated that the stents were uniformly coated.

Figure 19:
FIG. 19 is an image of a stent coated with heat cured Compound 2 and Compound 6, showing good coverage with minimal webbing.

Example 45: Coating of a Mixture of Compound 2 and Compound 6 on a Stent, Prepared by Spraying and Heat Cure Compound 2 and Compound 6 (1:1, total 200 mg) were dissolved in toluene (4 mL, 0.05 g/mL), stirred for 90 minutes at room temperature and BPO (2 mg, 1 wt % of Compound 2 and Compound 6 combined mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 19) indicated that the stents were uniformly coated.

Figure 20:
FIG. 20 is an image of a stent coated with heat cured Compound 6 and Compound 8, showing good coverage with minimal webbing.

Example 46: Coating of a Mixture of Compound 6 and Compound 8 on a Stent, Prepared by Spraying and Heat Cure Compound 6 and Compound 8 (1:1, total 200 mg) were dissolved in toluene (4 mL, 0.05 g/mL), stirred for 90 minutes at room temperature and BPO (2 mg, 1 wt % of Compound 6 and Compound 8 combined mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 20) indicated that the stents were uniformly coated.

Figure 21:
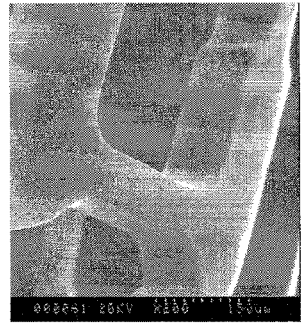
FIG. 21 is an image of a stent coated with heat cured Compound 6 and PTX, showing good coverage with minimal webbing.

Example 47: Coating of a Mixture of Compound 6 and Paclitaxel on a Stent, Prepared by Spraying and Heat Cure Compound 6 (200 mg) was dissolved in 75:25 toluene: THF (4 mL, 0.05 g/mL), stirred for 90 minutes at room temperature and Paclitaxel (17.6 mg, 8.8 wt % of Compound 6 mass) and BPO (2 mg, 1 wt % of Compound 6 mass) was added and the mixture was stirred for an additional 30 minutes. The solution blend was sprayed onto stents using an EFD spray system, and the coatings were cured at 60° C. in an $N_2$ purged oven for 12 hours. SEM analysis (FIG. 21) indicated that the stents were uniformly coated.

Biocompatibility Assays

Example 48: MEM Elution Assay of Compound 2

Samples of film from Example 19 (1 cm×2 cm) were weighed and incubated in MEM media for 24 hours. A counted aliquot of L-929 mouse fibroblast culture was seeded into each MEM extract, and stability of the cell population was evaluated after 24 hours using a trypan blue exclusion method. By this cytotoxicity evaluation method, the Compound 2 films were non-toxic.

Figure 27:
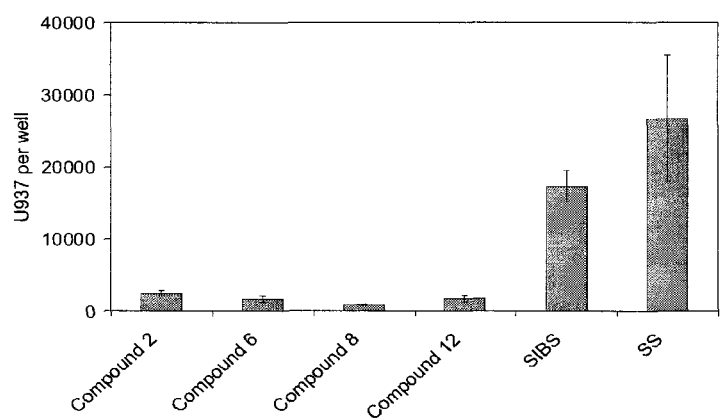
FIG. 27 is a plot of U937 adhesion to cured films of Compounds 2, 6, 8, and 12, cast on PP, demonstrating a significant reduction in cell adhesion profile.
Figure 28:
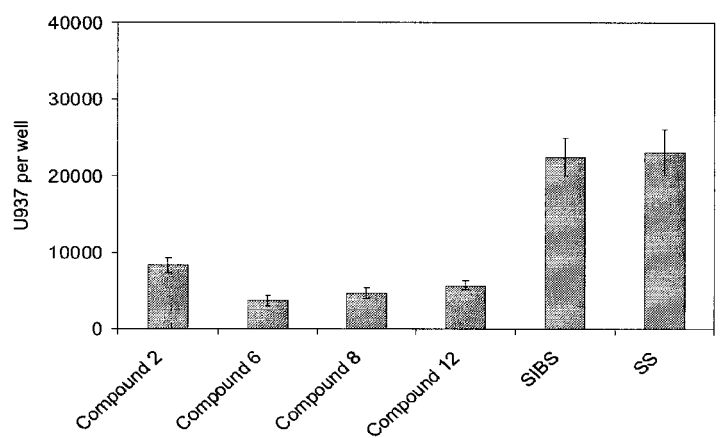
FIG. 28 is a plot of U937 adhesion to cured films of Compounds 2, 6, 8, and 12, cast on stainless steel, demonstrating a substantial reduction in cell adhesion profile.

Example 49: Homo Cross-Linked Films of Compound 2 Prepared by Heat Cure, Assessed for Inflammatory Cell Interaction Compound 2 was dissolved in toluene (0.1 g/mL) containing BPO initiator (1 wt % of Compound 2 mass). The toluene solution was cast into 96 well polypropylene plates (6 wells per plate), and the plates were placed in a semi-enclosed chamber at room temperature for 1 day. The Compound 2 films were then cured for 12 hours in an $N_2$ purged 60° C. oven, and vacuum dried. For comparison purposes, films of SIBS were cast in a second 96 well plate: a 0.1 g/mL toluene solution of SIBS was cast in 6 wells, the plates were placed in a semi-enclosed chamber at room temperature for 1 day, dried in a 60° C. oven for 1 day, and vacuum dried. Into the plate containing SIBS were inserted 316 stainless steel inserts. The plates were sterilized under a UV lamp for 1 hour, after which each sample well was hydrated using 200 uL PBS. Approximately $2.5\times10^5$ U937 monocyte-like cells were seeded onto each sample in the presence of PMA, and were incubated at 37° C. in a humid incubator for three days. The adherent U937 macrophages were enumerated using a CyQuant assay (FIG. 27). In a similar experiment, the Compound 2 and SIBS films were prepared on stainless steel inserts (FIG. 28).

Example 50: Cone-and-Plate Assay of Homo Cross-Linked Films of Compound 2

Figure 29:
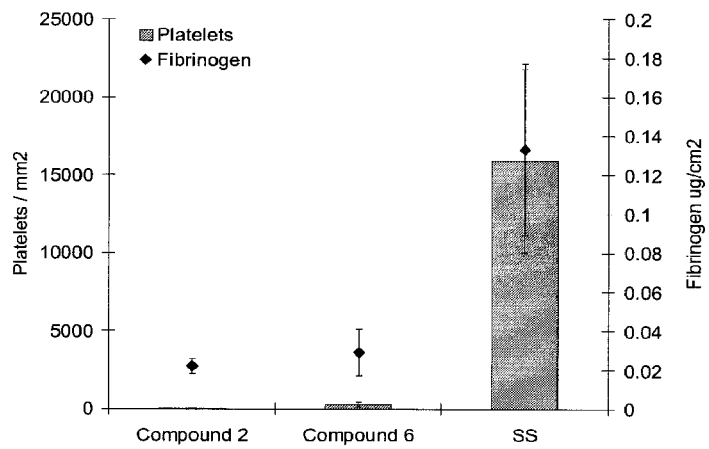
FIG. 29 is a plot of platelet and fibrinogen interaction with cured films of Compounds 2 and 6, showing a significant reduction in platelet adhesion and fibrinogen adsorption.

Samples of Compound 2 film from Example 19 and 316 stainless steel (4 cm×4 cm) were fixed into individual wells of a cone-and-plate device. A 1.2 mL aliquot of whole blood suspension containing $^{51}Cr$ labeled platelets (250 000 platelets/µL) and $^{125}I$ labeled fibrinogen was pipetted onto the films, and cones were lowered into each well and immediately rotated at 200 rpm for 15 minutes. The films were then removed, rinsed, and adherent platelets and fibrinogen quantified by a gamma counter (FIG. 29).

Example 51: MEM Elution Assay of Homo Cross-Linked Films of Compound 6

Samples of film from Example 20 (1 cm×2 cm) were weighed and incubated in MEM media for 24 hours. A counted aliquot of L-929 mouse fibroblast culture was seeded into each MEM extract, and stability of the cell population was evaluated after 24 hours using a trypan blue exclusion method. By this cytotoxicity evaluation method, the Compound 6 films were non-toxic.

Example 52: Homo Cross-Linked Films of Compound 6 Prepared by Heat Cure, Assessed for Inflammatory Cell Interaction Compound 6 was dissolved in toluene (0.1 g/mL) containing BPO initiator (1 wt % of Compound 6 mass). The toluene solution was cast into 96 well polypropylene plates (6 wells per plate), and the plates were placed in a semi-enclosed chamber at room temperature for 1 day. The Compound 6 films were then cured for 12 hours in an $N_2$ purged 60° C. oven, and vacuum dried. For comparison purposes, films of SIBS were cast in a second 96 well plate: a 0.1 g/mL toluene solution of SIBS was cast in 6 wells, the plates were placed in a semi-enclosed chamber at room temperature for 1 day, dried in a 60° C. oven for 1 day, and vacuum dried. Into the plate containing SIBS were also inserted 316 stainless steel inserts. The plates were sterilized under a UV lamp for 1 hour, after which each sample well was hydrated using 200 uL PBS. Approximately $2.5\times10^5$ U937 monocyte-like cells were seeded onto each sample in the presence of PMA, and were incubated at 37° C. in a humid incubator for three days. The adherent U937 macrophages were enumerated using a CyQuant assay (FIG. 27).

In a similar experiment, the Compound 6 and SIBS films were prepared on stainless steel inserts (FIG. 28).

Example 53: Cone-and-Plate Assay of Homo Cross-Linked Films of Compound 6

Samples of Compound 6 film from Example 20 and 316 stainless steel (4 cm×4 cm) were fixed into individual wells of a cone-and-plate device. A 1.2 mL aliquot of whole blood suspension containing $^{51}$Cr labeled platelets (250 000 platelets/μL) and $^{125}$I labeled fibrinogen was pipetted onto the films, and cones were lowered into each well and immediately rotated at 200 rpm for 15 minutes. The films were then removed, rinsed, and adherent platelets and fibrinogen quantified by a gamma counter (FIG. 29).

Example 54: Homo Cross-Linked Films of Compound 8 Prepared by Heat Cure, Assessed for Inflammatory Cell Interaction Compound 8 was dissolved in toluene (0.1 g/mL) containing BPO initiator (1 wt % of Compound 8 mass). The toluene solution was cast into 96 well polypropylene plates (6 wells per plate), and the plates were placed in a semi-enclosed chamber at room temperature for 1 day. The Compound 8 films were then cured for 12 hours in an N$_2$ purged 60° C. oven, and vacuum dried. For comparison purposes, films of SIBS were cast in a second 96 well plate: a 0.1 g/mL toluene solution of SIBS was cast in 6 wells, the plates were placed in a semi-enclosed chamber at room temperature for 1 day, dried in a 60° C. oven for 1 day, and vacuum dried. Into the plate containing SIBS were also inserted 316 stainless steel inserts. The plates were sterilized under a UV lamp for 1 hour, after which each sample well was hydrated using 200 uL PBS. Approximately 2.5×10$^5$ U937 monocyte-like cells were seeded onto each sample in the presence of PMA, and were incubated at 37° C. in a humid incubator for three days. The adherent U937 macrophages were enumerated using a CyQuant assay (FIG. 27). In a similar experiment, the Compound 8 and SIBS films were prepared on stainless steel inserts (FIG. 28).

Example 55: Homo Cross-Linked Films of Compound 12 Prepared by Heat Cure, Assessed for Inflammatory Cell Interaction Compound 12 was dissolved in toluene (0.1 g/mL) containing BPO initiator (1 wt % of Compound 12 mass). The toluene solution was cast into 96 well polypropylene plates (6 wells), and the plates were placed in a semi-enclosed chamber at room temperature for 1 day. The Compound 12 films were then cured for 12 hours in an N$_2$ purged 60° C. oven, and vacuum dried. For comparison purposes, films of SIBS were cast in a second 96 well plate: a 0.1 g/mL toluene solution of SIBS was cast in 6 wells, the plates were placed in a semi-enclosed chamber at room temperature for 1 day, dried in a 60° C. oven for 1 day, and vacuum dried. Into the plate containing SIBS were also inserted 316 stainless steel inserts. The plates were sterilized under a UV lamp for 1 hour, after which each sample well was hydrated using 200 uL PBS. Approximately 2.5×10$^5$ U937 monocyte-like cells were seeded onto each sample in the presence of PMA, and were incubated at 37° C. in a humid incubator for three days. The adherent U937 macrophages were enumerated using a CyQuant assay (FIG. 27). In a similar experiment, the Compound 12 and SIBS films were prepared on stainless steel inserts (FIG. 28).

Drug Inclusion and Release

Compounds from Section 1 provide a polymeric platform with functional groups suitable for the immobilization and inclusion of active agents. Compounds 6, 7, and 8 have functional groups for covalent interaction with active agents. Films or stent coatings including active agents are prepared according to Section 2 and 3 methods.

Example 56: Films of Compound 2 and Aspirin (90:10), UV Cure

Figure 22:
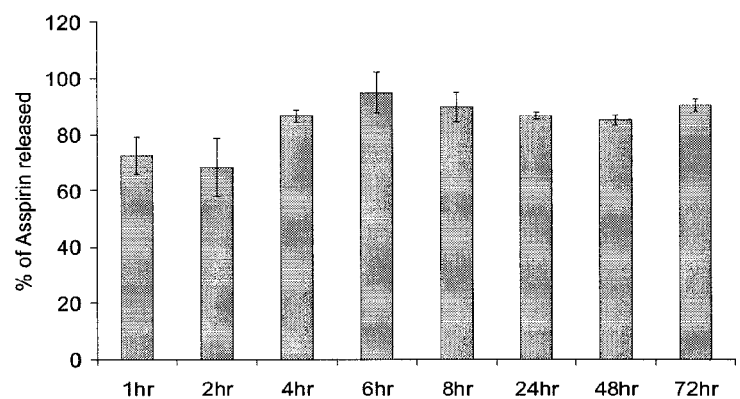
FIG. 22 is a plot of ASA release from a UV cured film of Compound 2 with 10 wt % ASA, showing the release of ASA from Compound 2.

Compound 2 (1.6481 g), ASA (0.1841 g), HMP (0.0088 g) and MeOH (HPLC grade, 4.01 g) were weighed in to a 20 mL vial. The vial was vortexed until all components were well mixed. If air bubbles appeared, the vial was allowed to sit at room temperature until all bubbles dissipated, before the mixture was cast onto desired substrates (stainless steel discs, an aluminum weighing pan and a KBr disc). The MeOH was evaporated off at room temperature for 1 and 24 hours under aluminum foil. After 1 hour, the stainless steel substrates, aluminum weighing pan and KBr disc containing liquid samples were placed in the center of the UV box. The box was purged with an argon gas for 10 minutes before the UV lamp was turned on for 2 minutes. All substrates were removed from the box and cooled to room temperature before carrying out film analysis. After 24 hours, the UV cure procedure was repeated for samples cast on Teflon substrates. Gel content, swell ratio, contact angle measurements, DSC and TGA analysis were performed on films prepared on stainless steel substrates. The typical thickness of these films was 0.4 mm. XPS analysis was performed on films cast on aluminum weighing pans (0.03 mm thick). Gel content: 82%, swelling=180%. Contact angle: 131.8°±2.0. DSC: negative heat flow at −64° C. (associated with the T$_g$ of PTMO). TGA: 2 onset points: (A) 234.9° C., 30.2% mass loss, (B) 407.4° C., 65.5% mass loss. IR: the C═C group conversion is monitored by FTIR and performed on films prepared on KBr discs. XPS: C: 50.68%, N: 3.02%, O: 12.00%, F: 34.31%. Aspirin release was examined for films cast in Teflon molds (FIG. 22).

Example 57: Films of Compound 2 and Aspirin (75:25), UV Cure

Figure 23:
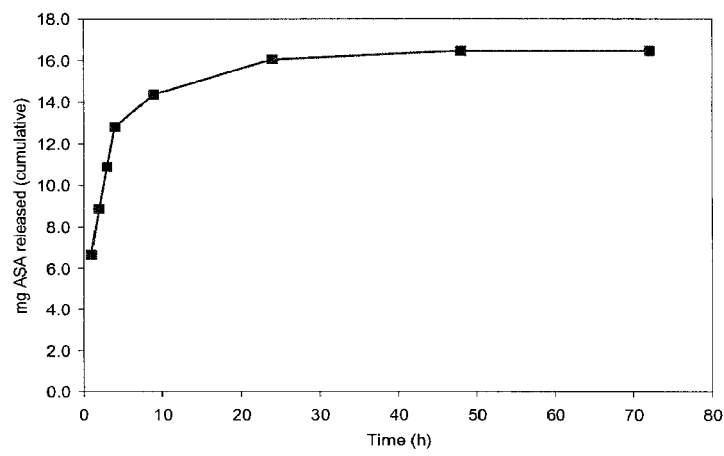
FIG. 23 is a plot of ASA release from a UV cured film of Compound 2 with 25 wt % ASA, showing the ability of ASA to be released from Compound 2.

Compound 2 (100 mg), HMP (1 mg) and ASA (33 mg) were dissolved in DMSO as a 2.5 g/mL solution. The solution was cast into a 4 mL glass vial and the material was cured under UV light for 2 minutes. The resulting clear elastomeric film was incubated in PBS solutions for 24 hours at 37° C., with measurement of ASA release made at 1, 2, 3, 4, 7 and 24 hours by UV spectrophotometer measurement (FIG. 23).

Example 58: Films of Compound 2 and Ibuprofen (75:25), Heat Cure

Figure 24:
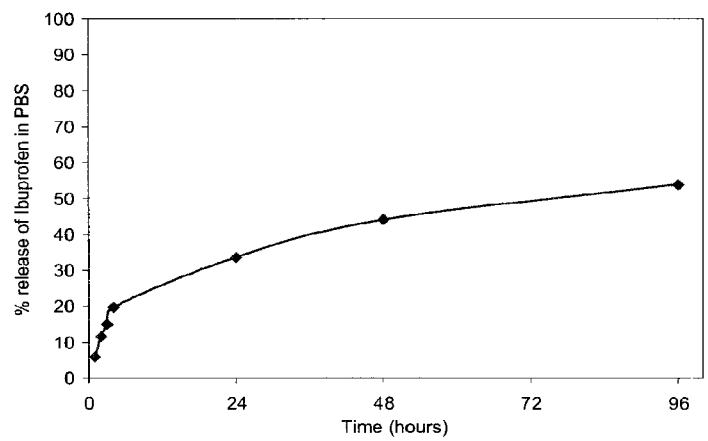
FIG. 24 is a plot of ibuprofen release from a heat cured film of Compound 2, demonstrating the ability of ibuprofen to be released from Compound 2.

Ibuprofen was mixed with Compound 2 (25 wt % of total mass) in toluene (0.1 gram/mL) containing BPO (1 wt %), and cured at 60° C. under N$_2$. The release of ibuprofen from the cured film was measured over 96 hours in PBS solution at 37° C. by UV spectrophotometer measurement (FIG. 24).

Example 59: Films of Compound 2 and Ciprofloxacin-HEMA (Compound 17)

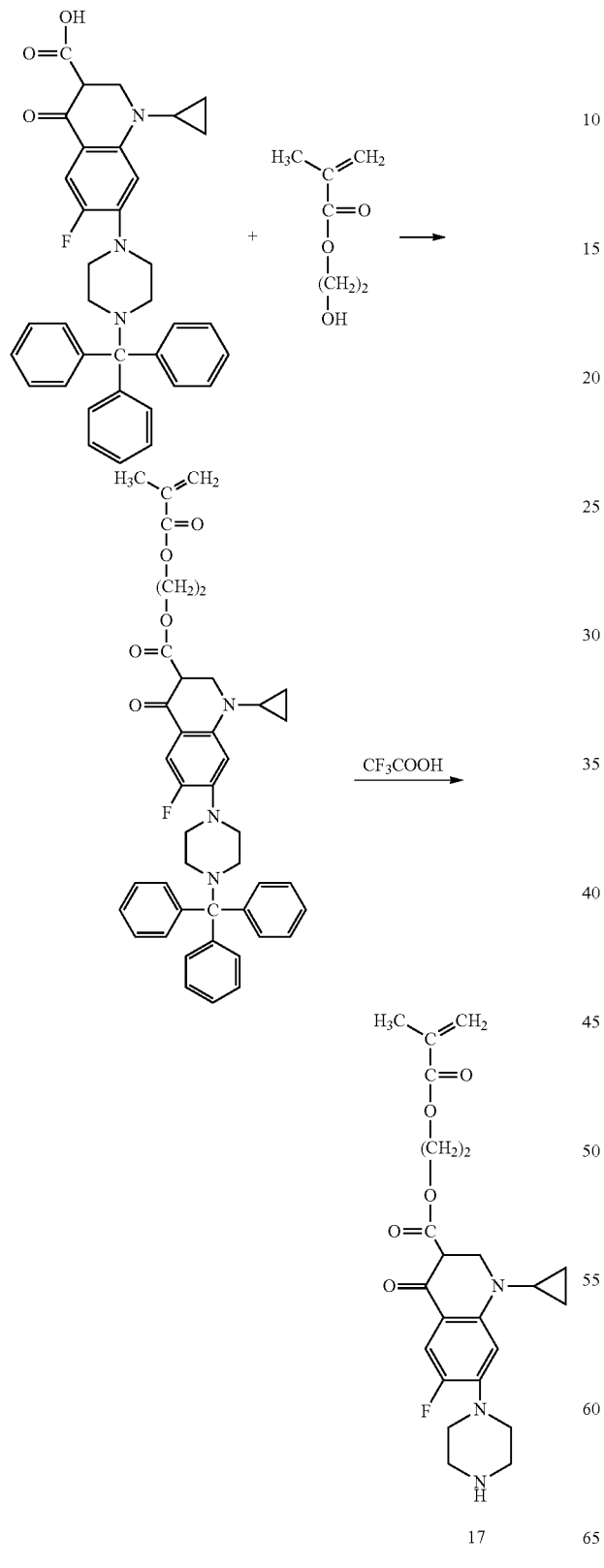

N-trityl ciprofloxacin, EDC, and DMAP (in a stoichiometry of 1:8:0.5 molar ratio) were dissolved in anhydrous DCM. 10% excess HEMA relative to the mole of COOH groups was then added into the reaction system. The reaction mixture was stirred at room temperature under $N_2$ for 7 days. After rotary evaporated the solvent, the solid residual was extracted by diethyl ether at room temperature. The crude product of this reaction was roughly dried and then was dissolved in DCM. TFAc (10 vol % of DCM) was added in the solution, stirred at room temperature for 14 hours. The solvent was removed by rotary evaporation at room temperature. The solid crude product was stirred in diethyl ether and filtered three times. The precipitated product (Compound 17) was dried under vacuum at room temperature. $^{19}F$ NMR (300 MHz, DMSO): found one multiple peak at −120.8 ppm. $^1H$ NMR (300 MHz, $CDCl_3$) found: δ (ppm): 8.44 (s, $FC_{cip}CH$), 7.80 (b, $FC_{cip}CCH$), 7.5 (b, $OC_{cip}CHN$), 6.10 (s, $\underline{H}CH=C_{HEMA}$), 5.70 (s, $HC\underline{H}=C_{HEMA}$), 4.40 (s, $OCH_2CH_2O_{HEMA}$), 3.45 (br, $N_{cip}C\underline{H}CH_2CH_2$), 2.80 (s, $_{HEMA}CCH_3$), 1.77 (s, $_{cip}NC\underline{H}_2CH_2N$), 1.25 (m, $_{cip}NCH_2CH_2NH$), 1.25 (m, $_{cip}NCH_2CH_2NH$), 1.12 (t, $_{cip}NH$).

Compound 17 (0.050 g), Compound 2 (0.500 g), BPO (0.0055 g) and pyridine (2 ml) were transferred to a 20 mL vial. The vial was vortexed until the components were completely well blended. The mixture was cast onto the desired substrates including stainless steel discs and an aluminum weighing pan. Pyridine solvent was allowed to evaporate at room temperature for 17 hours under an aluminum foil in a fume hood. The stainless steel substrates and aluminum weighing pan containing liquid samples were placed in an oven. The oven was purged with $N_2$ for three times before the heat was turned on to 110° C. for 17 hours. During this time, a gentle stream of $N_2$ was kept on positive flow through the oven. After 17 hours curing at 110° C., samples were cooled to room temperature under $N_2$, and removed from the oven for analysis. Gel content, swell ratio, contact angle measurements, DSC and TGA analyses were performed on films prepared on stainless steel substrates. XPS analysis was performed on films cast on aluminum weighing pans (0.03 mm thick). Gel extraction (acetone): 86.2% gel, 220% swelling. Contact angle: 109°. XPS analysis (90°): C: 54.77%, N: 4.15%, O: 15.14%, F: 24.85%. DSC: negative heat flow at −69° C. (associated with the $T_g$ of the PTMO). TGA: 2 onset points: (A) 227° C., 19% mass loss, (B) 392° C., 76% mass loss.

Example 60: Films of Compound 2 and Hydrocortisone-MA (Compound 18)

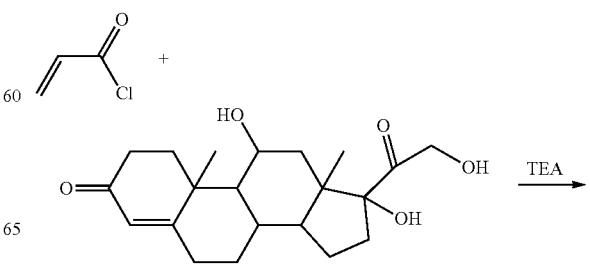

-continued

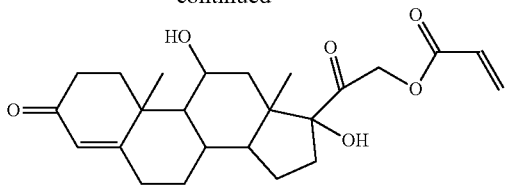

18

Hydrocortisone (2.5 g, 6.90 mmol) was transferred to a flame-dried 250 mL reaction flask equipped with a stir bar. The flask was capped by a rubber septum and filled with $N_2$ provided by a balloon. Anhydrous DCM (100 mL) was transferred to the flask via a syringe. Hydrocortisone did not dissolve in DCM completely, forming a milky suspension. TEA (1.10 ml, 7.89 mmol) was transferred to the reaction flask by a syringe. A solution of acryloyl chloride (0.65 g, 7.18 mmol in 10 ml of dry DCM) was added dropwise to the reaction flask via a syringe. The addition took about 10 minutes. As the solution of acryloyl chloride was added, the suspension became less milky. The reaction flask was kept stirring for 16 hours at room temperature. About 80 mL of DCM was removed by rotary evaporator to give a milky suspension. Flash column chromatography of the milky suspension using DCM as the eluent yielded pure hydrocortisone-containing acrylate, Compound 18. $R_f$ of Compound 18 in diethyl ether containing 2 wt % ethanol as the inhibitor: 0.46. $^1$H NMR (300 MHz, $CDCl_3$) found: δ (ppm) 6.49 (1H, dd, —OCC$\underline{H}CH_2$), 6.23 (1H, dd, —OCHC$\underline{H}_2$), 5.92 (1H, dd, —CHC$\underline{H}_2$), 5.68 (1H, s, $C^4{}_{HC}\underline{H}$), 5.13 (1H, d, OCC$\underline{H}_2$O—), 4.94 (1H, d, OCC$\underline{H}_2$O—), 4.48 (1H, b, $C^{11}{}_{HC}$HO$\underline{H}$), 2.87 (1H, m, $C^{11}{}_{HC}\underline{H}$OH), 2.60-0.94 (25H, m, $C^1{}_{HC}\underline{H}_2$, $C^2{}_{HC}\underline{H}_2$, $C^6{}_{HC}\underline{H}_2$, $C^7{}_{HC}\underline{H}_2$, $C^8{}_{HC}\underline{H}$, $C^9{}_{HC}\underline{H}$, $C^{12}{}_{HC}\underline{H}_2$, $C^{14}{}_{HC}\underline{H}$, $C^{16}{}_{HC}\underline{H}_2$, $C^{18}{}_{HC}\underline{H}_3$, $C^{19}{}_{HC}\underline{H}_3$).

Compound 18 (0.050 g), Compound 2 (0.500 g), BPO (0.0055 g) and pyridine (2 ml) were transferred to a 20 mL vial. The vial was vortexed until the components were completely well blended. The mixture was cast onto the desired substrates including stainless steel discs and an aluminum weighing pan. Pyridine solvent was allowed to evaporate at room temperature for 17 hours under an aluminum foil in a fume hood. The stainless steel substrates and aluminum weighing pan containing liquid samples were placed in an oven. The oven was purged with $N_2$ for three times before the heat was turned on to 110° C. for 17 hours. During this time, a gentle stream of $N_2$ was kept on positive flow through the oven. After 17 hours curing at 110° C., samples were cooled to room temperature under an $N_2$ environment, and removed from the oven for analysis. Gel content, swell ratio, contact angle measurements, DSC and TGA analyses were performed on films prepared on stainless steel substrates. XPS analysis was performed on films cast on aluminum weighing pans (0.03 mm thick). Gel extraction (acetone): 96.8% gel, 161% swelling. Contact angle: 109°. XPS analysis (90°): C: 50.94%, N: 3.38%, O: 11.41%, F: 34.27%. DSC: negative heat flow at −68.7° C. (associated with the $T_g$ of the PTMO). TGA: 2 onset points: (A) 251° C., 17% mass loss, (B) 409° C., 78% mass loss.

Example 61: Films of Compound 6 and Hydrocortisone (99:1), Heat Cure

Figure 25:
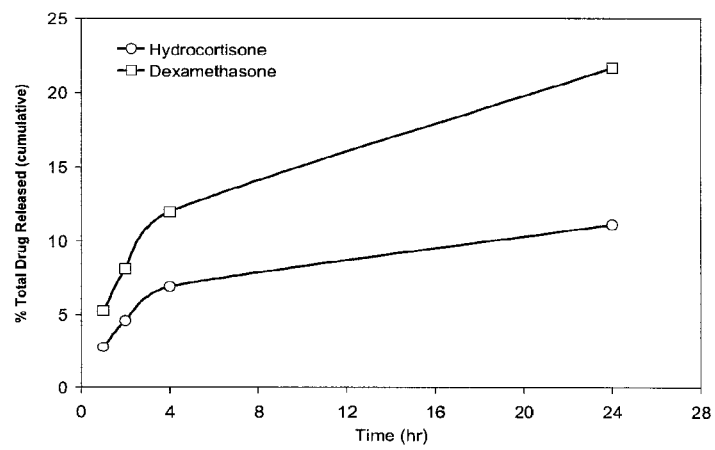
FIG. 25 is a plot of hydrocortisone and dexamethasone release from heat cured films of Compound 6, demonstrating the ability to release drugs from Compound 6.
Figure 26:
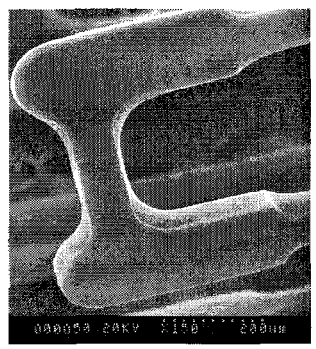
FIG. 26 is an image of a stent coated with heat cured Compound 6 with 1 wt % hydrocortisone, showing good coverage.

Hydrocortisone was mixed with Compound 6 (1 wt % of total mass) in toluene (0.1 gram/mL) containing initiator (1 wt %), and cured at 60° C. under $N_2$. The release of hydrocortisone from the cured film was measured over 24 hours in PBS solution at 37° C. by HPLC measurement (FIG. 25). A stent was coated using the same casting solution and cure method (FIG. 26).

Example 62: Films of Compound 6 and Dexamethasone (99:1), Heat Cure

Dexamethasone was mixed with Compound 6 (1 wt % of total mass) in toluene (0.1 gram/mL) containing initiator (1 wt %), and cured at 60° C. under $N_2$. The release of dexamethasone from the cured film was measured over 24 hours in PBS solution at 37° C. by HPLC measurement (FIG. 25).

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:
1. An implantable medical device having a surface and a coating on said surface, wherein said coating comprises a polymer comprising an oligofluorinated cross-linked copolymer that is formed by copolymerization of a first monomer with a second monomer, wherein said first monomer is an oligofluorinated monomer described by formula (IV):

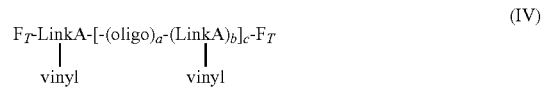

(IV)

wherein oligo is an oligomeric segment selected from the group consisting of polyalkylene oxide, polycarbonate, polyester, polylactone, polysilicone, polyethersulfone, polysiloxane, polydimethylsiloxane, polypropylene oxide, polyethylene oxide, polytetramethyleneoxide, and combinations thereof;

vinyl is a cross-linking domain comprising an unsaturated moiety capable of undergoing radical initiated polymerization;

$F_T$ is an oligofluoro group;

each LinkA is, independently, an organic moiety covalently bound to oligo, $F_T$, and vinyl; and a, b, and c are integers greater than 0;

wherein said second monomer is a compound containing one vinyl group;

wherein said polymer coating is formed by coating a substrate with a mixture of said first and said second monomers and polymerizing said first monomer with said second monomer while on said substrate.

2. The implantable medical device of claim 1, wherein $F_T$ has the formula:

$CF_3(CF_2)_pX$, $(CF_3)_2CF(CF_2)_pX$, or $(CF_3)_3C(CF_2)_pX$, wherein X is selected from $CH_2CH_2-$ and $(CH_2CH_2O)_n$, p is an integer between 2 and 20; and n is an integer between 1 and 10.

3. The implantable medical device of claim 1, wherein vinyl in formula (IV) comprises methacrylate, acrylate, allyl, vinylpyrrolidone, or a styrene derivative.

4. A method for coating an implantable medical device, said method comprising the steps of (a) contacting said implantable medical device with a first monomer and a second monomer, wherein said first monomer is described by formula (IV):

$$F_T\text{-LinkA-}[\text{-(oligo)}_a\text{-(LinkA)}_b]_c\text{-}F_T \quad \text{(IV)}$$
$$\underset{\text{vinyl}}{|} \quad \underset{\text{vinyl}}{|}$$

wherein oligo is an oligomeric segment selected from the group consisting of polyalkylene oxide, polycarbonate, polyester, polylactone, polysilicone, polyethersulfone, polysiloxane, polydimethylsiloxane, polypropylene oxide, polyethylene oxide, polytetramethyleneoxide, and combinations thereof;

vinyl is a cross-linking domain comprising an unsaturated moiety capable of undergoing radical initiated polymerization;

$F_T$ is an oligofluoro group;

each LinkA is, independently, an organic moiety covalently bound to oligo, $F_T$, and vinyl; and a, b, and c are integers greater than 0;

and (b) polymerizing said first monomer with said second monomer to form the coating on the implantable medical device of claim 1, wherein said second monomer is a compound containing one vinyl group.

5. The implantable medical device of claim 2, wherein $F_T$ is formed from poly(difluoromethylene),α-fluoro-ω-(2-hydroxyethyl) (BAL);

4,4,5,5,6,6,7,7,8,8,9,9,10,10,11,11 heptadecafluoro-2-hydroxyl;

1H, 1H, 2H, 3H nonafluorohept-2-en-ol; or 3-(perfluoro-3-methylbutyl)-2-hydroxypropyl.

6. The implantable medical device of claim 1, wherein said coating is formed by (a) contacting a shaped article with said first monomer and said second monomer, (b) polymerizing said first monomer and said second monomer to form said polymer coating.

7. The implantable medical device of claim 1, wherein said oligomeric segment is polytetramethylene oxide, LinkA is formed from lysine diisocyanate, vinyl is formed from hydroxyethylmethacrylate, and $F_T$ is formed from poly(difluoromethylene),α-fluoro-ω-(2-hydroxyethyl) (BAL).

8. The implantable medical device of claim 1, wherein said oligomeric segment is polytetramethylene oxide, LinkA is formed from lysine diisocyanate, vinyl is formed from allyl alcohol, and $F_T$ is formed from poly(difluoromethylene),α-fluoro-ω-(2-hydroxyethyl) (BAL).

9. The implantable medical device of claim 1, wherein said implantable medical device is selected from the group consisting of pacemakers, electrical leads, defibrillators, artificial hearts, ventricular assist devices, anatomical reconstruction prostheses, artificial heart valves, heart valve stents, pericardial patches, surgical patches, coronary stents, vascular grafts, vascular stents, structural stents, vascular shunts, cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, ligaments, tendons, and combinations thereof.

10. The implantable medical device of claim 9, wherein said implantable medical device is a stent.

11. The implantable medical device of claim 1, wherein said oligomeric segment is polytetramethyleneoxide.

12. The implantable medical device of claim 11, wherein said second monomer is selected from the group consisting of vinylpyrrolidone, acrylic acid, methyl acrylate, ethyl acrylate, n-butyl acrylate, 2-hydroxyethyl acrylate, n-butyl acrylate, glycidyl acrylate, vinyl acrylate, allyl acrylate, 2-hydroxy ethyl methacrylate (HEMA), 2-amino ethyl methacrylate, glycerol monomethacrylate, acrylamide, methacrylamide, N-(3-aminopropyl) methacrylamide, crotonamide, allyl alcohol, and 1,1,1-trimethylpropane monoallyl ether.

13. The implantable medical device of claim 12, wherein said second monomer is vinylpyrrolidone.

14. The implantable medical device of claim 1, wherein said second monomer is selected from the group consisting of vinylpyrrolidone, acrylic acid, methyl acrylate, ethyl acrylate, n-butyl acrylate, 2-hydroxyethyl acrylate, n-butyl acrylate, glycidyl acrylate, vinyl acrylate, allyl acrylate, 2-hydroxy ethyl methacrylate (HEMA), 2-amino ethyl methacrylate, glycerol monomethacrylate, acrylamide, methacrylamide, N-(3-aminopropyl) methacrylamide, crotonamide, allyl alcohol, and 1,1,1-trimethylpropane monoallyl ether.

15. The implantable medical device of claim 14, wherein said second monomer is vinylpyrrolidone.

16. The implantable medical device of claim 1, wherein, in formula (IV), each LinkA is independently an organic moiety bound to oligo through a urethane, covalently bound to $F_T$ through a urethane, and covalently bound to vinyl through a tether formed from a carboxylic acid and a hydroxyl.

17. The implantable medical device of claim 16, wherein vinyl in formula (IV) is formed from hydroxyethylmethacrylate.

18. The implantable medical device of claim 1, wherein said first monomer is of the following structure:

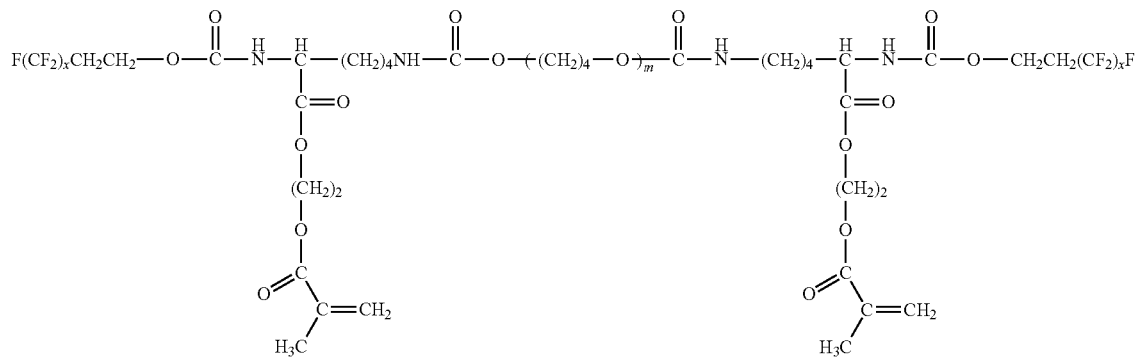

wherein m is an integer from 1 to 20.

19. The implantable medical device of claim 7, wherein said second monomer is vinylpyrrolidone.

20. The implantable medical device of claim 13, wherein said implantable medical device is a stent.

21. The implantable medical device of claim 15, wherein said implantable medical device is a stent.

22. The implantable medical device of claim 19, wherein said implantable medical device is a stent.

23. The implantable medical device of claim 1, wherein said polymer exhibits elongation at break from about 25% to about 1500%.

* * * * *